United States Patent
Babe et al.

(10) Patent No.: US 10,731,144 B2
(45) Date of Patent: Aug. 4, 2020

(54) PROTEASES WITH MODIFIED PROPEPTIDE REGIONS

(71) Applicant: DANISCO US INC., Palo Alto, CA (US)

(72) Inventors: Lilia Maria Babe, Emerald Hills, CA (US); Carol Marie Fioresi, Redwood City, CA (US); Frits Goedegebuur, Vlaardingen (NL); Harm Mulder, Oegstgeest (NL)

(73) Assignee: DANISCO US INC, Palo Alto, CA (US)

( * ) Notice: Subject to any disclaimer, the term of this patent is extended or adjusted under 35 U.S.C. 154(b) by 75 days.

(21) Appl. No.: 15/575,959

(22) PCT Filed: Jun. 17, 2016

(86) PCT No.: PCT/US2016/038177
§ 371 (c)(1),
(2) Date: Nov. 21, 2017

(87) PCT Pub. No.: WO2016/205710
PCT Pub. Date: Dec. 22, 2016

(65) Prior Publication Data
US 2018/0155701 A1    Jun. 7, 2018

Related U.S. Application Data

(60) Provisional application No. 62/181,192, filed on Jun. 17, 2015.

(51) Int. Cl.
*C12N 9/54* (2006.01)
*C12N 15/52* (2006.01)

(52) U.S. Cl.
CPC .......... *C12N 9/54* (2013.01); *C12N 15/52* (2013.01); *C12Y 304/21062* (2013.01); *C07K 2319/02* (2013.01); *C07K 2319/50* (2013.01)

(58) Field of Classification Search
None
See application file for complete search history.

(56) References Cited

U.S. PATENT DOCUMENTS

| 7,262,042 B2 | 8/2007 | Weber et al. |
| 7,449,187 B2 | 11/2008 | Weber et al. |

(Continued)

FOREIGN PATENT DOCUMENTS

| WO | 2003/054184 A1 | 7/2003 |
| WO | 2003/054185 A1 | 7/2003 |

(Continued)

OTHER PUBLICATIONS

Deng et al., "Secretory expression, functional characterization, and molecular genetic analysis of novel halo-solvent-tolerant protease from Bacillus gibsonii", Journal of Microbiology and Biotechnology, vol. 24, No. 2, pp. 197-208, 2014, including Supplemental Data (Year: 2014).*

(Continued)

*Primary Examiner* — Richard C Ekstrom

(57) ABSTRACT

The present invention provides methods and compositions for the production of mature proteases in bacterial host cells. The compositions include polynucleotides encoding serine protease sequences with modified or heterologous propeptide regions; polypeptides comprising serine proteases with modified or heterologous propeptide regions; expression cassettes, DNA constructs, vectors, and chromosomes comprising such polynucleotides; and bacterial host cells comprising such polynucleotides. The methods include methods for enhancing the production of mature proteases in bacterial host cells (e.g. *Bacillus* sp. host cells). The produced proteases find use in the industrial production of enzymes, (Continued)

suitable for use in various industries, including but not limited to the cleaning, animal feed and textile processing industry.

2 Claims, 12 Drawing Sheets

Specification includes a Sequence Listing.

(56) References Cited

U.S. PATENT DOCUMENTS

| | | | |
|---|---|---|---|
| 2005/0113273 A1* | 5/2005 | Weber | A61K 8/64 510/320 |
| 2009/0275493 A1 | 11/2009 | Siegert et al. | |
| 2011/0045571 A1* | 2/2011 | Ferrari | C12N 15/75 435/221 |
| 2018/0155701 A1* | 6/2018 | Babe | C12Y 304/21062 |

FOREIGN PATENT DOCUMENTS

| | | |
|---|---|---|
| WO | 2007/131657 A2 | 11/2007 |
| WO | 2008/086916 A1 | 7/2008 |
| WO | 2010/123754 A1 | 10/2010 |
| WO | 2011/014278 A1 | 2/2011 |
| WO | 2015/089447 A1 | 6/2015 |
| WO | 2016/069563 A1 | 5/2016 |
| WO | 2016/069569 A2 | 5/2016 |

OTHER PUBLICATIONS

Aihua Deng et al., Secretory Expression, Functional Characterization, and Molecular Genetic Analysis of Novel Halo-Solvent-Tolerant Protease from *Bacillus gibsonii*, J. Microbiol. Biotechnol. 2014, 24:197-208.

Ronny Martinez et al., Increasing Activity and Thermal Resistance of *Bacillus gibsonii* Alkaline Protease (BgAP) by Directed Evolution, Biotechnology and Bioengineering, Mar. 2013, vol. 110, No. 3.

Database Accession No. AYL49287, *Bacillus* sp. Pro region-alkaline serine protease fusion, SEQ ID 40, XP002760538, Dec. 23, 2010.

Database Accession No. AYL49301, *Bacillus* sp. YAB alkaline elastase YaB pro region sequence, SEQ ID 54, XP002760539, Dec. 23, 2013.

Database Accession No. BBW25696, *Bacillus* sp. m3 subtilisin E (1) protease precursor protein, SEQ: 6, XP002760541, May 7, 2015.

Database Accession No. HI648850, Sequence 12 from Patent WO2010123743, XP002760540, Nov. 16, 2010.

International Search Report, PCT/US2016/038177, dated Aug. 23, 2016.

* cited by examiner

B. lentus pro peptide-BSP00801 mature expression cassette
2872 bp

```
Total alignment length: 93
Number of identity: 33
Number of residues aligned: 86
BLAST style alignment length: 91
Percent identity (BLAST style): 36.26%
Percent identity (GAP style): 38.37%
Percent identity (Needle style): 35.48%

SEQ_59    -AEEKVKYLIGFEEEAELEAFTEEIDQVGVFSVEEQSVAEDTLDIDVDIIDEYDYIDVLA
SEQ_60    AEEAKEKYLIGFNEQEAVSEFVEQVE-----ANDEVAILSEEEEVEIELLHEFETIPVLS

SEQ_59    VELDPEDVDALSEEAGISFIEEDIELSI-QQTV-
SEQ_60    VELSPEDVDALELDPAISYIEEDAEVTTMAQSV
```

FIG. 8

CLUSTAL X (1.81) multiple sequence alignment

```
SEQIDNO_3        ---GCAGAAGAAAAAGTAAAATACTTAATAGGTTTCGAAGAAGAAGCAGA
SEQIDNO_5        GCTGAAGAAGCAAAAGAAAAATATTTAATTGGCTTTAATGAGCAGGAAGC

SEQIDNO_3        ACTTGAAGCCTTCACTGAGGAAATTGACCAAGTTGGTGTATTTTCTGTTG
SEQIDNO_5        TGTCAGTGAGTTTGTAGAACAAGTAGAG---------------GCAAATG

SEQIDNO_3        AAGAACAAAGTGTAGCTGAGGATACGTTAGATATTGATGTAGACATTATT
SEQIDNO_5        ACGAGGTCGCCATTCTCTCTGAGGAAGAGGAAGTCGAAATTGAATTGCTT

SEQIDNO_3        GATGAATATGATTATATTGATGTGTTAGCTGTAGAATTAGATCCTGAGGA
SEQIDNO_5        CATGAATTTGAAACGATTCCTGTTTTATCCGTTGAGTTAAGCCCAGAAGA

SEQIDNO_3        TGTAGATGCGTTAAGTGAAGAAGCAGGTATCTCATTTATTGAAGAAGACA
SEQIDNO_5        TGTGGACGCGCTTGAGCTCGATCCAGCGATTTCTTATATTGAAGAGGATG

SEQIDNO_3        TTGAACTGTCTATT
SEQIDNO_5        CAGAAGTAACGACA
```

FIG. 9

Clustal W Sequence Alignment for Multiple Bacillus Subtilisin Pro Peptides

```
                           1                                                    50
BspAK01305       (1)  -AEEKKSYLIGFDEPQEVEQFTTNLEEE------------IRTQADDAIDVT
BspAL03279       (1)  -EETKKTYLIGFDAQEEVETFTNMVDSE------------IGALSEEEIDIT
Bgi02446         (1)  -AEEKVKYLIGFEEEAELEAFTEEIDQVGVFSVEEQSVAEDTLDIDVDII
B.lentus_P29600  (1)  AEEAKEKYLIGFNEQEAVSEFVEQVE------ANDEVAILSEEEEVEIELL
B.clausii_P41362 (1)  AEEAKEKYLIGFNEQEAVSEFVEQVE------ANDEVAILSEEEEVEIELL
BspAL03240       (1)  AEEAKEKYLIGFTEQEAVSTFVEQIEE-----------EEVSIEVDDVEIDLL
B.lehensis_AFK08970 (1) AEEAKEKYLIGFKEQEVMSQFVDQIDG-----------DEYSISSQAEDVEIDLL
BspQ01211        (1)  AEEQKKQYLIGFENQVSVTEFVESSEKGK--DEFSIFAEINDETIEMDLL
Bps02592         (1)  AEEIKKQYLIGFENQLQVTEFLEATEKGN--DQVSLFAEVNNDTVEMELL
Bps02003         (1)  -DEEKKTYLIGFHNQLDVNEFIEEDVTNTN-GVQLYTSEDKSAQVQLEVL 51                                                89
BspAK01305       (40) YEFKDIPVLAVDMTEEEMTELKNEESISYIEEDQEVTTM   (SEQ ID NO:54)
BspAL03279       (40) YEFKEIPVVSAEMSEEYAALLEDPSISYIEEDIEVTTM   (SEQ ID NO:56)
Bgi02446         (50) DEYDYIDVLAVELDPEDVDALSEEAGISFIEEDIELSI-   (SEQ ID NO:7)
B.lentus_P29600  (46) HEFETIPVLSVELSPEDVDALELDPAISYIEEDAEVTTM  (SEQ ID NO:8)
B.clausii_P41362 (46) HEFETIPVLSVELSPEDVDALELDPAISYIEEDAEVTTM  (SEQ ID NO:42)
BspAL03240       (44) YEFETIPVLSVEINPEDVASLESDPAISYIEEDAEVTTM  (SEQ ID NO:51)
B.lehensis_AFK08970 (45) HEFDFIPVLSVELDPEDVDALELDPAIAYIEEDAEVTT-  (SEQ ID NO:43)
BspQ01211        (49) YEFEDIPVVSVEVSPEDVKDLEGDPSIAFIEEDIEVSIF  (SEQ ID NO:49)
Bps02592         (49) YEFEEIPVVSVELSPEDVQSLKKDPSIAYVEEDVEVKIA  (SEQ ID NO:50)
Bps02003         (49) HEFEQIPVVAVELSPADIKALEAESGIAYIEEDFDVTIA  (SEQ ID NO:48)
```

FIG. 10

Bacillus pro peptide sequence motif

| Position | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| Amino Acid | X | X | E | X | K | X | X | Y | L | I | G | F | X | X | X | X | X | X | X | X |

| Position | 21 | 22 | 23 | 24 | 25 | 26 | 27 | 28 | 29 | 30 | 31 | 32 | 33 | 34 | 35 | 36 | 37 | 38 | 39 | 40 |
|---|---|---|---|---|---|---|---|---|---|---|---|---|---|---|---|---|---|---|---|---|
| Amino Acid | F | X | X | X | X | X | X | X | X | X | X | X | X | X | X | X | X | X | X | X |

| Position | 41 | 42 | 43 | 44 | 45 | 46 | 47 | 48 | 49 | 50 | 51 | 52 | 53 | 54 | 55 | 56 | 57 | 58 | 59 | 60 |
|---|---|---|---|---|---|---|---|---|---|---|---|---|---|---|---|---|---|---|---|---|
| Amino Acid | X | X | X | X | X | X | X | X | X | X | X | E | F/Y | X | X | I | D/P | V | L/V | A/S |

| Position | 61 | 62 | 63 | 64 | 65 | 66 | 67 | 68 | 69 | 70 | 71 | 72 | 73 | 74 | 75 | 76 | 77 | 78 | 79 | 80 |
|---|---|---|---|---|---|---|---|---|---|---|---|---|---|---|---|---|---|---|---|---|
| Amino Acid | V/A | E/D | X | X | P/E | E/A | D/E | X | X | X | L | X | X | D/E | X | X | I | S/A | F/Y | I |

| Position | 81 | 82 | 83 | 84 | 85 | 86 | 87 | 88 | 89 |
|---|---|---|---|---|---|---|---|---|---|
| Amino Acid | E | E | D | X | E/D | V/L | X | X | X |

FIG. 11

NARROWER CONSENSUS

| Position | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| Amino Acid | A | E | E | A | K | E | K | Y | L | I | G | F | X | E | Q | E | A/V | V/M | S | X |

| Position | 21 | 22 | 23 | 24 | 25 | 26 | 27 | 28 | 29 | 30 | 31 | 32 | 33 | 34 | 35 | 36 | 37 | 38 | 39 | 40 |
|---|---|---|---|---|---|---|---|---|---|---|---|---|---|---|---|---|---|---|---|---|
| Amino Acid | F | V | E/D | Q | V/I | E/D | X | N | D | E | X | X | I/S | X | S | E/Q | X | E/D | E/D | V |

| Position | 41 | 42 | 43 | 44 | 45 | 46 | 47 | 48 | 49 | 50 | 51 | 52 | 53 | 54 | 55 | 56 | 57 | 58 | 59 | 60 |
|---|---|---|---|---|---|---|---|---|---|---|---|---|---|---|---|---|---|---|---|---|
| Amino Acid | E | I | E/D | L | L | H/Y | E | F | E/D | T/F | I | P | V | L | S | V | E | L/I | X | P |

| Position | 61 | 62 | 63 | 64 | 65 | 66 | 67 | 68 | 69 | 70 | 71 | 72 | 73 | 74 | 75 | 76 | 77 | 78 | 79 | 80 |
|---|---|---|---|---|---|---|---|---|---|---|---|---|---|---|---|---|---|---|---|---|
| Amino Acid | E | D | V | D/A | A/S | L | E | L/S | D | P | A | I | S/A | Y | I | E | E | D | A | E |

| Position | 81 | 82 | 83 | 84 |
|---|---|---|---|---|
| Amino Acid | V | T | T | M |

FIG. 12

PROTEASES WITH MODIFIED PROPEPTIDE REGIONS

CROSS-REFERENCE TO RELATED APPLICATIONS

The present application is the National Stage of International Application, PCT Patent Application No. PCT/US2016/038177, filed on Jun. 17, 2016, which claims the benefit of U.S. Provisional Application Ser. No. 62/181,192, filed Jun. 17, 2015, which are incorporated herein by referenced in their entirety.

REFERENCE TO A SEQUENCE LISTING

This application contains a Sequence Listing, which has been submitted via EFS, in compliance with 37 C.F.R. § 1.52(e). The contents of the electronic submission of the text file sequence listing, named "NB40947WOPCT_SEQUENCELISTING.txt" was created on Jun. 16, 2016 and is 71.7 KB (73,457 bytes) in size, is hereby incorporated by reference in its entirety.

FIELD OF THE INVENTION

The present invention provides methods and compositions for the production of mature proteases in bacterial host cells. The compositions include polynucleotides encoding serine protease sequences with modified or heterologous propeptide regions; polypeptides comprising serine proteases with modified or heterologous propeptide regions; expression cassettes, DNA constructs, vectors, and chromosomes comprising such polynucleotides; and bacterial host cells comprising such polynucleotides. The methods include methods for enhancing the production of mature proteases in bacterial host cells (e.g., *Bacillus* sp. host cells). The produced proteases find use in the industrial production of enzymes, suitable for use in various industries, including but not limited to the cleaning, animal feed and textile processing industry.

BACKGROUND

Microorganisms, such as the Gram-positive microorganisms that are members of the genus *Bacillus*, have been used for large-scale industrial fermentation due, in part, to their ability to secrete their fermentation products into their culture media. Secreted proteins are exported across a cell membrane and a cell wall, and then are subsequently released into the external media.

Indeed, secretion of heterologous polypeptides is a widely used technique in industry. Typically, cells are transformed with a nucleic acid encoding a heterologous polypeptide of interest to be expressed and secreted to produce large quantities of desired polypeptides. In some cases, the chromosomes of host cells are modified to encode such a heterologous polypeptide. Expression and secretion of desired polypeptides has been controlled through genetic manipulation of the polynucleotides that encode the desired proteins. Despite various advances in protein production methods, there remains a need in the art to provide more efficient methods for extracellular protein secretion with the aim to enhance the production of enzymes such as proteases, which find use in the use in various industries, including but not limited to the cleaning, animal feed and textile processing industry.

SUMMARY OF THE INVENTION

The present invention provides methods and compositions for the production of mature proteases in bacterial host cells. The compositions include polynucleotides encoding serine protease sequences with modified or heterologous propeptide regions; polypeptides comprising serine proteases with modified or heterologous propeptide regions; expression cassettes, DNA constructs, vectors, and chromosomes comprising such polynucleotides; and bacterial host cells comprising such polynucleotides. The methods include methods for enhancing the production of mature proteases in bacterial host cells (e.g., *Bacillus* sp. host cells). The produced proteases find use in the industrial production of enzymes, suitable for use in various industries, including but not limited to the cleaning, animal feed and textile processing industry.

In one aspect, the invention provides polynucleotides encoding serine protease sequences with modified propeptide regions.

Thus, in certain embodiments, the disclosure is directed to a polynucleotide encoding a modified protease comprising (a) an optional first polynucleotide region encoding a signal peptide; (b) a second polynucleotide region encoding the propeptide region of a heterologous *Bacillus* protease, the propeptide region comprising an amino acid sequence with at least 40% identity to SEQ ID NO: 8 and (c) a third polynucleotide region encoding the mature region of a *Bacillus gibsonii*-clade protease, wherein the first polynucleotide region is operably linked to the second polynucleotide region, and the second polynucleotide region is operably linked to the third polynucleotide region.

In other embodiments, the disclosure is directed to a polynucleotide encoding a protease, said polynucleotide comprising (a) an optional first polynucleotide region encoding a signal peptide, (b) a second polynucleotide region encoding the propeptide region of a protease from *Bacillus lentus* or a related species thereof and (c) a third polynucleotide region encoding the mature region of a *Bacillus gibsonii*-clade protease, wherein the first polynucleotide region is operably linked to the second polynucleotide region, and the second polynucleotide region is operably linked to the third polynucleotide region.

In certain embodiments, the second polynucleotide region encodes the propeptide region of a protease from *Bacillus lentus* or a related species thereof. In other embodiments, the second polynucleotide region encodes the propeptide region of a protease from a *Bacillus* species selected from the group consisting of *B. lentus, B. clausii, B. alcalophilus, B. lehensis* and *B. novalis*. In particular embodiments, the second polynucleotide region encodes the propeptide region of a *Bacillus lentus* protease. In other embodiments, the second polynucleotide region encodes the propeptide region of a serine protease or subtilisin from *Bacillus lentus* or a related species thereof. In other embodiments, the second polynucleotide region encodes a wild-type propeptide region of a subtilisin from *Bacillus lentus* or a related species thereof. In yet other embodiments, the second polynucleotide region encodes a variant propeptide region of a subtilisin from *Bacillus lentus* or a related species thereof.

In other embodiments, the second polynucleotide region encodes the propeptide region of a subtilisin selected from the group consisting of BspQ01211, Bps02592, *B. lentus*_P29600, BspAL03240, Bpan01744, *B. clausii*_P41362, *B. lehensis*_AFK08970, Bps02003, Bohn00569, BspAK01305, Bpan04382, and BspAL03279. In another embodiment, the second polynucleotide region encodes the propeptide region of a subtilisin selected from the group consisting of BspQ01211, Bps02592, B. lentus_P29600, BspAL03240, B. clausii_P41362, B. lehensis_AFK08970, and Bpan01744. In other embodiments, the second polynucleotide region encodes the propeptide region of B. lentus_P29600.

In certain embodiments, the second polynucleotide region encodes an amino acid sequence with at least 50% identity to SEQ ID NO: 8. In other embodiments, the second polynucleotide region encodes an amino acid sequence with at least 75% identity to SEQ ID NO: 8 In another embodiment, the second polynucleotide region encodes an amino acid sequence with at least 90% identity to SEQ ID NO: 8 In other embodiments, the second polynucleotide region encodes an amino acid sequence comprising the sequence of SEQ ID NO: 8

In certain other embodiments, the second polynucleotide region encodes a variant propeptide region of a subtilisin from Bacillus lentus or a related species thereof, wherein the variant propeptide region comprises at least one amino acid substitution at a position corresponding to position 6, 30, or 32 of SEQ ID NO: 8 In another embodiment, the second polynucleotide region comprises at least one amino acid substitution which enhances production of the mature region of the Bacillus gibsonii-clade protease by a Bacillus sp. host cell.

In certain other embodiments, the at least one amino acid substitution enhances production of said mature region of the *Bacillus gibsonii*-clade protease as compared to a polynucleotide comprising the same first polynucleotide region and third polynucleotide region, but a different second polynucleotide region encoding a wild-type propeptide region of the same subtilisin. In another embodiment, the at least one amino acid substitution is at the position corresponding to position 6 of SEQ ID NO: 8, and the native amino acid at said position is substituted with an amino acid selected from the group consisting of A, C, R, N, Q, G, H, I, L, K, M, F, P, S, T, W, Y, and V. In yet another embodiment, the at least one amino acid substitution is at the position corresponding to position 30 of SEQ ID NO: 8, and the native amino acid at said position is substituted with an amino acid selected from the group consisting of A, R, N, D, C, Q, G, H, L, K, M, S, T, W, Y, and V. In certain other embodiments, the at least one amino acid substitution is at the position corresponding to position 32 of SEQ ID NO: 8, and the native amino acid at said position is substituted with an amino acid selected from the group consisting of R, N, C, Q, G, H, I, L, K, M, F, P, S, T, W, Y, and V.

In certain other embodiments, the second polynucleotide region encodes the propeptide region set forth in SEQ ID NO: 8, with the proviso that the propeptide region comprises at least one amino acid substitution at a position chosen from positions 6, 30 and 32 of SEQ ID NO: 8. In another embodiment, the propeptide region comprises an amino acid substitution at position 6 of SEQ ID NO: 8 selected from the group consisting of E6A, E6C, E6R, E6N, E6Q, E6G, E6H, E6I, E6L, E6K, E6M, E6F, E6P, E6S, E6T, E6W, E6Y, and E6V. In other embodiments, the propeptide region comprises an amino acid substitution at position 30 of SEQ ID NO: 8 selected from the group consisting of E30A, E30R, E30N, E30D, E30C, E30Q, E30G, E30H, E30L, E30K, E30M, E30S, E30T, E30W, E30Y, and E30V. In yet other embodiments, the propeptide region comprises an amino acid substitution at position 32 of SEQ ID NO: 8 selected from the group consisting of A32R, A32N, A32C, A32Q, A32G, A32H, A32I, A32L, A32K, A32M, A32F, A32P, A32S, A32T, A32W, A32Y, and A32V.

In another embodiment, the second polynucleotide region comprises a nucleotide sequence with at least 60% identity to SEQ ID NO: 5. In other embodiments, the second polynucleotide region comprises a nucleotide sequence with at least 90% identity to SEQ ID NO: 5. In certain other embodiments, the second polynucleotide region comprises the sequence of SEQ ID NO: 5. In another embodiment, the second polynucleotide region comprises the sequence set forth in SEQ ID NO: 5 with the proviso that the sixth ($6^{th}$), the thirtieth ($30^{th}$), or the thirty second ($32^{nd}$) codon of SEQ ID NO: 5 is mutated to encode a different amino acid. In certain embodiments, a *Bacillus* sp. host cell is a *Bacillus subtilis* host cell.

In other embodiments, the disclosure is directed to a polynucleotide encoding a modified protease, said polynucleotide comprising (a) an optional first polynucleotide region encoding a signal peptide, (b) a second polynucleotide region encoding a variant propeptide region of a first *Bacillus gibsonii*-clade protease and (c) a third polynucleotide region encoding the mature region of a second *Bacillus gibsonii*-clade protease; wherein the first polynucleotide region is operably linked to the second polynucleotide region, and the second polynucleotide region is operably linked to the third polynucleotide region. In particular embodiments, the first *Bacillus gibsonii*-clade protease or said second *Bacillus gibsonii*-clade protease is a serine protease or subtilisin. In other embodiments, the first *Bacillus gibsonii*-clade protease and said second *Bacillus gibsonii*-clade protease are from the same *Bacillus* species. In other embodiments, the first *Bacillus gibsonii*-clade protease and said second *Bacillus gibsonii*-clade protease are from different *Bacillus* species.

In another embodiment, the second polynucleotide region encodes an amino acid sequence with at least 60% identity to SEQ ID NO: 7. In other embodiments, the second polynucleotide region encodes an amino acid sequence with at least 90% identity to SEQ ID NO: 7.

In yet other embodiments, the second polynucleotide region encodes a variant propeptide region with at least 60% identity to SEQ ID NO: 7, wherein the variant propeptide region comprises an amino acid substitution at a position corresponding to position 34 of SEQ ID NO: 7. In certain other embodiments, the second polynucleotide region encodes the propeptide region set forth in SEQ ID NO: 7, with the proviso that the propeptide region comprises an amino acid substitution at position 34 of SEQ ID NO: 7. In certain other embodiments, the native amino acid at said position is substituted with an amino acid selected from the group consisting of D, C, G, H, S, and V. In another embodiment, the amino acid substitution at position 34 of SEQ ID NO: 7 is selected from the group consisting of E34D, E34C, E34G, E34H, E34S, and E34V.

In other embodiments, the amino acid substitution enhances the production of the mature region of the second *Bacillus gibsonii*-clade protease by a *Bacillus* sp. host cell. In certain embodiments, the *Bacillus* sp. host cell is a *Bacillus subtilis* host cell.

In yet other embodiments, the second polynucleotide region comprises a nucleotide sequence with at least 60% identity to SEQ ID NO: 3. In other embodiments, the second polynucleotide region comprises a nucleotide sequence with at least 90% identity to SEQ ID NO: 3. In yet other embodiments, the second polynucleotide region comprises the sequence set forth in SEQ ID NO: 3, with the proviso that the thirty-fourth ($34^{th}$) codon of SEQ ID NO: 3 is mutated to encode a different amino acid.

In certain embodiments, the second polynucleotide region encodes a heterologous or variant propeptide region that comprises an amino acid sequence set forth in SEQ ID NO: 44. In another embodiment, the second polynucleotide region encodes a heterologous or variant propeptide region that comprises an amino acid sequence set forth in SEQ ID NO: 69.

In yet other embodiments, the third polynucleotide region encodes the mature region of a protease from *Bacillus gibsonii*. In other embodiments, the third polynucleotide region encodes the mature region of a *Bacillus gibsonii*-clade serine protease or subtilisin. In another embodiment, the third polynucleotide region encodes the mature region of a wild-type *Bacillus gibsonii*-clade subtilisin. In yet other embodiments, the third polynucleotide region encodes the mature region of a variant *Bacillus gibsonii*-clade subtilisin.

In certain other embodiments, the third polynucleotide region encodes the mature region of a subtilisin selected from the group consisting of Bgi02446, DSM9728, DSM9729, DSM9730, DSM9731, *B. gibsonii* 111-5, *B. gibsonii* TI-1 and *B. gibsonii* HP302. In another embodiment, the third polynucleotide region encodes the mature region of Bgi024446. In certain embodiments, the third polynucleotide region encodes the mature region of a variant of Bgi024446 (e.g., BSP-00801).

In other embodiments, the third polynucleotide region encodes an amino acid sequence with at least 60% identity to SEQ ID NO: 10, 11, 12, or 13. In certain other embodiments, the third polynucleotide region encodes an amino acid sequence with at least 75% identity to SEQ ID NO: 10, 11, 12, or 13. In another embodiment, the third polynucleotide region encodes an amino acid sequence with at least 90% identity to SEQ ID NO: 10, 11, 12, or 13. In certain other embodiments, the third polynucleotide region encodes an amino acid sequence comprising the sequence of SEQ ID NO: 10, 11, 12, or 13. In certain embodiments, the third polynucleotide region encodes an amino acid sequence comprising the sequence of SEQ ID NO: 10 or 11. In other embodiments, the third polynucleotide region encodes an amino acid sequence comprising the sequence of SEQ ID NO: 12 or 13.

In certain other embodiments, the third polynucleotide region comprises a nucleotide sequence with at least 60% identity to SEQ ID NO: 4 or 9. In other embodiments, the third polynucleotide region comprises a nucleotide sequence with at least 75% identity to SEQ ID NO: 4 or 9. In yet other embodiments, the third polynucleotide region comprises a nucleotide sequence with at least 90% identity to SEQ ID NO: 4 or 9. In another embodiment, the third polynucleotide region comprises the sequence of SEQ ID NO: 4 or 9. In other embodiments, the third polynucleotide region comprises the sequence of SEQ ID NO: 4. In yet other embodiments, the third polynucleotide region comprises the sequence of SEQ ID NO: 9.

In certain other embodiments, the first polynucleotide region is present and encodes a *Bacillus* signal peptide. In another embodiment, the first polynucleotide region is present and encodes a *Bacillus subtilis* signal peptide. In another embodiment the first polynucleotide region is present and encodes an amino acid sequence with at least 60% identity to SEQ ID NO: 40. In other embodiments, the first polynucleotide region is present and encodes an amino acid sequence with at least 90% identity to SEQ ID NO: 40. In another embodiment, the first polynucleotide region is present and encodes an amino acid sequence comprising the sequence of SEQ ID NO: 40.

In certain other embodiments, the first polynucleotide region is present and comprises a nucleotide sequence with at least 60% identity to SEQ ID NO: 2. In other embodiments, the first polynucleotide region is present and comprises a nucleotide sequence with at least 90% identity to SEQ ID NO: 2: In yet other embodiments, the first polynucleotide region is present and comprises the nucleotide sequence of SEQ ID NO: 2:

In other embodiments, the disclosure is directed to a polynucleotide encoding a modified protease comprising (a) a first polynucleotide region encoding the amino acid sequence of SEQ ID NO: 40, (b) a second polynucleotide region encoding the amino acid sequence of SEQ ID NO: 8 or encoding the sequence of SEQ ID NO: 8 with at least one amino acid substitution selected from the group consisting of E6A, E6C, E6R, E6N, E6Q, E6G, E6H, E6I, E6L, E6K, E6M, E6F, E6P, E6S, E6T, E6W, E6Y, E6V, E30A, E30R, E30N, E30D, E30C, E30Q, E30G, E30H, E30L, E30K, E30M, E30S, E30T, E30W, E30Y, E30V, A32R, A32N, A32C, A32Q, A32G, A32H, A32I, A32L, A32K, A32M, A32F, A32P, A32S, A32T, A32W, A32Y, and A32V and (c) a third polynucleotide region encoding the amino acid sequence of SEQ ID NO: 11 or 12, wherein the first polynucleotide region is operably linked to the second polynucleotide region, and the second polynucleotide region is operably linked to the third polynucleotide region.

In other embodiments, the disclosure is directed to a polynucleotide encoding a modified protease comprising (a) a first polynucleotide region encoding the amino acid sequence of SEQ ID NO: 40, (b) a second polynucleotide region encoding the amino acid sequence of SEQ ID NO: 7 with an amino acid substitution selected from the group consisting of E34D, E34C, E34G, E34H, E34S, and E34V and (c) a third polynucleotide region encoding the amino acid sequence of SEQ ID NO: 11 or 12, wherein the first polynucleotide region is operably linked to the second polynucleotide region, and the second polynucleotide region is operably linked to the third polynucleotide region.

In certain embodiments, the disclosure is directed to an expression vector comprising a polynucleotide of the disclosure. In other embodiments, the disclosure is directed to a modified chromosome comprising a polynucleotide of the disclosure. In certain other embodiments, an expression vector or a modified chromosome comprising a polynucleotide of the disclosure further comprises a promoter that is suitable for gene expression in *Bacillus subtilis*. Thus, in particular embodiments, the disclosure is directed to a *Bacillus* species host cell comprising a polynucleotide of the disclosure. Thus in certain other embodiments, a *Bacillus* species host cell of the disclosure comprises an expression vector or a modified chromosome of the disclosure.

In certain embodiments, the host cell is a *B. subtilis* host cell.

In certain other embodiments, the disclosure is directed to a method for producing a mature protease in a *Bacillus* sp. host cell comprising (a) providing an expression vector comprising a polynucleotide of the disclosure, (b) transforming a *Bacillus* sp. host cell with the expression vector; and (c) culturing the host cell under suitable conditions such that the mature protease is produced by the host cell. In certain embodiments, the *Bacillus* species host cell is *Bacillus subtilis*. In other embodiments, the mature protease is a wild-type *Bacillus gibsonii*-clade serine protease, a variant thereof, or a homolog thereof.

In certain embodiments of the methods for producing a mature protease in a *Bacillus* species host cell, the mature protease is expressed at a higher level than a host cell comprising an expression vector or modified chromosome which comprises the same first polynucleotide region and third polynucleotide region, but a different second polynucleotide region encoding a wild-type propeptide region of the *B. gibsonii*-clade protease encoded by the third polynucleotide region. In other embodiments, the second polynucleotide region encodes a variant propeptide region of a subtilisin from *Bacillus lentus* or a related species thereof, and wherein the mature protease is expressed at a higher level than by a host cell comprising an expression vector or modified chromosome which comprises the same first polynucleotide region and third polynucleotide region, but a different second polynucleotide region encoding a wild-type propeptide region of the same subtilisin from *Bacillus lentus* or a related species thereof. In certain embodiments, the produced mature protease begins with two glutamines in the N-terminal position. In certain other embodiments, the produced mature protease has at least 90% identity to SEQ ID NO: 11 or 12. In another embodiment, the produced mature protease comprises the sequence of SEQ ID NO: 11 or 12.

In other embodiments, the disclosure is directed to a polypeptide encoded by a polynucleotide of the disclosure. Thus, in certain embodiments, the disclosure is directed to a polypeptide comprising a modified protease, wherein the protease comprises the propeptide region of a heterologous *Bacillus* protease operably linked to the mature region of a *Bacillus gibsonii*-clade protease, wherein the propeptide region comprises an amino acid sequence with at least 40% identity to SEQ ID NO: 8. In other embodiments, the heterologous *Bacillus* protease is from *Bacillus lentus* or a related species thereof.

In other embodiments, the disclosure is directed to a polypeptide comprising a modified protease, wherein the modified protease comprises the propeptide region of a heterologous *Bacillus* protease operably linked to the mature region of a *Bacillus gibsonii*-clade protease, wherein the heterologous *Bacillus* protease is from *Bacillus lentus* or a related species thereof. In certain embodiments, the heterologous *Bacillus* protease is from a *Bacillus* species selected from the group consisting of *Bacillus lentus, Bacillus clausii, Bacillus alcalophilus, Bacillus lehensis*, and *Bacillus novalis*. In particular embodiments, the heterologous *Bacillus* protease is from *Bacillus lentus*. In another embodiment, the heterologous *Bacillus* protease is a serine protease or subtilisin. In another embodiment, the propeptide region is a wild-type propeptide region of a subtilisin from *Bacillus lentus* or a related species thereof. In certain other embodiments, the propeptide region is a variant propeptide region of a subtilisin from *Bacillus lentus* or a related species thereof. In another embodiment, the heterologous *Bacillus* protease is selected from the group consisting of BspQ01211, Bps02592, *B. lentus*_P29600, BspAL03240, Bpan01744, *B. clausii*_P41362, *B. lehensis*_AFK08970, Bps02003, Bohn00569, BspAK01305, Bpan04382 and BspAL03279. In another embodiment, the heterologous *Bacillus* protease is selected from the group consisting of BspQ01211, Bps02592, *B. lentus*_P29600, BspAL03240, *B. clausii*_P41362, *B. lehensis*_AFK08970 and Bpan01744. In another embodiment, the heterologous *Bacillus* protease is *B. lentus*_P29600. In yet other embodiments, the propeptide region comprises an amino acid sequence with at least 50% identity to SEQ ID NO: 8. In certain other embodiments, the propeptide region comprises an amino acid sequence with at least 75% identity to SEQ ID NO: 8. In another embodiment, the propeptide region comprises an amino acid sequence with at least 90% identity to SEQ ID NO: 8. In other embodiments, the propeptide region comprises the sequence of SEQ ID NO: 8

In yet other embodiments, the propeptide region is a variant propeptide region of a subtilisin from *Bacillus lentus* or a related species thereof, wherein the variant propeptide region comprises at least one amino acid substitution at a position corresponding to position 6, 30, or 32 of SEQ ID NO: 8. In another embodiment, the at least one amino acid substitution is at the position corresponding to position 6 of SEQ ID NO: 8, and is selected from the group consisting of E6A, E6C, E6R, E6N, E6Q, E6G, E6H, E6I, E6L, E6K, E6M, E6F, E6P, E6S, E6T, E6W, E6Y, and E6V. In certain other embodiments, the at least one amino acid substitution is at the position corresponding to position 30 of SEQ ID NO: 8, and is selected from the group consisting of E30A, E30R, E30N, E30D, E30C, E30Q, E30G, E30H, E30L, E30K, E30M, E30S, E30T, E30W, E30Y, and E30V. In yet other embodiments, the at least one amino acid substitution is at the position corresponding to position 32 of SEQ ID NO: 8, and is selected from the group consisting of A32R, A32N, A32C, A32Q, A32G, A32H, A32I, A32L, A32K, A32M, A32F, A32P, A32S, A32T, A32W, A32Y, and A32V.

In certain other embodiments, the propeptide region comprises the sequence set forth in SEQ ID NO: 8, with the proviso that the propeptide region comprises at least one amino acid substitution at positions chosen from positions 6, 30 and 32 of SEQ ID NO: 8. In other embodiments, the propeptide region comprises an amino acid substitution at position 6 of SEQ ID NO: 8 selected from the group consisting of E6A, E6C, E6R, E6N, E6Q, E6G, E6H, E6I, E6L, E6K, E6M, E6F, E6P, E6S, E6T, E6W, E6Y, and E6V. In another embodiment, the propeptide region comprises an amino acid substitution at position 30 of SEQ ID NO: 8 selected from the group consisting of E30A, E30R, E30N, E30D, E30C, E30Q, E30G, E30H, E30L, E30K, E30M, E30S, E30T, E30W, E30Y, and E30V. In certain other embodiments, the propeptide region comprises an amino acid substitution at position 32 of SEQ ID NO: 8 selected from the group consisting of A32R, A32N, A32C, A32Q, A32G, A32H, A32I, A32L, A32K, A32M, A32F, A32P, A32S, A32T, A32W, A32Y, and A32V.

In other embodiments, the disclosure is directed to a polypeptide comprising a modified protease, wherein the modified protease comprises a variant propeptide region of a first *Bacillus gibsonii*-clade protease operably linked to the mature region of a second *Bacillus gibsonii*-clade protease. In certain embodiments, the first *Bacillus gibsonii*-clade protease or the second *Bacillus gibsonii*-clade protease is a serine protease or subtilisin. In certain other embodiments, the first *Bacillus gibsonii*-clade protease and the second *Bacillus gibsonii*-clade protease are from the same *Bacillus* species. In another embodiment, the first *Bacillus gibsonii*-clade protease and the second *Bacillus gibsonii*-clade protease are from different *Bacillus* species. In certain other embodiments, the variant propeptide region comprises an amino acid sequence with at least 60% identity to SEQ ID NO: 7. In yet other embodiments, the variant propeptide region comprises an amino acid sequence with at least % identity to SEQ ID NO: 7. In other embodiments, the variant propeptide region comprises the propeptide region set forth in SEQ ID NO: 7, with the proviso that the propeptide region comprises an amino acid substitution at position 34 of SEQ ID NO: 7. In certain embodiments, the amino acid substitution enhances the production of the mature region of the second *Bacillus gibsonii*-clade protease by a *Bacillus* sp. host cell. In other embodiments, the *Bacillus* species host cell is *Bacillus subtilis*. The polypeptide of claim [0255], wherein said amino acid substitution at position 34 of SEQ ID NO: 7 is selected from the group consisting of E34D, E34C, E34G, E34H, E34S, and E34V. In another embodiment, the heterologous or variant propeptide region comprises an amino acid sequence set forth in SEQ ID NO: 44. In certain other embodiments, the heterologous or variant propeptide region comprises an amino acid sequence set forth in SEQ ID NO: 69. In yet other embodiments, the polypeptide further comprises a signal peptide. In other embodiments, the disclosure is directed to polynucleotides encoding the polypeptides of the disclosure.

BRIEF DESCRIPTION OF THE DRAWINGS

FIG. 8 shows a CLUSTAL 2.0.10 multiple sequence alignment of *B. gibsonii* Bgi02446 wildtype (SEQ ID NO: 59) and the *B. lentus* P29600 wildtype (SEQ ID NO: 60) propeptides plus the N-terminal four amino acids of the respective mature regions (shown in bold).

FIG. 9 shows an alignment of nucleic acid sequences encoding the wild-type propeptide region of subtilisins from *B. gibsonii* (Bgi02446) and *B. lentus* (P29600). The alignment was performed with the CLUSTAL X 1.81 algorithm.

FIG. 10 shows an alignment of the amino acid sequences of the wild-type propeptide region of serine proteases (subtilisins) from various *Bacillus* species. The alignment was performed with the Clustal W algorithm.

FIG. 11 shows a *Bacillus* propeptide sequence motif built from analysis of multiple sequence alignment shown on FIG. 10.

FIG. 12 shows a *Bacillus* propeptide sequence motif built from analysis of sequence alignment of propeptides from *B clausii*, *B lehensis*, BspAL03240, and *B. lentus* as shown in FIG. 10.

DESCRIPTION OF THE INVENTION

Figure 1:
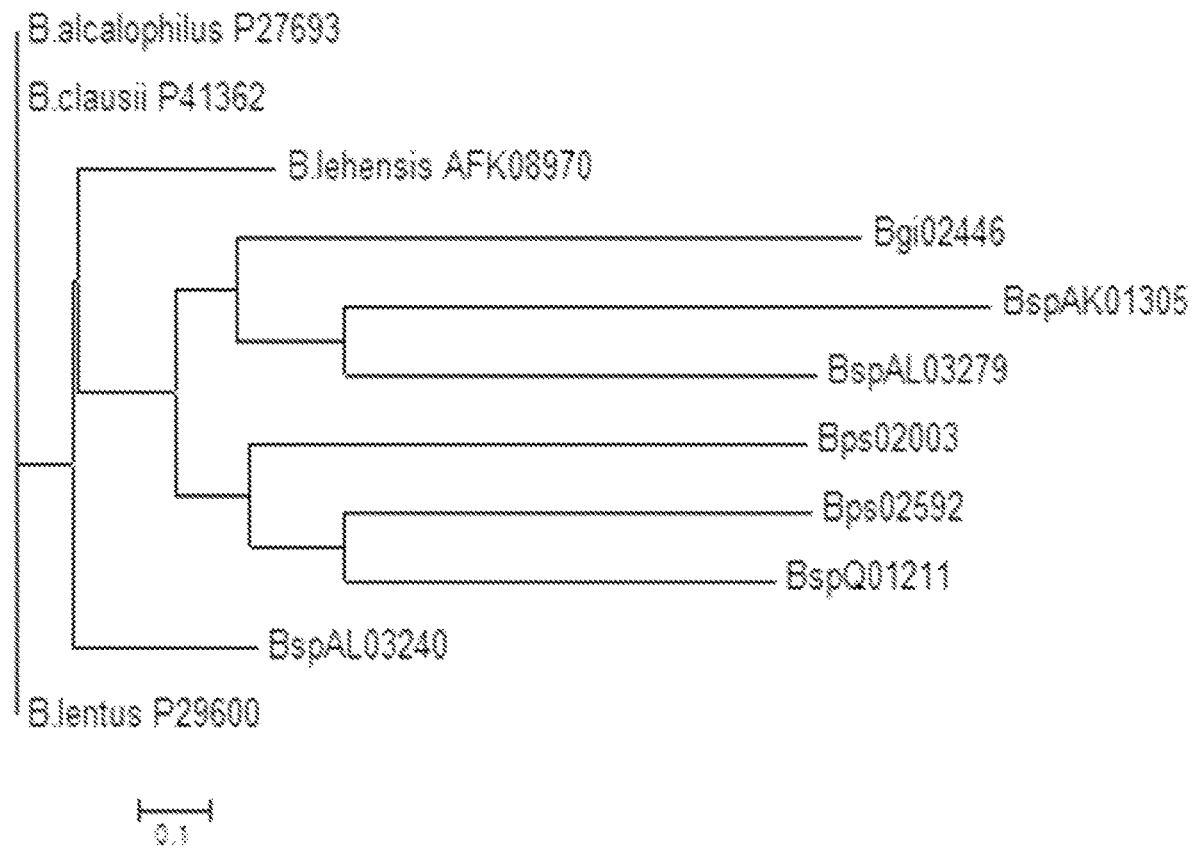
FIG. 1 depicts a phylogenetic tree of selected *Bacillus* species propeptide sequences created using the Neighbor Joining method.

The present disclosure provides modified *Bacillus* proteases, polynucleotides encoding modified *Bacillus* proteases, polypeptides comprising modified *Bacillus* proteases, and methods for enhancing the production of *Bacillus* proteases in microorganisms. In particular, the modified proteases comprise modified propeptide regions which include heterologous *Bacillus* protease propeptides in place of native propeptides of the *Bacillus* proteases to be expressed, or variant propeptides of the *Bacillus* proteases to be expressed. The polynucleotides encode heterologous *Bacillus* protease propeptides or variant propeptides linked to mature protease sequences. Such modifications of proteases or polynucleotides encoding proteases resulted in surprising and enhanced protease production levels. The present invention further relates to methods for altering the expression of proteases in microorganisms, such as *Bacillus* species.

Unless defined otherwise herein, all technical and scientific terms used herein have the same meaning as commonly understood by one of ordinary skill in the art to which this invention pertains (e.g. Singleton and Sainsbury, Dictionary of Microbiology and Molecular Biology, 2d Ed., John Wiley and Sons, NY, 1994; and Hale and Markham, The Harper Collins Dictionary of Biology, Harper Perennial, NY, 1991). Although any methods and materials similar or equivalent to those described herein find use in the practice of the present invention, the preferred methods and materials are described herein. Accordingly, the terms defined immediately below are more fully described by reference to the Specification as a whole. Also, as used herein, the singular "a", "an" and "the" includes the plural reference unless the context clearly indicates otherwise. Numeric ranges are inclusive of the numbers defining the range. Unless otherwise indicated, nucleic acids are written left to right in 5' to 3' orientation; amino acid sequences are written left to right in amino to carboxy orientation, respectively. It is to be understood that this invention is not limited to the particular methodology, protocols, and reagents described, as these may vary, depending upon the context they are used by those of skill in the art.

It is intended that every maximum numerical limitation given throughout this specification include every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

All patents, patent applications, articles and publications mentioned herein, both supra and infra, are hereby expressly incorporated herein by reference.

Furthermore, the headings provided herein are not limitations of the various aspects or embodiments of the invention which can be had by reference to the specification as a whole. Accordingly, the terms defined immediately below are more fully defined by reference to the specification as a whole. Nonetheless, in order to facilitate understanding of the invention, a number of terms are defined below.

Definitions

As used herein, the terms "isolated" and "purified" refer to a nucleic acid or amino acid (or other component) that is removed from at least one component with which it is naturally associated. In some embodiments of the invention, the polynucleotide or the polypeptide is isolated or purified. In other embodiments, the polynucleotide or the polypeptide is not isolated or purified. In some instances, the polynucleotide or the polypeptide is produced by genetic engineering, gene modification, protein engineering, protein modification, or other means so that it is different from naturally occurring polynucleotide or polypeptide but is associated with at least one component with which it is naturally associated.

The term "modified polynucleotide" herein refers to a polynucleotide sequence that has been altered to contain at least one mutation to encode a "modified" protein. In some instances, the term "polynucleotide" is used without association with "modified", which does not exclude the embodiments of polynucleotides that are modified.

As used herein, the terms "protease" and "proteolytic activity" refer to a protein or peptide exhibiting the ability to hydrolyze peptides or substrates having peptide linkages. Many well known procedures exist for measuring proteolytic activity (Kalisz, "Microbial Proteinases", In: Fiechter (ed.), *Advances in Biochemical Engineering/Biotechnology*, 1988). For example, proteolytic activity may be ascertained by comparative assays which analyze the produced protease's ability to hydrolyze a commercial substrate. Exemplary substrates useful in such analysis of protease or proteolytic activity, include, but are not limited to dimethyl casein (Sigma C-9801), bovine collagen (Sigma C-9879), bovine elastin (Sigma E-1625), and bovine keratin (ICN Biomedical 902111). Colorimetric assays utilizing these substrates are well known in the art (see e.g., WO 99/34011; and U.S. Pat. No. 6,376,450, both of which are incorporated herein by reference). The AAPF assay (see e.g., Del Mar et al., *Anal. Biochem.,* 99:316-320, 1979, or Estell et al., *J Biol Chem.,* 260:6518-6521, 1985) also finds use in determining the production of mature protease. This assay measures the rate at which p-nitroaniline is released as the enzyme hydrolyzes the soluble synthetic substrate, succinyl-alanine-alanine-proline-phenylalanine-p-nitroanilide (sAAPF-pNA). The rate of production of yellow color from the hydrolysis reaction is measured at 410 nm or 405 nm on a spectrophotometer and is proportional to the active enzyme concentration. In particular, the term "protease" herein refers to a "serine protease".

As used herein, the terms "subtilisin" and "serine protease" refer to any member of the S8 serine protease family as described in MEROPS—The Peptidase Data base (Rawlings et al., MEROPS: the peptidase database, Nucleic Acids Res, 34 Database issue, D270-272, 2006, at the website merops.sangerac.uk/cgi-bin/merops.cgi?id=s08;action=.). The following information was derived from MEROPS—The Peptidase Data base as of Nov. 6, 2008 "Peptidase family S8 contains the serine endopeptidase serine protease and its homologues (*Biochem J,* 290:205-218, 1993). Family S8, also known as the subtilase family, is the second largest family of serine peptidases, and can be divided into two subfamilies, with subtilisin (S08.001) the type-example for subfamily S8A and kexin (S08.070) the type-example for subfamily S8B. Tripeptidyl-peptidase II (TPP-II; S08.090) was formerly considered to be the type-example of a third subfamily, but has since been determined to be misclassified.

The term "parent protease" herein refers to a full-length protease comprising pre, pro and mature regions that are naturally expressed in combination. In some embodiments, the pre and/or pro and/or mature regions of a parent protease serve to originate the pre and/or pro and/or mature regions of a precursor protease.

The term "precursor protease" herein refers to an unmodified or modified full-length protease comprising a signal peptide, a pro (or propeptide) region and a mature region. The precursor protease can be derived from naturally-occurring (i.e. wild-type) proteases, from variant proteases, modified proteases, or mutated proteases. In some embodiments of the invention, it is the pro region of a precursor protease that is modified to generate a modified protease. In some embodiments, the pre region of a precursor protease is modified. In some embodiments, the precursor protease comprises a pro region and a mature region that are derived from one parent protease. In other embodiments, the precursor protease is a chimeric protein that comprises a pre or pro region that is derived from one or more parent protease and a mature region that is derived from a different parent protease.

The term "chimeric" or "fusion" when used in reference to a protein, herein refer to a protein created through the joining of two or more polynucleotides which originally coded for separate proteins or protein fragments. Translation of this fusion polynucleotide results in a single chimeric polypeptide with functional properties derived from each of the original proteins. Recombinant fusion proteins can be produced by recombinant DNA technology and expression of fusion/chimeric polynucleotide. Recombinant fusion proteins can also be generated by in vitro chemical synthesis. A "chimeric polypeptide," or "chimera" means a protein containing sequences from more than one polypeptide. A modified protease can be chimeric in the sense that it contains a portion, region, or domain from one protease fused to one or more portions, regions, or domains from one or more other protease. By way of example, a chimeric protease might comprise the mature region of one protease linked to the pro peptide of another protease. The skilled artisan will appreciate that chimeric polypeptides and proteases need not be made by actual fusions of the protein sequences, but rather, polynucleotides with the corresponding encoding sequences can also be used to express chimeric polypeptides or proteases.

"Naturally-occurring" or "wild-type" herein refer to a protease having the unmodified amino acid sequence identical to that found in nature, or a polynucleotide encoding such a protease. Naturally occurring enzymes include native enzymes, those enzymes naturally expressed or found in the particular microorganism. A sequence that is wild-type or naturally-occurring refers to a sequence that is identical to or derived from that found in nature. A wild-type sequence may comprise or encode the sequence of a variant, a homolog or a heterolog that occurs in nature which is not identical to the sequence of the first-identified polynucleotide or polypeptide. A polynucleotide encoding a naturally-occurring or wild-type protease can be a naturally-occurring or wild-type polynucleotide itself, or can be a modified polynucleotide that encodes a protein sequence that is identical to the naturally-occurring or wild-type polypeptide.

As used herein, a "variant" protein or protein region refers to a protein or protein region which differs from its corresponding wild-type protein or protein region by addition of one or more amino acids to either or both the C- and N-terminal end, substitution of one or more amino acids at one or a number of different sites in the amino acid sequence, deletion of one or more amino acids at either or both ends of the protein or at one or more sites in the amino acid sequence, and/or insertion of one or more amino acids at one or more sites in the amino acid sequence of the protein. Variant proteins encompass naturally-occurring variants and genetically engineered variant proteins. A variant protein in the context of the present invention refers to non-naturally-occurring variants and is exemplified by the *B. gibsonii* subtilisin BSP-00801 which is a variant of the naturally-occurring protein *B. gibsonii* subtilisin Bgi02446. Sequences of two forms of the mature region of BSP-00801 are shown in SEQ ID NO: 12 and SEQ ID NO: 13, while those of Bgi02446 are shown in SEQ ID NO: 10 and SEQ ID NO: 11. SEQ ID NOs:12 and 13 differ from SEQ ID NOs:11 and 10, respectively, by ten amino acid substitutions.

As used herein, "homolog" and "homologous protein" refers to a protein (e.g., protease) that has similar action and/or structure, as a protein of interest (e.g., a protease from another source). It is not intended that homologs be necessarily related evolutionarily. Thus, it is intended that the term encompass the same or similar enzyme(s) (i.e., in terms of structure and function) obtained from different species.

The terms "derived from" and "obtained from" refer to not only a protease produced or producible by a strain of the organism in question, but also a protease encoded by a DNA sequence isolated from such strain and produced in a host organism containing such DNA sequence. Additionally, the term refers to a protease which is encoded by a DNA sequence of synthetic and/or cDNA origin and which has the identifying characteristics of the protease in question. To exemplify, "proteases derived from *Bacillus*" refers to those enzymes having proteolytic activity which are naturally-produced by *Bacillus*, as well as to serine proteases like those produced by *Bacillus* sources but which through the use of genetic engineering techniques are produced by non-*Bacillus* organisms transformed with a nucleic acid encoding said serine proteases.

A "modified full-length protease" and "modified precursor protease" are interchangeably used to refer to a full-length protease that comprises a signal peptide, a pro (or propeptide) region, and a mature region that are derived from one or more parent or precursor protease, wherein the pro region or the pre region, or both, is modified to contain at least one modification or mutation. The term "modified protease" as used herein, on the other hand, refers to a full-length or partial protease with at least a pro region and a mature region derived from one or more parent protease, wherein the pro region is modified to contain at least one modification or mutation. In some embodiments, the pro region and the mature region are derived from the same parent protease. In other embodiments, the pro region and the mature region are derived from different parent proteases. The modified protease comprises a pro region that is modified to contain the pro region of a heterologous protease, or contain the pro region of the same parent protease but with at least one mutation. A modified protease is encoded by a modified polynucleotide which is not wild-type, at least not wild-type over the entire length of the protease-encoding gene. The amino acid sequence of the modified protease is said to be "generated" from the parent protease amino acid sequence by introducing into the pro region of the parent amino acid sequence at least one mutation e.g. a substitution, deletion or insertion of one or more amino acids, or by replacing the pro region of the entire parent amino acid sequence with the pro region of a heterologous protease. In some embodiments, one or more amino acids of the pro region of the precursor protease are substituted to generate the modified full-length protease. Such modification is of the "precursor" DNA sequence which encodes the amino acid sequence of the "precursor" protease rather than manipulation of the precursor protease per se. For example, a modified full-length protease is represented by SEQ ID NO: 58, which includes the signal peptide of *B. subtilis* subtilisin AprE, the propeptide sequence of the wild-type *B. lentus* subtilisin P29600, and the mature sequence of *B. gibsonii* subtilisin variant BSP-00801. A DNA sequence that encodes the modified full-length protease of SEQ ID NO: 58 is shown in SEQ ID NO:14.

The term "unmodified" when used in reference to a protease polypeptide or polynucleotide, herein refers to a protease comprising a pro region that has not been modified to comprise at least one mutation e.g. a substitution.

The terms "full-length protein" and "pre-pro-protein" herein refer to a gene product comprising a signal peptide, a pro sequence and a mature sequence.

The term "signal sequence", "signal peptide" or "pre region" refers to any sequence of nucleotides and/or amino acids which may participate in the secretion of the mature or precursor forms of the protein. This definition of signal sequence is a functional one, meant to include all those amino acid sequences encoded by the N-terminal portion of the protein gene, which participate in the effectuation of the secretion of protein. To exemplify, a pre peptide of a protease of the present invention at least includes the amino acid sequence of SEQ ID NO: 40, which corresponds to amino acids 1-29 of the full-length protease of SEQ ID NO: 58.

As presented below, SEQ ID NO: 58 comprises the amino acid sequence of a modified full-length protease, wherein the underlined amino acid residues comprise an AprE signal peptide (i.e., residues 1-29 of SEQ ID NO: 58), the italicized amino acid residues comprise a B. lentus_P29600 PRO peptide (i.e., residues 30-113 of SEQ ID NO: 58), and the capitalized amino acid residues comprise the mature BSP-00801 variant protease (i.e., residues 114-382 of SEQ ID NO: 58).

(SEQ ID NO: 58)
vrskklwisllfaltliftmafsnmsaqa*aeeeakekyligfneqeavsef*

*veqveandevailseeeeveiellhefetipvlsvelspedvdaleldpa*

*isyieedaevttm*QQTVPWGITRVQAPAVHNRGITGSGVRVAILDSGIST

HEDLNVRGGVSFVPGEPTTADLNGHGTHVAGTVAALNNSIGVVGVAPSAD

LYAVKVLGANGRGSVSGIAQGLEWAAANNMHIANMSLGSDAPSSTLERAV

NYATSRDVLVIAATGNNGSGSVGYPARYANAMAVGATDQNNRRANFSQYG

TGIDIVAPGVNVQSTYPGNRYVSMNGTSMATPHVAGAAALVKQRYPSWNA

TQIRNHLKNTATNLGNSSQFGSGLVNAEAATR

The term "pro sequence", "pro region", "propeptide", "propeptide sequence", or "propeptide region", is an amino acid sequence between the signal sequence and mature protease that is necessary for folding, secretion, and/or production of the protease. Cleavage of the pro sequence from a pro-protease will result in a mature active protease. To exemplify, a pro region of a protease of the present invention includes at least the amino acid sequence of SEQ ID NO: 8, which corresponds to amino acids 30-113 of the full-length protease of SEQ ID NO: 58.

A "heterologous propeptide region" as used herein refers to a propeptide region that is not native to, or not originally expressed as part of the same precursor protease as, the mature protease of interest. A heterologous propeptide region, or the propeptide region of a heterologous protease, has at least one amino acid difference from the native propeptide region of the mature protease of interest.

The term "mature form" or "mature region" of a protease refers to the final functional portion of the protease. To exemplify, a mature form of the protease of the present invention includes the amino acid sequence of SEQ ID NO: 12 or 13, which corresponds to amino acids 114-382 or 115-382 of the full-length protease of SEQ ID NO: 58, respectively. In this context, the "mature form" is "processed from" a full-length protease, wherein the processing of the full-length protease encompasses the removal of the signal peptide and the removal of the pro region.

The terms "pro-protein", "pro-polypeptide" and "pro-protease", herein refer to a protein comprising the mature form operably linked to a pro-polypeptide. A "pro-polypeptide" is encoded by a "pro-polynucleotide".

As used herein, the term "heterologous protein", as opposed to a native protein, for example, refers to a protein or polypeptide that does not naturally occur in the same host cell or host strain as the native protein does. Similarly, a "heterologous polynucleotide" refers to a polynucleotide that does not naturally occur in the same host cell or host strain as a native polynucleotide does. Heterologous polypeptides and/or heterologous polynucleotides include full-length or partial wild-type polypeptides and/or polynucleotides that naturally occur in a host cell or host strain that is different from the host cell or host strain where the native polypeptides and/or heterologous polynucleotides occur. They also include full-length or partial polypeptides and/or polynucleotides that do not naturally occur in any known natural host cell or host strain, e.g., genetically engineered polypeptides and/or polynucleotides. They include full-length, partial, or chimeric polypeptides and/or polynucleotides. A heterologous protein can be a protein that has the same, similar, or equivalent function and/or structure as the native protein does, or it can be a protein with very different function and/or structure. A heterologous protein has at least one different amino acid from the native protein.

As used herein, "substituted" and "substitutions" refer to replacement(s) of an amino acid residue or nucleic acid base in a parent sequence. In some embodiments, the substitution involves the replacement of a naturally occurring residue or base. The modified proteases herein encompass the substitution of any one of all the amino acids in the pro region of the precursor protease by any one of the remaining 19 amino acids naturally occurring in bacteria, or by a non-naturally occurring amino acid.

For example, the substitution of the glutamic acid at position 6 (abbreviated as "E6") of the wild-type B. lentus subtilisin P29600 sequence, SEQ ID NO: 8, can be substituted/replaced with any one of the group consisting of alanine (A), cysteine (C), aspartic acid (D), glycine (G), phenylalanine (F), histidine (H), isoleucine (I), lysine (K), leucine (L), methionine (M), asparagine (N), proline (P), glutamine (Q), arginine (R), serine (S), threonine (T), valine (V), thryptophan (W), and tyrosine (Y). A substitution of an amino acid (e.g. E6) for any other amino acid at the same position is denoted by E6X, wherein X is one of the remaining 19 amino acids that substitutes E at position 6. In some embodiments, two or more amino acids are substituted to generate a modified protease that comprises a combination of amino acid substitutions. For example, a combination of a substitution of amino acid E at position 6 for amino acid A in combination with the substitution of amino acid E at position 30 for amino acid T is denoted as E6A-E30T. In some embodiments, amino acid positions for the substitutions in the pro region are numbered corresponding to the numbered position in the pro region of SEQ ID NO:8. In some other embodiments, amino acid positions for the substitutions in the pro region are numbered corresponding to the numbered position in the pro region of SEQ ID NO:7.

As used herein, "by correspondence to", "corresponding to," or "equivalent to" refers to a residue at the enumerated position in a protein or peptide, or a residue that is analogous, homologous, or equivalent to an enumerated residue in a protein or peptide. As used herein, "corresponding region," generally refers to an analogous position along related proteins or a reference protein. The native amino acid in a protein at a position corresponding to an enumerated residue in a reference protein can be the same as or different from the residue in the reference protein.

The terms "pre polynucleotide", "pro nucleotide" and "mature polynucleotide" herein refer to the polynucleotide sequences that respectively encode for the pre, pro and mature regions of a protein e.g. a protease.

The term "production" with reference to a protease, encompasses the two processing steps of a full-length protease including: (1) the removal of the signal peptide, which is known to occur during protein secretion; and (2) the removal of the pro region, which creates the active mature form of the enzyme and which is known to occur during the maturation process (Wang et al., *Biochemistry* 37:3165-3171, 1998; Power et al., *Proc Natl Acad Sci USA* 83:3096-3100, 1986). The term "enhanced production" herein refers to the production of a mature protease that is processed from a modified full-length protease, and which occurs at a level that is greater than the level of production of the same mature protease when processed from an unmodified full-length protease.

The term "processed" with reference to a mature protease refers to the maturation process that a full-length protein e.g. a full-length protease, undergoes to become an active mature enzyme.

"Activity" with respect to enzymes means "catalytic activity" and encompasses any acceptable measure of enzyme activity, such as the rate of activity, the amount of activity, or the specific activity. Catalytic activity refers to the ability to catalyze a specific chemical reaction, such as the hydrolysis of a specific chemical bond. As the skilled artisan will appreciate, the catalytic activity of an enzyme only accelerates the rate of an otherwise slow chemical reaction. Because the enzyme only acts as a catalyst, it is neither produced nor consumed by the reaction itself. The skilled artisan will also appreciate that not all polypeptides have a catalytic activity. "Specific activity" is a measure of activity of an enzyme per unit of total protein or enzyme. Thus, specific activity may be expressed by unit weight (e.g. per gram, or per milligram) or unit volume (e.g. per ml) of enzyme. Further, specific activity may include a measure of purity of the enzyme, or can provide an indication of purity, for example, where a standard of activity is known, or available for comparison. The amount of activity reflects to the amount of enzyme that is produced by the host cell that expresses the enzyme being measured.

The term "relative activity" or "ratio of production" are used herein interchangeably to refer to the ratio of the enzymatic activity of a mature protease that was processed from a modified protease to the enzymatic activity of a mature protease that was processed from an unmodified protease. The ratio of production is determined by dividing the value of the activity of the protease processed from a modified precursor by the value of the activity of the same protease when processed from an unmodified precursor. The relative activity is the ratio of production expressed as a percentage.

As used herein, the term "expression" refers to the process by which a polypeptide is produced based on the nucleic acid sequence of a gene. The process includes both transcription and translation.

The term "percent (%) identity" is defined as the percentage of amino acid/nucleotide residues in a candidate sequence that are identical with the amino acid residues/nucleotide residues of the precursor sequence (i.e., the parent sequence). A % amino acid sequence identity value is determined by the number of matching identical residues divided by the total number of residues of the "longer" sequence in the aligned region. Amino acid sequences may be similar, but are not "identical" where an amino acid is substituted, deleted, or inserted in the subject sequence relative to the reference sequence. For proteins, the percent sequence identity is preferably measured between sequences that are in a similar state with respect to posttranslational modification. Typically, the "mature sequence" of the subject protein, i.e., that sequence which remains after processing to remove a signal sequence, is compared to a mature sequence of the reference protein. In other instances, a precursor sequence of a subject polypeptide sequence may be compared to the precursor of the reference sequence.

As used herein, the term "promoter" refers to a nucleic acid sequence that functions to direct transcription of a downstream gene. In some embodiments, the promoter is appropriate to the host cell in which the target gene is being expressed. The promoter, together with other transcriptional and translational regulatory nucleic acid sequences (also termed "control sequences") is necessary to express a given gene. In general, the transcriptional and translational regulatory sequences include, but are not limited to, promoter sequences, ribosomal binding sites, transcriptional start and stop sequences, translational start and stop sequences, and enhancer or activator sequences.

A nucleic acid or a polypeptide is "operably linked" when it is placed into a functional relationship with another nucleic acid or polypeptide sequence, respectively. For example, a promoter or enhancer is operably linked to a coding sequence if it affects the transcription of the sequence; a ribosome binding site is operably linked to a coding sequence if it is positioned so as to facilitate translation; or a modified or heterologous pro region is operably linked to a mature region of a protease if it enables the processing of the full-length protease to produce the mature active form of the enzyme. Generally, "operably linked" means that the DNA or polypeptide sequences being linked are contiguous. In some instances, "operably linked" encompasses indirect linking.

A "host cell" refers to a suitable cell that serves as a host for an expression vector comprising DNA according to the present invention. A suitable host cell may be a naturally occurring or wild-type host cell, or it may be an altered host cell. In one embodiment, the host cell is a Gram positive microorganism. In some embodiments, the term refers to cells in the genus *Bacillus*.

As used herein, "*Bacillus* sp." includes all species within the genus "*Bacillus*," as known to those of skill in the art, including but not limited to *B. subtilis, B. licheniformis, B. lentus, B. gibsonii, B. clausii, B. novalis, B. brevis, B. pumilis, B. stearothermophilus, B. alkalophilus, B. amyloliquefaciens, B. halodurans, B. megaterium, B. coagulans, B. circulans, B. lautus*, and *B. thuringiensis*. It is recognized that the genus *Bacillus* continues to undergo taxonomical reorganization. Thus, it is intended that the genus include species that have been reclassified, including but not limited to such organisms as *B. stearothermophilus*, which is now named "*Geobacillus stearothermophilus*." The production of resistant endospores in the presence of oxygen is considered the defining feature of the genus *Bacillus*, although this characteristic also applies to the recently named *Alicyclobacillus, Amphibacillus, Aneurinibacillus, Anoxybacillus, Brevibacillus, Filobacillus, Gracilibacillus, Halobacillus, Paenibacillus, Salibacillus, Thermobacillus, Ureibacillus*, and *Virgibacillus*.

The terms "polynucleotide" and "nucleic acid", used interchangeably herein, refer to a polymeric form of nucleotides of any length. These terms include, but are not limited to, a single stranded DNA, double-stranded DNA, genomic DNA, cDNA, or a polymer comprising purine and pyrimidine bases, or other natural, chemically, biochemically modified, non-natural or derivatized nucleotide bases. Non-limiting examples of polynucleotides include genes, gene fragments, chromosomal fragments, ESTs, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. It will be understood that, as a result of the degeneracy of the genetic code, a multitude of nucleotide sequences encoding a given protein may be produced.

As used herein, the terms "DNA construct" and "transforming DNA" are used interchangeably to refer to DNA used to introduce sequences into a host cell or organism. The DNA construct may be generated in vitro by PCR or any other suitable technique(s) known to those in the art. In some embodiments, the DNA construct comprises a sequence of interest (e.g., a sequence encoding a modified protease). In some embodiments, the sequence is operably linked to additional elements such as control elements (e.g., promoters, etc.). The DNA construct may further comprise a selectable marker. In some embodiments, the DNA construct comprises sequences homologous to the host cell chromosome. In other embodiments, the DNA construct comprises non-homologous sequences. Once the DNA construct is assembled in vitro it may be used to mutagenize a region of the host cell chromosome (i.e., replace an endogenous sequence with a heterologous sequence).

As used herein, the term "expression cassette" refers to a nucleic acid construct generated recombinantly or synthetically, with a series of specified nucleic acid elements that permit transcription of a particular nucleic acid in a target cell. The recombinant expression cassette can be incorporated into a vector such as a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter. In some embodiments, expression vectors have the ability to incorporate and express heterologous DNA fragments in a host cell. Many prokaryotic and eukaryotic expression vectors are commercially available. Selection of appropriate expression vectors is within the knowledge of those of skill in the art. The term "expression cassette" is used interchangeably herein with "DNA construct," and their grammatical equivalents. Selection of appropriate expression vectors is within the knowledge of those of skill in the art.

As used herein, the term "heterologous DNA sequence" refers to a DNA sequence that does not naturally occur in a host cell. In some embodiments, a heterologous DNA sequence is a chimeric DNA sequence that is comprised of parts of different genes, including regulatory elements.

As used herein, the term "vector" refers to a polynucleotide construct designed to introduce nucleic acids into one or more cell types. Vectors include cloning vectors, expression vectors, shuttle vectors, and plasmids. In some embodiments, the polynucleotide construct comprises a DNA sequence encoding the full-length protease (e.g., modified protease or unmodified precursor protease). As used herein, the term "plasmid" refers to a circular double-stranded (ds) DNA construct used as a cloning vector, and which forms an extrachromosomal self-replicating genetic element in some eukaryotes or prokaryotes, or integrates into the host chromosome.

As used herein in the context of introducing a nucleic acid sequence into a cell, the term "introduced" refers to any method suitable for transferring the nucleic acid sequence into the cell. Such methods for introduction include but are not limited to protoplast fusion, transfection, transformation, conjugation, and transduction (see e.g., Ferrari et al., "Genetics," in Hardwood et al., (eds.), *Bacillus*, Plenum Publishing Corp., pages 57-72, 1989).

As used herein, the terms "transformed" and "stably transformed" refers to a cell that has a non-native (heterologous) polynucleotide sequence integrated into its genome or as an episomal plasmid that is maintained for at least two generations.

Modified Proteases

The present invention provides methods and compositions for the production of mature proteases in bacterial host cells. The compositions include polynucleotides that encode modified proteases which have a heterologous pro region or at least one mutation in the native pro region of the protease to be produced; the modified serine proteases encoded by the such polynucleotides; expression cassettes, DNA constructs, vectors, and chromosomes comprising the polynucleotides that encode the modified proteases; and the bacterial host cells transformed with the vectors or comprising the chromosomes of the invention. The methods include methods for enhancing the production of mature proteases in bacterial host cells e.g. *Bacillus* sp. host cells. The produced proteases find use in the industrial production of enzymes, suitable for use in various industries, including but not limited to the cleaning, animal feed and textile processing industry.

The basic mechanism by which proteins are transported across membranes appears to be universal, with important features conserved between bacteria and eukaryotes. Because they can secrete certain proteins in large quantities into the growth medium, *Bacillus* species are used for the industrial production of enzymes such as alkaline serine proteases. Proteases are produced in vivo from a precursor protease known as a pre-pro-protease, which comprises a pre region, also known as signal peptide, a pro region and a mature region of the protease. Protein secretion across the *Bacillus* sp. cell envelope is a complex process that includes insertion of the precursor protein into the membrane and translocation of the protein across the membrane. The pre region serves as a signal peptide for protein secretion across the membrane and is hydrolyzed by a signal peptidase. The extracellular part of the maturation process involves folding of the pro-protease, self-processing of the pro region, and degradation of the pro-region to create the active mature form of the enzyme (Nagarjan V., Protein Secretion in "*Bacillus subtilis* and other Gram-Positive Bacteria" Ch. 49, p 713-726, 1993; Ruan et al., *Biochemistry*, 38:8562-8571, 2009).

In some embodiments, the modified protease is a serine protease. In some embodiments, the modified protease is an alkaline serine protease. In certain embodiments, the modified protease is a subtilisin.

In some embodiments, the invention provides a modified protease comprising the propeptide region of a heterologous *Bacillus* protease operably linked to the mature region of a *Bacillus gibsonii*-clade protease. In some embodiments, the modified protease consists essentially of or consists of the propeptide region of a heterologous *Bacillus* protease operably linked to the mature region of a *Bacillus gibsonii*-clade protease. In some embodiments, the heterologous *Bacillus* protease is from a *Bacillus* species that is not a member of the *Bacillus gibsonii*-clade. In some embodiments, the modified protease comprises a variant propeptide region of a first *Bacillus gibsonii*-clade protease linked to the mature region of a second *Bacillus gibsonii*-clade protease. In certain embodiments, the first *Bacillus gibsonii*-clade protease and said second *Bacillus gibsonii*-clade protease are from the same *Bacillus* species or the same strain. In other embodiments, first *Bacillus gibsonii*-clade protease and said second *Bacillus gibsonii*-clade protease are from different *Bacillus* species or strain.

In some embodiments, the modified protease is generated by replacing the propeptide-region-encoding nucleic acid sequence (the native pro polynucleotide) of a *Bacillus gibsonii*-clade protease (the protease to be produced) with a nucleic acid sequence encoding the propeptide region of a heterologous *Bacillus* protease (a heterologous pro polynucleotide).

Propeptide Region

In some embodiments of the modified protease of the invention, the propeptide region is a propeptide region from a heterologous *Bacillus* protease (e.g., a non-*Bacillus gibsonii*-clade protease, or a protease from a different *B. gibsonii*-clade species or a different strain of a *B. gibsonii* from the native species or strain that provides the sequence of the mature region). The propeptide region from a heterologous *Bacillus* protease has at least one amino acid difference from the native propeptide region of the protease that provides the sequence of the mature region. In some embodiments, the propeptide region is a non-naturally-occurring, variant propeptide region from a *Bacillus gibsonii*-clade protease.

Heterologous proteases from a variety of species of *Bacillus* can be used to provide or derive the sequence for the propeptide region of the modified protease in the form of amino acids or nucleotides encoding the proteins sequence. For example, serine proteases from *Bacillus lentus, Bacillus clausii, Bacillus alcalophilus, Bacillus lehensis, Bacillus novalis*, or their related species can all be used. In some embodiments, the propeptide region of the modified protease is from *B. lentus* or a related species thereof. Wild-type or variant heterologous proteases can both be used. Examples of heterologous proteases include, but are not limited to, BspQ01211, Bps02592, *B. lentus*_P29600, BspAL03240, Bpan01744, *B. clausii*_P41362, *B. lehensis*_AFK08970, Bps02003, Bohn00569, BspAK01305, Bpan04382, and BspAL03279.

For example, the propeptide sequence of *B. clausii*_P41362 is set forth in SEQ ID NO: 42, the propeptide sequence of *B. lehensis*_AFK08970 is set forth in SEQ ID NO: 43, the propeptide sequence of Bps02003 is set forth in SEQ ID NO: 48, the propeptide sequence of BspQ01211 is set forth in SEQ ID NO: 49, the propeptide sequence of Bps02592 is set forth in SEQ ID NO: 50, the propeptide sequence of *B. lentus*_P29600 is set forth in SEQ ID NO: 8, the propeptide sequence of BspAL03240 is set forth in SEQ ID NO: 51, the propeptide sequence of Bpan01744 is set forth in SEQ ID NO: 52, the propeptide sequence of Bohn00569 is set forth in SEQ ID NO: 53, the propeptide sequence of BspAK01305 is set forth in SEQ ID NO: 54, the propeptide sequence of Bpan04382 is set forth in SEQ ID NO: 55 and the propeptide sequence of BspAL03279 is set forth in SEQ ID NO: 56.

In the embodiments where *B. gibsonii*-clade propeptide regions are used (including heterologous and variant propeptide regions of *Bacillus gibsonii*-clade proteases), examples of such *Bacillus gibsonii*-clade proteases include, but are not limited to, subtilisins from *B. gibsonii* strains DSM8722 (protease named Bgi02446 or AprBG), DSM9728, DSM9729, DSM9730 and DSM9731, all of which are disclosed in International PCT Publication No. WO2015/089447 which is incorporated herein by reference. The propeptide sequences of these DSM strain serine proteases are identical.

Other examples of such *Bacillus gibsonii*-clade proteases include, but are not limited to subtilisins from *B. gibsonii* TII-5 (PCT Publication No. WO2003/054185, Derwent Patent Index Accession No. CAE48424), *B. gibsonii* TI-1 (PCT Publication No. WO2003/054184, Derwent Patent Index Accession No. CAE48421), *B. gibsonii* HP302 (PCT Publication No. WO2007/131657, Derwent Patent Index Accession No. CAS91385 and PCT Publication No. WO2008/086916, Derwent Patent Index Accession No. CAV33594).

Sequences of the propeptide regions from some of the *Bacillus gibsonii*-clade proteases described herein are set forth in SEQ ID NO: 7 (Bgi02446 propeptide), SEQ ID NO: 45 (*B. gibsonii*_TII-5 propetide), SEQ ID NO: 46 (*B. gibsonii*_HP302 propetide) and SEQ ID NO: 47 (*B. gibsonii*_TI-1 propeptide).

To compare and visualize the relationship among the propeptide region sequences from the above *Bacillus* species' subtilisin, a phylogenetic tree of representative sequences was generated and is set forth in FIG. 1. The propeptide amino acid sequences were entered in the Vector NTI Advance suite and a Guide Tree was created using the Neighbor Joining (NJ) method (Saitou and Nei, *Mol. Biol. Evol*, 4:406-425, 1987).

The NJ method works on a matrix of distances between all pairs of sequences to be analyzed. These distances are related to the degree of divergence between the sequences. The Guide Tree is calculated after the sequences are aligned. The tree construction was calculated using the following parameters: Kimura's correction for sequence distance and ignoring positions with gaps. The MEGA 6 program was used to display the phylogenetic tree. A more detailed sequence alignment created using CLUSTALW software (Thompson et al., *Nucleic Acids Research*, 22:4673-4680, 1994) with default parameters is presented and set forth below in Example 13.

In some embodiments of the modified protease, the propeptide region of the heterologous *Bacillus* protease, or the heterologous propeptide region, comprises an amino acid sequence with at least 40% identity to SEQ ID NO: 8.

In some embodiments, the propeptide region of the heterologous *Bacillus* protease, or the heterologous propeptide region, comprises an amino acid sequence with at least 42%, 44%, 46%, 48%, 50%, 52%, 54%, 56%, 58%, 60%, 62%, 64%, 66%, 68%, or 70% identity to SEQ ID NO: 8. In some embodiments, the heterologous propeptide region comprises an amino acid sequence with at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity to SEQ ID NO: 8. In some embodiments, the heterologous *Bacillus* protease's propeptide region comprises the amino acid sequence of SEQ ID NO: 8.

In some embodiments, the propeptide region of the heterologous *Bacillus* protease comprises a variant propeptide region of a subtilisin from *Bacillus lentus* or a related species thereof, wherein the variant propeptide region comprises at least one amino acid substitution. In some embodiments, the at least one amino acid substitution is at a position corresponding to position 6, 30, or 32 of SEQ ID NO: 8. In some embodiments, the at least one amino acid substitution enhances production of said mature region of the *Bacillus gibsonii*-clade protease by a *Bacillus* sp. host cell (e.g., a *Bacillus subtilis* host cell).

In some embodiments, the at least one amino acid substitution enhances production of said mature region of the *Bacillus gibsonii*-clade protease as compared to a polynucleotide comprising the same first polynucleotide region and third polynucleotide region but a second polynucleotide region encoding a wild-type propeptide region of the same subtilisin.

In some embodiments, the propeptide region comprises a variant propeptide region of a *Bacillus gibsonii*-clade protease with at least 60% identity to SEQ ID NO: 7. In some embodiments, the variant propeptide region comprises an amino acid sequence with at least 62%, 64%, 66%, 68%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, or 98% identity to SEQ ID NO: 7.

In some embodiments, the variant propeptide region of a *Bacillus gibsonii*-clade protease comprises an amino acid substitution at a position corresponding to position 34 of SEQ ID NO: 7. In some embodiments, the amino acid substitution enhances production of the mature region of the *Bacillus gibsonii*-clade protease linked to the propeptide by a *Bacillus* sp. host cell (e.g., a *Bacillus subtilis* host cell).

In some embodiments, the propeptide region of the heterologous or variant propeptide region comprises an amino acid sequence set forth in SEQ ID NO: 44 (which is shown in FIG. 11 and further described in Example 13. In some embodiments, each "X" can be any amino acid. In some embodiments, the "X's" at positions 1, 22-51, and 91 can be absent individually or collectively. In specific embodiments, the amino acids "Xs" in SEQ ID NO: 44 can be selected from possible amino acids as set forth below in Table 1.

TABLE 1

| Position | Amino Acid |
|---|---|
| 1 | A or absent |
| 2 | A, E, or D |
| 4 | I, Q, A, E, or T |
| 6 | V, E, or K |
| 13 | H, K, T, N, E or D |
| 14 | N, A, or E |
| 15 | P, E, Q |
| 16 | L, V, A, E, or Q |
| 17 | D, Q, S, V, A, or E |
| 18 | M, L, or V |
| 19 | N, T, S, or E |
| 20 | E, A, T, or Q |
| 22 | T, V, L, or I |
| 23 | T, N, E, or D |
| 24 | N, M, E, Q, S, or A |
| 25 | L, V, I, S, T, or D |
| 26 | E, D, or V |
| 27 | E, S, Q, A, G, K, T, or absent |
| 28 | E, V, N, G, or absent |
| 29 | I, G, D, E, K, N, or T |
| 30 | R, A, V, E, D, or N |
| 31 | T, A, F, V, E, Y, Q, or G |
| 32 | Q, L, S, A, V, or F |

TABLE 1-continued

| Position | Amino Acid |
| --- | --- |
| 33 | A, S, V, I, or Q |
| 34 | D, E, L, I, or S |
| 35 | D, E, S, F, or Y |
| 36 | A, E, Q, T, or absent |
| 37 | S, E, V, A, or absent |
| 38 | V, A, S, or absent |
| 39 | A, E, or absent |
| 40 | E, I, V, D, or absent |
| 41 | D, N, K, or absent |
| 42 | T, D, N, S, or absent |
| 43 | L, E, D, A, or absent |
| 44 | D, E, T, Q, or absent |
| 45 | I, V, or absent |
| 46 | D, E, Q, or absent |
| 47 | I, V, M, or L |
| 48 | D or E |
| 49 | V, I, or L |
| 50 | T, I, or L |
| 51 | Y, D, or H |
| 53 | F or Y |
| 54 | K, D, or E |
| 55 | D, E, Y, T, F, or Q |
| 64 | T, S, D, or N |
| 72 | K, L, S, or E |
| 73 | N, E, L, G, K, or A |
| 74 | E or D |
| 75 | E, P, A, or S |
| 76 | S, A, or G |
| 80 | I or V |
| 85 | Q, I, A, V, or F |
| 87 | V or L |
| 88 | T, S, or K |
| 89 | T or I |
| 90 | M, F, A, or absent |
| 91 | A or absent |

In other embodiments, the propeptide region of the heterologous or variant propeptide region comprises an amino acid sequence set forth in SEQ ID NO: 69 which is shown in FIG. 12. In some embodiments, each X can be any amino acid. In specific embodiments, the amino acids "X's" in SEQ ID NO: 44 can be selected from possible amino acids set forth below in Table 2.

TABLE 2

| Position | Amino Acid |
| --- | --- |
| 13 | N, K, or T |
| 20 | E, Q, or T |
| 27 | A, G, or E |
| 28 | N or absent |
| 29 | D or absent |
| 31 | V, E, or Y |
| 32 | A, S, or V |
| 34 | L, S, or I |
| 37 | A, V, or E |
| 59 | S, N, or D |

In some embodiments of the modified protease, the propeptide region of the heterologous or variant *Bacillus* protease comprises an amino acid sequence with at least 50%, 60%, 75%, 80%, 85%, 90%, 95%, 96%, 97%, 98%, or 99% identity to SEQ ID NO: 44 or 69.

Mature Region

In some embodiments, the mature region of the modified protease of the invention is from a *Bacillus gibsonii*-clade protease. Various species or strains of *Bacillus gibsonii*-clade members have been identified. Sequences of the serine proteases or subtilisins of many *Bacillus gibsonii*-clade members have been reported or disclosed in publications or patent applications including Deng et al. 2014 (*J. Microbiol.* *Biotechnol.* 24:197-208), PCT International Publication No. WO2015/089447, PCT International Publication No. WO2016/069563 and PCT International Publication No. WO2016/069569, all of which are incorporated herein by reference.

Set forth below are a few examples of *Bacillus gibsonii*-clade members and their serine protease precursor/preproenzyme sequences. The signal peptide sequences are underlined and in bold, the pro sequences are in italics, while the predicted mature enzyme sequences are in regular font. However, at least some of the predicted mature region sequences have not been confirmed to be producible in nature.

Bgi02446 of *Bacillus gibsonii* strain DSM8722, also known as AprBG (Deng et al. 2014), as well as homologous subtilisin enzymes encoded by strains DSM 9728, DSM 9729, DSM 9730, and DSM 9731 all share significant sequence identify and cluster in the same region of a subtilisin phylogenetic tree (see, PCT Publication No. WO2015/089447). They form the basis of the *B. gibsonii*-clade of subtilisins.

The amino acid sequence of the preproenzyme Bgi02446 is set forth as SEQ ID NO: 61 and the amino acid sequence of the predicted mature region of Bgi02446 is set forth as SEQ ID NO: 11.

(SEQ ID NO: 61)
MKRKVGKLMVGLVCVTALVTVTDSASAAEEKVKYLIGFEEEAELEAFTEE

IDQVGVFSVEEQSVAEDTLDIDVDIIDEYDYIDVLAVELDPEDVDALSEE

AGISFIEEDIELSIQQTVPWGITRVQAPAVHNRGITGSGVRVAILDSGIS

AHSDLNIRGGASFVPGEPTTADLNGHGTHVAGTVAALNNSIGVIGVAPNA

ELYAVKVLGANGSGSVSGIAQGLEWAATNNMHIANMSLGSDFPSSTLERA

VNYATSRDVLVIAATGNNGSGSVGYPARYANAMAVGATDQNNRRANFSQY

GTGIDIVAPGVNVQSTYPGNRYVSMNGTSMATPHVAGAAALVKQRYPSWN

ATQIRNHLKNTATNLGNSSQFGSGLVNAEAATR

As set forth below in Example 6, the predicted mature region of Bgi02446 comprising the sequence of SEQ ID NO: 11 (which has two glutamines (QQ) at the N-terminus) was produced using the propeptide region of a heterologous *Bacillus* protease operably linked thereto. When the native propeptide region of Bgi02446 was used to express the mature region of Bgi02446, a different form of mature region sequence was produced, which has only one glutamine (Q) at the N-terminus, the sequence of which is set forth in SEQ ID NO: 10.

The amino acid sequence of the DSM 9728 preproenzyme is set forth as SEQ ID NO: 62.

(SEQ ID NO: 62)
MKRRVGKLVVGLVCVTALVTVTDSASAAEEKVKYLIGFEEEAELEAFTEE

IDQVGVFSVEEQSVAEDTLDIDVDIIDEYDYIDVLAVELDPEDVDALSEE

AGISFIEEDIELSIQQTVPWGITRVQAPAVHNRGVTGSGVRVAILDSGIS

THSDLTIRGGASFVPGEPTTADLNGHGTHVAGTVAALNNSIGVIGVAPSA

DLYAVKVLGANGRGSVSGIAQGLEWAAANNMHIANMSLGSDAPSTTLERA

VNYATSQGVLVIAATGNNGSGSVGYPARYANAMAVGATDQNNRRANFSQY

GTGIDIVAPGVNVQSTYPGNRYASLNGTSMATPHVAGAAALVKQRYPSWN

ATQIRNHLKNTATNLGNSSQFGSGLVNAEAATR

The amino acid sequence of the DSM 9729 preproenzyme is set forth as SEQ ID NO: 63.

(SEQ ID NO: 63)
MKRRVGKLVVGLVCVTALVTVTDSASAAEEKVKYLIGFEEEAELEAFTEE

IDQVGVFSVEEQSVAEDTLDIDVDIIDEYDYIDVLAVELDPEDVDALSEE

AGISFIEEDIELSIQQTVPWGITRVQAPAVHNRGITGSGVRVAILDSGIS

AHSDLNIRGGASFVPGEPTTADLNGHGTHVAGTVAALNNSIGVIGVAPNA

DLYAVKVLGANGSGSVSGIAQGLEWAATNNMHIANMSLGSDFPSSTLERA

VNYATSRDVLVIAATGNNGSGSVGYPARYANAMAVGATDQNNRRANFSQY

GTGIDIVAPGVNVQSTYPGNRYVSMNGTSMATPHVAGAAALVKQRYPSWN

ATQIRNHLKNTATNLGNSSQFGSGLVNAEAATR

The amino acid sequence of the DSM 9730 preproenzyme is set forth as SEQ ID NO: 64.

(SEQ ID NO: 64)
MKRRVGKLVVGLVCVTALVTVTDSASAAEEKVKYLIGFEEEAELEAFTEE

IDQVGVFSVEEQSVAEDTLDIDVDIIDEYDYIDVLAVELDPEDVDALSEE

AGISFIEEDIELSIQQTVPWGITRVQAPAVHNRGVTGSGVRVAILDSGIS

THSDLTIRGGASFVPGEPTTADLNGHGTHVAGTVAALNNSIGVIGVAPSA

DLYAVKVLGANGRGSVSGIAQGLEWAAANNMHIANMSLGSDAPSTTLERA

VNYATSQGVLVIAATGNNGSGSVGYPARYANAMAVGATDQNNRRANFSQY

GTGIDIVAPGVNVQSTYPGNRYVSMNGTSMATPHVAGAAALVKQRYPSWN

ATQIRNHLKNTATNLGNSSQFGSGLVNAEAATR

A few other serine protease *Bacillus gibsonii*-clade subtilisin members are also classified under the *Bacillus gibsonii*-clade. For example, the *B. gibsonii* subtilisin BSP-00801, which is a variant of the naturally-occurring *B. gibsonii* subtilisin Bgi02446, is also classified herein under the *Bacillus gibsonii*-clade. This protein is also disclosed in the U.S. provisional patent application Ser. No. 62/180,673, entitled "*Bacillus gibsonii*-Clade Serine Proteases", filed Jun. 17, 2015, which is herein incorporated by reference in its entirety. Sequences of two forms of the mature region of BSP-00801 are shown in SEQ ID NO: 12 and SEQ ID NO: 13. Other variants of Bgi02446 disclosed in U.S. provisional patent application Ser. No. 62/180,673 can also be used to provide the mature regions for the modified proteases of the current invention.

The amino acid sequence of the DSM 9731 preproenzyme is set forth as SEQ ID NO: 57.

(SEQ ID NO: 57)
MKRRVGKLVVGLVCVTALVTVTDSASAAEEKVKYLIGFEEEAELEAFTEE

IDQVGVFSVEEQSVAEDTLDIDVDIIDEYDYIDVLAVELDPEDVDALSEE

AGISFIEEDIELSIQQTVPWGITRVQAPAVHNRGVTGSGVRVAILDSGIS

THSDLTIRGGASFVPGEPTTADLNGHGTHVAGTVAALNNSIGVIGVAPSA

DLYAVKVLGANGRGSVSGIAQGLEWAAANNMHIANMSLGSDAPSTTLERA

VNYATSQGVLVIAATGNNGSGSVGYPARYANAMAVGATDQNNRRANFSQY

-continued

GSGIDIVAPGVNVQSTYPGNRYVSMNGTSMATPHVAGAAALVKQRYPSWN

ATQIRNHLKNTATNLGNSSQFGSGLVNAEAATR

A few other serine proteases have been identified and can be classified under the *Bacillus gibsonii*-clade. For example, *B. gibsonii* subtilisin (Derwent Patent Index Accession No. CAV33594) as disclosed in PCT Publication No. WO2008/086916, *B. gibsonii* subtilicin TII-5 disclosed in WO2003/054185 (Accession No. CAE48424), *B. gibsonii* subtilicin TI-1 disclosed in WO2003/054184 (Accession No. CAE48421), and *B. gibsonii* subtilicin HP302 disclosed in WO2007/131657 (Accession No. CAS91385), all of which disclosed by Henkel AG & Co. The predicted mature regions of these sequences are extracted and shown below.

The amino acid sequence of the predicted mature region of WO2003/054184-CAE48421 is set forth as SEQ ID NO: 65, the amino acid sequence of the predicted mature region of WO2003/054185-CAE48424 is set forth as SEQ ID NO: 66, the amino acid sequence of the predicted mature region of WO2007/131657-CAS91385 is set forth as SEQ ID NO: 67 and the amino acid sequence of the predicted mature region of WO20008/086916-CAV33594 is set forth as SEQ ID NO: 68.

In some embodiments, the mature region of the modified protease of the invention is from a wild-type *Bacillus gibsonii*-clade subtilisin. In other embodiments, the mature region of the modified protease is from a mutated or a variant *Bacillus gibsonii*-clade subtilisin. In some embodiments, the mature region of the modified protease is from a subtilisin selected from the group consisting of Bgi02446, DSM9728, DSM9729, DSM9730, DSM9731, *B. gibsonii* TII-5 (WO2003/054185-CAE48424), *B. gibsonii* TI-1 disclosed in (WO2003/054184-CAE48421), *B. gibsonii* HP302 (WO2007/131657-CAS91385 and WO2008/086916-CAV33594). In certain embodiments, the mature region of the modified protease is from the Bgi024446 subtilisin. In other embodiments, the mature region of the modified protease is from a variant of the Bgi024446 subtilisin. In certain embodiments, the mature region is from BSP-00801.

In some embodiments of the modified protease of the invention, the mature region is from a *Bacillus* protease that may not be classified under the *Bacillus gibsonii*-clade but is homologous to a *Bacillus gibsonii*-clade subtilisin. In certain embodiments, the mature region comprises an amino acid sequence with at least 60% identity to SEQ ID NO: 10, 11, 12, or 13. In some embodiments, the mature region comprises an amino acid sequence with at least 65%, 70%, 75%, 76%, 77%, 78%, or 79% identity to SEQ ID NO: 10, 11, 12, or 13. In some embodiments, the mature region comprises an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% identity to SEQ ID NO: 10, 11, 12, or 13. In some embodiments, the mature region comprises the amino acid sequence of SEQ ID NO: 10, 11, 12, or 13.

Polynucleotides, Expression Vectors, Chromosomes, and Host Cells

In one aspect, the present invention provides polynucleotides that encode modified proteases which have a heterologous pro region or at least one mutation in the native pro region of the protease to be produced.

In some embodiments, the polynucleotide encodes the modified proteases described herein.

In some embodiments, the invention provides a polynucleotide encoding a modified protease, said polynucleotide comprising:
a) optionally a first polynucleotide region encoding a signal peptide;
b) a second polynucleotide region encoding the propeptide region of a heterologous *Bacillus* protease, said propeptide region comprising an amino acid sequence with at least 40% identity to SEQ ID NO: 8; and
c) a third polynucleotide region encoding the mature region of a *Bacillus gibsonii*-clade protease;
wherein the first polynucleotide region is operably linked to the second polynucleotide region, and the second polynucleotide region is operably linked to the third polynucleotide region.

In some embodiments, the invention provides a polynucleotide encoding a modified protease, said polynucleotide comprising:

a) optionally a first polynucleotide region encoding a signal peptide;

b) a second polynucleotide region encoding the propeptide region of a protease from *Bacillus lentus* or a related species thereof; and c) a third polynucleotide region encoding the mature region of a *Bacillus gibsonii*-clade protease;

wherein the first polynucleotide region is operably linked to the second polynucleotide region, and the second polynucleotide region is operably linked to the third polynucleotide region.

In some embodiments, the polynucleotide comprises the first polynucleotide region. In other embodiments, the polynucleotide does not comprise the first polynucleotide region.

In some embodiments of the polynucleotide, said second polynucleotide region encodes the propeptide region of a protease from *Bacillus lentus* or a related species thereof.

In some embodiments of the polynucleotide, said second polynucleotide region encodes the propeptide region of a protease from a *Bacillus* species selected from the group consisting of *Bacillus lentus, Bacillus clausii, Bacillus alcalophilus, Bacillus lehensis*, and *Bacillus novalis*.

In some embodiments of the polynucleotide, said second polynucleotide region encodes the propeptide region of a protease from *Bacillus lentus*.

In some embodiments of the polynucleotide, said second polynucleotide region encodes the propeptide region of a serine protease or subtilisin from *Bacillus lentus* or a related species thereof.

In some embodiments of the polynucleotide, said second polynucleotide region encodes a wild-type propeptide region of a subtilisin from *Bacillus lentus* or a related species thereof.

In some embodiments of the polynucleotide, said second polynucleotide region encodes a variant propeptide region of a subtilisin from *Bacillus lentus* or a related species thereof.

In some embodiments of the polynucleotide, said second polynucleotide region encodes the propeptide region of a subtilisin selected from the group consisting of BspQ01211, Bps02592, *B. lentus*_P29600, BspAL03240, Bpan01744, *B. clausii*_P41362, *B. lehensis*_AFK08970, Bps02003, Bohn00569, BspAK01305, Bpan04382, and BspAL03279.

In some embodiments of the polynucleotide, said second polynucleotide region encodes the propeptide region of a subtilisin selected from the group consisting of BspQ01211, Bps02592, *B. lentus*_P29600, BspAL03240, *B. clausii*_P41362, *B. lehensis*_AFK08970, and Bpan01744.

In some embodiments of the polynucleotide, said second polynucleotide region encodes the propeptide region of *B. lentus*_P29600.

In some embodiments of the polynucleotide, said second polynucleotide region encodes an amino acid sequence with at least 50% identity to SEQ ID NO: 8.

In some embodiments of the polynucleotide, wherein said second polynucleotide region encodes an amino acid sequence with at least 75% identity to SEQ ID NO: 8

In some embodiments of the polynucleotide, said second polynucleotide region encodes an amino acid sequence with at least 90% identity to SEQ ID NO: 8

In some embodiments of the polynucleotide, said second polynucleotide region encodes an amino acid sequence comprising the sequence of SEQ ID NO: 8

In some embodiments of the polynucleotide, said second polynucleotide region encodes a variant propeptide region of a subtilisin from *Bacillus lentus* or a related species thereof, wherein the variant propeptide region comprises at least one amino acid substitution at a position corresponding to position 6, 30, or 32 of SEQ ID NO: 8

In some embodiments of the polynucleotide, said at least one amino acid substitution enhances production of said mature region of the *Bacillus gibsonii*-clade protease by a *Bacillus* sp. host cell. In some embodiments, said *Bacillus* sp. host cell is a *Bacillus subtilis* host cell.

In some embodiments of the polynucleotide, said at least one amino acid substitution enhances production of said mature region of the *Bacillus gibsonii*-clade protease as compared to a polynucleotide comprising the same first polynucleotide region and third polynucleotide region but a second polynucleotide region encoding a wild-type propeptide region of the same subtilisin.

In some embodiments of the polynucleotide, said at least one amino acid substitution is at the position corresponding to position 6 of SEQ ID NO: 8, and the native amino acid at said position is substituted with an amino acid selected from the group consisting of A, C, R, N, Q, G, H, I, L, K, M, F, P, S, T, W, Y, and V.

In some embodiments of the polynucleotide, said at least one amino acid substitution is at the position corresponding to position 30 of SEQ ID NO: 8, and the native amino acid at said position is substituted with an amino acid selected from the group consisting of A, R, N, D, C, Q, G, H, L, K, M, S, T, W, Y, and V.

In some embodiments of the polynucleotide, said at least one amino acid substitution is at the position corresponding to position 32 of SEQ ID NO: 8, and the native amino acid at said position is substituted with an amino acid selected from the group consisting of R, N, C, Q, G, H, I, L, K, M, F, P, S, T, W, Y, and V.

In some embodiments of the polynucleotide, said second polynucleotide region encodes the propeptide region set forth in SEQ ID NO: 8 with the proviso that said propeptide region comprises at least one amino acid substitution at positions chosen from positions 6, 30 and 32 of SEQ ID NO: 8.

In some embodiments of the polynucleotide, said propeptide region comprises an amino acid substitution at position 6 of SEQ ID NO: 8 selected from the group consisting of E6A, E6C, E6R, E6N, E6Q, E6G, E6H, E6I, E6L, E6K, E6M, E6F, E6P, E6S, E6T, E6W, E6Y, and E6V.

In some embodiments of the polynucleotide, said propeptide region comprises an amino acid substitution at position 30 of SEQ ID NO: 8 selected from the group consisting of E30A, E30R, E30N, E30D, E30C, E30Q, E30G, E30H, E30L, E30K, E30M, E30S, E30T, E30W, E30Y, and E30V.

In some embodiments of the polynucleotide, said propeptide region comprises an amino acid substitution at position 32 of SEQ ID NO: 8 selected from the group consisting of A32R, A32N, A32C, A32Q, A32G, A32H, A32I, A32L, A32K, A32M, A32F, A32P, A32S, A32T, A32W, A32Y, and A32V.

In certain embodiments of the polynucleotide of invention wherein the second polynucleotide encodes the propeptide region of a heterologous *Bacillus* protease and wherein the propeptide region comprises an amino acid sequence with at least 40% identity to SEQ ID NO: 8, the propeptide region does not comprise any amino acid selected from the group consisting of D, P, and W at the position corresponding to position 6 of SEQ ID NO: 8. In certain embodiments, the propeptide region encoded by the second polynucleotide does not comprise any amino acid selected from the group consisting of D, C, Y, P, and W at the position corresponding to position 6 of SEQ ID NO: 8. In certain embodiments, the propeptide region encoded by the second polynucleotide does not comprise any amino acid selected from the group consisting of N, H, I, F, S, V, D, C, P, Y, and W at the position corresponding to position 6 of SEQ ID NO: 8. In some embodiments, the propeptide region encoded by the second polynucleotide does not comprise any amino acid selected from the group consisting of I, P, and Y at the position corresponding to position 30 of SEQ ID NO: 8. In certain embodiments, the propeptide region encoded by the second polynucleotide does not comprise amino acid Q at the position corresponding to position 32 of SEQ ID NO: 8. In certain embodiments, the propeptide region encoded by the second polynucleotide does not comprise any amino acid selected from the group consisting of N, L, P, and Q at the position corresponding to position 32 of SEQ ID NO: 8.

In some embodiments of the polynucleotide, said second polynucleotide region comprises a nucleotide sequence with at least 60% identity to SEQ ID NO: 5.

In some embodiments of the polynucleotide, said second polynucleotide region comprises a nucleotide sequence with at least 90% identity to SEQ ID NO: 5.

In some embodiments of the polynucleotide, said second polynucleotide region comprises the sequence of SEQ ID NO: 5.

In some embodiments of the polynucleotide, said second polynucleotide region comprises the sequence set forth in SEQ ID NO: 5 with the proviso that the sixth, the thirtieth, or the thirty second codon of SEQ ID NO: 5 is mutated to encode a different amino acid.

In some embodiments, the invention provides a polynucleotide encoding a modified protease, said polynucleotide comprising:
  a) optionally a first polynucleotide region encoding a signal peptide;
  b) a second polynucleotide region encoding a variant propeptide region of a first *Bacillus gibsonii*-clade protease; and
  c) a third polynucleotide region encoding the mature region of a second *Bacillus gibsonii*-clade protease;
wherein the first polynucleotide region is operably linked to the second polynucleotide region, and the second polynucleotide region is operably linked to the third polynucleotide region.

In some embodiments of the polynucleotide, said first *Bacillus gibsonii*-clade protease or said second *Bacillus gibsonii*-clade protease is a serine protease or subtilisin.

In some embodiments of the polynucleotide, said first *Bacillus gibsonii*-clade protease and said second *Bacillus gibsonii*-clade protease are from the same *Bacillus* species.

In some embodiments of the polynucleotide, said first *Bacillus gibsonii*-clade protease and said second *Bacillus gibsonii*-clade protease are from different *Bacillus* species.

In some embodiments of the polynucleotide, said second polynucleotide region encodes an amino acid sequence with at least 60% identity to SEQ ID NO: 7.

In some embodiments of the polynucleotide, said second polynucleotide region encodes an amino acid sequence with at least 90% identity to SEQ ID NO: 7.

In some embodiments of the polynucleotide, said second polynucleotide region encodes a variant propeptide region with at least 60% identity to SEQ ID NO: 7, wherein the variant propeptide region comprises an amino acid substitution at a position corresponding to position 34 of SEQ ID NO: 7.

In some embodiments of the polynucleotide, said second polynucleotide region encodes the propeptide region set forth in SEQ ID NO: 7 with the proviso that said propeptide region comprises an amino acid substitution at position 34 of SEQ ID NO: 7. In some embodiments, the native amino acid at said position is substituted with an amino acid selected from the group consisting of D, C, G, H, S, and V. In some embodiments, said amino acid substitution at position 34 of SEQ ID NO: 7 is selected from the group consisting of E34D, E34C, E34G, E34H, E34S, and E34V In some embodiments of the polynucleotide, said amino acid substitution enhances the production of said mature region of the second *Bacillus gibsonii*-clade protease by a *Bacillus* sp. host cell. In some embodiments, said *Bacillus* sp. host cell is a *Bacillus subtilis* host cell.

In certain embodiments of the polynucleotide of invention wherein the second polynucleotide encodes a variant propeptide region of a first *Bacillus gibsonii*-clade protease, the propeptide region does not comprise any amino acid selected from the group consisting of A, R, N, Q, I, L, K, M, F, P, T, Y, and W at the position corresponding to position 34 of SEQ ID NO: 7. In certain embodiments, the variant propeptide region does not comprise a substitute amino acid at the position corresponding to position 6 or 36 of SEQ ID NO: 7.

In some embodiments of the polynucleotide, said second polynucleotide region comprises a nucleotide sequence with at least 60% identity to SEQ ID NO: 3.

In some embodiments of the polynucleotide, said second polynucleotide region comprises a nucleotide sequence with at least 90% identity to SEQ ID NO: 3.

In some embodiments of the polynucleotide, said second polynucleotide region comprises the sequence set forth in SEQ ID NO: 3 with the proviso that the thirty fourth codon of SEQ ID NO: 3 is mutated to encode a different amino acid.

In some embodiments of the polynucleotide, said second polynucleotide region encodes a heterologous or variant propeptide region that comprises an amino acid sequence set forth in SEQ ID NO: 44.

In some embodiments of the polynucleotide, herein said second polynucleotide region encodes a heterologous or variant propeptide region that comprises an amino acid sequence set forth in SEQ ID NO: 69.

In some embodiments of the polynucleotide, said third polynucleotide region encodes the mature region of a protease from *Bacillus gibsonii.*

In some embodiments of the polynucleotide, said third polynucleotide region encodes the mature region of a *Bacillus gibsonii*-clade serine protease or subtilisin.

In some embodiments of the polynucleotide, said third polynucleotide region encodes the mature region of a wild-type *Bacillus gibsonii*-clade subtilisin.

In some embodiments of the polynucleotide, said third polynucleotide region encodes the mature region of a variant *Bacillus gibsonii*-clade subtilisin.

In some embodiments of the polynucleotide, said third polynucleotide region encodes the mature region of a subtilisin selected from the group consisting of Bgi02446, DSM9728, DSM9729, DSM9730, DSM9731, *B. gibsonii* TII-5 (WO2003/054185-CAE48424), *B. gibsonii* TI-1 (WO2003/054184-CAE48421), *B. gibsonii* HP302 (WO2007/131657-CAS91385), and WO2008/086916-CAV33594.

In some embodiments of the polynucleotide, said third polynucleotide region encodes the mature region of Bgi024446.

In some embodiments of the polynucleotide, said third polynucleotide region encodes the mature region of a variant of Bgi024446.

In some embodiments of the polynucleotide, said third polynucleotide region encodes an amino acid sequence with at least 60%, 65%, 70%, 75%, 80%, 85%, 90%, 95%, 96%, 97%, 98%, or 99% identity to SEQ ID NO: 10, 11, 12, or 13. In some embodiments, said third polynucleotide region encodes an amino acid sequence comprising the sequence of SEQ ID NO: 10, 11, 12, or 13. In some embodiments, said third polynucleotide region encodes an amino acid sequence comprising the sequence of SEQ ID NO: 10 or 11. In some embodiments, said third polynucleotide region encodes an amino acid sequence comprising the sequence of SEQ ID NO: 12 or 13.

In some embodiments of the polynucleotide, said third polynucleotide region comprises a nucleotide sequence with at least 60%, 65%, 70%, 75%, 80%, 85%, 90%, 95%, 96%, 97%, 98%, or 99% identity to SEQ ID NO: 4 or 9. In some embodiments, said third polynucleotide region comprises the sequence of SEQ ID NO: 4 or 9.

In some embodiments of the polynucleotide, said first polynucleotide region is present and encodes a *Bacillus* signal peptide. In some embodiments, said first polynucleotide region is present and encodes a *Bacillus subtilis* signal peptide. In some embodiments, said first polynucleotide region encodes an amino acid sequence with at least 60%, 65%, 70%, 75%, 80%, 85%, 90%, 95%, 96%, 97%, 98%, or 99% identity to SEQ ID NO: 40. In some embodiments, said first polynucleotide region encodes an amino acid sequence comprising the sequence of SEQ ID NO: 40.

In some embodiments of the polynucleotide, said first polynucleotide region is present and comprises a nucleotide sequence with at least 60%, 65%, 70%, 75%, 80%, 85%, 90%, 95%, 96%, 97%, 98%, or 99% identity to SEQ ID NO: 2. In some embodiments, said first polynucleotide region comprises the nucleotide sequence of SEQ ID NO: 2:

In some embodiments, the invention provides a polynucleotide encoding a modified protease, said polynucleotide comprising:

a) a first polynucleotide region encoding the amino acid sequence of SEQ ID NO: 40;

b) a second polynucleotide region encoding the amino acid sequence of SEQ ID NO: 8 or encoding the sequence of SEQ ID NO: 8 with at least one amino acid substitution selected from the group consisting of E6A, E6C, E6R, E6N, E6Q, E6G, E6H, E6I, E6L, E6K, E6M, E6F, E6P, E6S, E6T, E6W, E6Y, E6V, E30A, E30R, E30N, E30D, E30C, E30Q, E30G, E30H, E30L, E30K, E30M, E30S, E30T, E30W, E30Y, E30V, A32R, A32N, A32C, A32Q, A32G, A32H, A32I, A32L, A32K, A32M, A32F, A32P, A32S, A32T, A32W, A32Y, and A32V; and c) a third polynucleotide region encoding the amino acid sequence of SEQ ID NO: 11 or 12;

wherein the first polynucleotide region is operably linked to the second polynucleotide region, and the second polynucleotide region is operably linked to the third polynucleotide region.

In some embodiments, the invention provides a polynucleotide encoding a modified protease, said polynucleotide comprising:

a) a first polynucleotide region encoding the amino acid sequence of SEQ ID NO: 40;

b) a second polynucleotide region encoding the amino acid sequence of SEQ ID NO: 7 with an amino acid substitution selected from the group consisting of E34D, E34C, E34G, E34H, E34S, and E34V; and c) a third polynucleotide region encoding the amino acid sequence of SEQ ID NO: 11 or 12;

wherein the first polynucleotide region is operably linked to the second polynucleotide region, and the second polynucleotide region is operably linked to the third polynucleotide region.

In one aspect, the invention provides expression vectors comprising the polynucleotide of the invention.

In another aspect, the invention provides modified chromosomes comprising the polynucleotide of the invention. A chromosome can be altered by introducing to the host cells DNA constructs with the polynucleotides of the invention that are integrated to the chromosome. A chromosome can also be mutated in-situ without foreign DNA constructs.

In some embodiments, the expression vector or the modified chromosome further comprises a promoter that is suitable for gene expression in *Bacillus subtilis* and operably linked to the first polynucleotide region.

In one aspect, the invention provides *Bacillus* sp. host cells comprising the polynucleotide, the expression vector, or the modified chromosome of the invention. In some embodiments, said host cell is a *B. subtilis* host cell.

As indicated above, in some embodiments, the present invention provides vectors comprising the aforementioned modified polynucleotides. In some embodiments, the vector is an expression vector in which the modified polynucleotide sequence encoding the modified protease of the invention is operably linked to additional segments required for efficient gene expression (e.g., a promoter operably linked to the gene of interest). In some embodiments, these necessary elements are supplied as the gene's own homologous promoter if it is recognized, (i.e., transcribed by the host), and a transcription terminator that is exogenous or is supplied by the endogenous terminator region of the protease gene. In some embodiments, a selection gene such as an antibiotic resistance gene that enables continuous cultural maintenance of plasmid-infected host cells by growth in antimicrobial-containing media is also included.

In some embodiments, the expression vector is derived from plasmid or viral DNA, or in alternative embodiments, contains elements of both. Exemplary vectors include, but are not limited to pXX, pC194, pJH101, pE194, pHP13 (Harwood and Cutting (eds), *Molecular Biological Methods for Bacillus*, John Wiley & Sons, 1990, in particular, chapter 3; suitable replicating plasmids for *B. subtilis* include those listed on page 92; Perego, M. (1993) Integrational Vectors for Genetic Manipulations in *Bacillus subtilis, p.* 615-624; A. L. Sonenshein, J. A. Hoch, and R. Losick (ed.), *Bacillus subtilis* and other Gram-positive bacteria: biochemistry, physiology and molecular genetics, American Society for Microbiology, Washington, D.C.).

Figure 4:
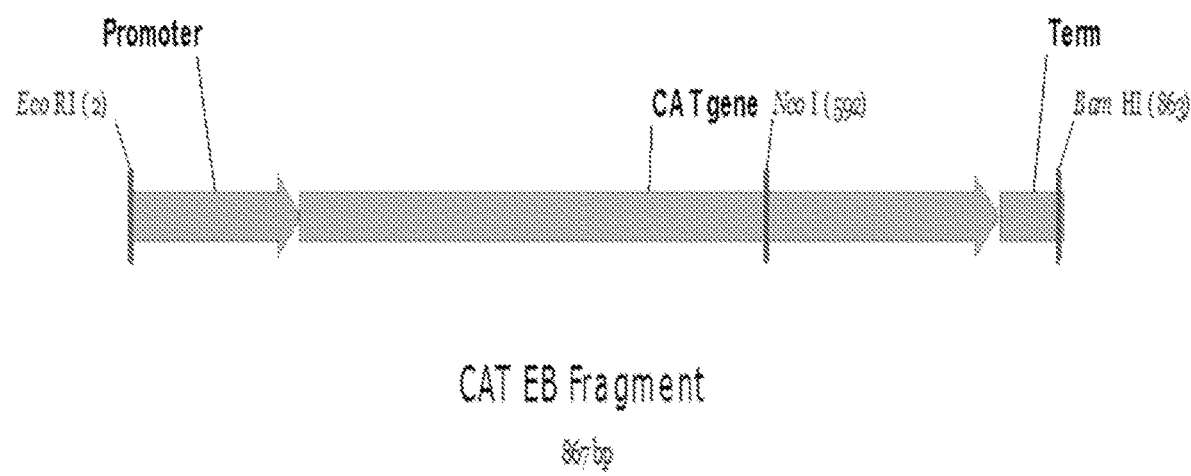
FIG. 4 shows a diagram of the gene cassette of the *Staphylococcus aureus* chloramphenicol acetyl transferase (CAT) gene used to ligate to the gene cassettes shown in FIGS. 2 and 3.
Figure 5:
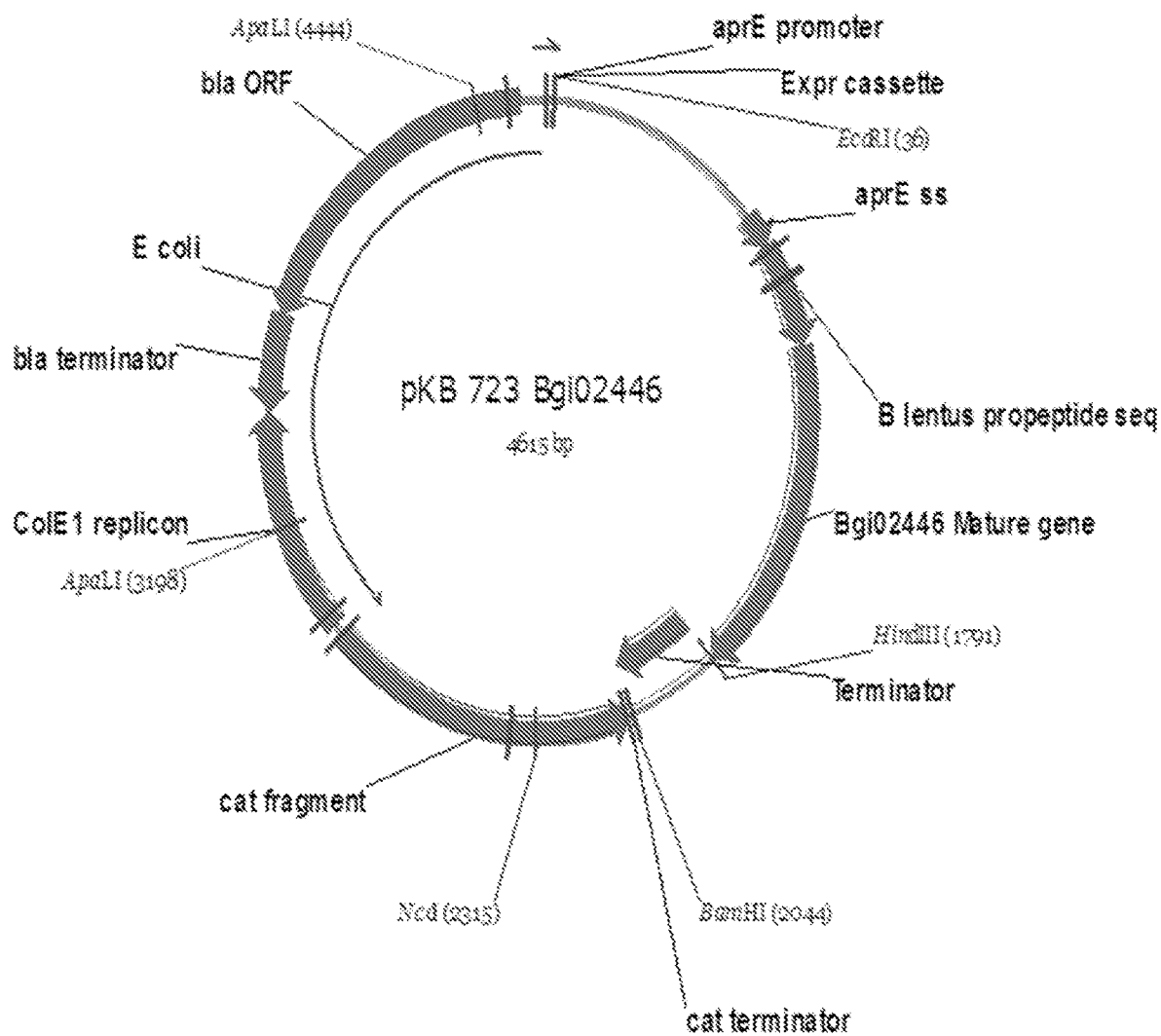
FIG. 5 illustrates a schematic of a plasmid constructed for expression of mature Bgi02446 using various *B. lentus* propeptide sequences with mutations (i.e., substitutions) at amino acid residue positions 6, 30, or 32.
Figure 6:
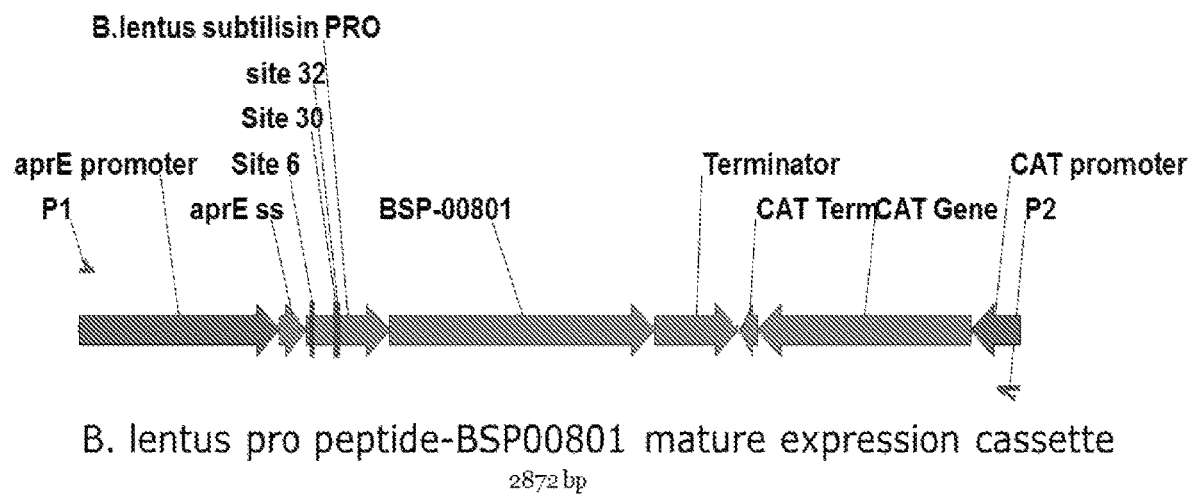
FIG. 6 shows a diagram of the expression cassette used for the expression of the mature region of BSP-00801 (i.e., a variant *B. gibsonii* subtilisin) with the *B. lentus* propeptide sequence.

For expression and production of protein(s) of interest e.g. a protease, in a cell, at least one expression vector comprising at least one copy of a polynucleotide encoding the modified protease, and preferably comprising multiple copies, is transformed into the cell under conditions suitable for expression of the protease. In some particularly embodiments, the sequences encoding the proteases (as well as other sequences included in the vector) are integrated into the genome of the host cell, while in other embodiments, the plasmids remain as autonomous extra-chromosomal elements within the cell. Thus, the present invention provides both extrachromosomal elements as well as incoming sequences that are integrated into the host cell genome. It is intended that each of the vectors described herein will find use in the present invention. In some embodiments, the polynucleotide construct encoding the modified protease is present on an integrating vector (e.g., pJH-GG36; FIG. 4) that enables the integration and optionally the amplification of the modified polynucleotide into the bacterial chromosome. Examples of sites for integration include, but are not limited to the aprE, the amyE, the veg or the pps regions. Indeed, it is contemplated that other sites known to those skilled in the art will find use in the present invention. In some embodiments, transcription of the polynucleotides encoding the modified proteases is effectuated by a promoter that is the wild-type promoter for the selected precursor protease. In some other embodiments, the promoter is heterologous to the precursor protease, but is functional in the host cell. Specifically, examples of suitable promoters for use in bacterial host cells include but are not limited to the amyE, amyQ, amyL, pstS, sacB, pSPAC, pAprE, pVeg, pHpaII promoters, the promoter of the *B. stearothermophilus* maltogenic amylase gene, the *B. amyloliquefaciens* (BAN) amylase gene, the *B. subtilis* alkaline protease gene, the *B. clausii* alkaline protease gene the *B. pumilis* xylosidase gene, the *B. thuringiensis* crylllA, and the *B. licheniformis* alpha-amylase gene.

Additional promoters include, but are not limited to the A4 promoter, as well as phage Lambda $P_R$ or $P_L$ promoters, and the *E. coli* lac, trp or tac promoters.

Precursor and modified proteases are produced in host cells of any suitable Gram-positive microorganism, including bacteria and fungi. For example, in some embodiments, the modified protease is produced in host cells of fungal and/or bacterial origin. In some embodiments, the host cells are *Bacillus* sp., *Streptomyces* sp., *Escherichia* sp. or *Aspergillus* sp. In some embodiments, the modified proteases are produced by *Bacillus* sp. host cells. Examples of *Bacillus* sp. host cells that find use in the production of the modified proteins of the present invention include, but are not limited to *B. licheniformis*, *B. lentus*, *B. subtilis*, *B. amyloliquefaciens*, *B. lentus*, *B. brevis*, *B. stearothermophilus*, *B. alkalophilus*, *B. coagulans*, *B. circulans*, *B. pumilis*, *B. thuringiensis*, *B. clausii*, and *B. megaterium*, as well as other organisms within the genus *Bacillus*. In some embodiments, *B. subtilis* host cells find use. U.S. Pat. Nos. 5,264,366 and 4,760,025 (RE 34,606) describe various *Bacillus* host strains that find use in the present invention, although other suitable strains find use in the present invention.

Several industrial strains that find use in the present invention include non-recombinant (i.e., wild-type) *Bacillus* sp. strains, as well as variants of naturally occurring strains and/or recombinant strains. In some embodiments, the host strain is a recombinant strain, wherein a polynucleotide encoding a polypeptide of interest has been introduced into the host. In some embodiments, the host strain is a *B. subtilis* host strain and particularly a recombinant *Bacillus subtilis* host strain. Numerous *B. subtilis* strains are known, including but not limited to 1A6 (ATCC 39085), 168 (1A01), SB19, W23, Ts85, B637, PB1753 through PB1758, PB3360, JH642, 1A243 (ATCC 39,087), ATCC 21332, ATCC 6051, MI113, DE100 (ATCC 39,094), GX4931, PBT 110, and PEP 211 strain (see e.g., Hoch et al., Genetics, 73:215-228, 1973; U.S. Pat. Nos. 4,450,235; 4,302,544; and EP 0134048; each of which is incorporated by reference in its entirety). The use of *B. subtilis* as an expression host well known in the art (see e.g., See, Palva et al., Gene 19:81-87, 1982; Fahnestock and Fischer, J. Bacteriol., 165:796-804, 1986; and Wang et al., Gene 69:39-47, 1988).

In some embodiments, the *Bacillus* host is a *Bacillus* sp. that includes a mutation or deletion in at least one of the following genes, degU, degS, degR and degQ. Preferably the mutation is in a degU gene, and more preferably the mutation is degU(Hy)32. (see e.g., Msadek et al., J. Bacteriol., 172:824-834, 1990 and Olmos et al., Mol. Gen. Genet., 253:562-567, 1997). A preferred host strain is a *Bacillus subtilis* carrying a degU32(Hy) mutation. In some further embodiments, the *Bacillus* host comprises a mutation or deletion in scoC4, (see, e.g., Caldwell et al., J. Bacteriol., 183:7329-7340, 2001); spoIIE (see, Arigoni et al., Mol. Microbiol., 31:1407-1415, 1999); and/or oppA or other genes of the opp operon (see, Perego et al., Mol. Microbiol., 5:173-185, 1991). Indeed, it is contemplated that any mutation in the opp operon that causes the same phenotype as a mutation in the oppA gene will find use in some embodiments of the altered *Bacillus* strain of the present invention. In some embodiments, these mutations occur alone, while in other embodiments, combinations of mutations are present. In some embodiments, an altered *Bacillus* that can be used to produce the modified proteases of the invention is a *Bacillus* host strain that already includes a mutation in one or more of the above-mentioned genes. In addition, *Bacillus* sp. host cells that comprise mutation(s) and/or deletions of endogenous protease genes find use. In some embodiments, the *Bacillus* host cell comprises a deletion of the aprE and the nprE genes. In other embodiments, the *Bacillus* sp. host cell comprises a deletion of 5 protease genes (see, U.S. Publication No. US2005/0202535), while in other embodiments, the *Bacillus* sp. host cell comprises a deletion of 9 protease genes (see, U.S. Publication No. US2005/0202535).

Host cells are transformed with modified polynucleotides encoding the modified proteases of the present invention using any suitable method known in the art. Whether the modified polynucleotide is incorporated into a vector or is used without the presence of plasmid DNA, it is introduced into a microorganism, in some embodiments, preferably an *E. coli* cell or a competent *Bacillus* cell. Methods for introducing DNA into *Bacillus* cells involving plasmid constructs and transformation of plasmids into *E. coli* are well known. In some embodiments, the plasmids are subsequently isolated from *E. coli* and transformed into *Bacillus*. However, it is not essential to use intervening microorganisms such as *E. coli*, and in some embodiments, a DNA construct or vector is directly introduced into a *Bacillus* host.

Those of skill in the art are well aware of suitable methods for introducing polynucleotide sequences into *Bacillus* cells (see e.g., Ferrari et al., "Genetics," in Harwood et al. (ed.), *Bacillus*, Plenum Publishing Corp., 1989, pages 57-72; Saunders et al., *J. Bacteriol.*, 157:718-726, 1984; Hoch et al., *J. Bacteriol.*, 93:1925-1937, 1967; Mann et al., *Current Microbiol.*, 13:131-135, 1986; and Holubova, Folia *Micro-* biol., 30:97, 1985; Chang et al., *Mol. Gen. Genet.,* 168:11-115, 1979; Vorobjeva et al., *FEMS Microbiol. Lett.,* 7:261-263, 1980; Smith et al., *Appl. Env. Microbiol.,* 51:634, 1986; Fisher et al., *Arch. Microbiol.,* 139:213-217, 1981 and McDonald, *J. Gen. Microbiol.,* 130:203, 1984). Indeed, such methods as transformation, including protoplast transformation and congression, transduction, and protoplast fusion are known and suited for use in the present invention. Methods of transformation are used to introduce a DNA construct provided by the present invention into a host cell. Methods known in the art to transform *Bacillus,* include such methods as plasmid marker rescue transformation, which involves the uptake of a donor plasmid by competent cells carrying a partially homologous resident plasmid (Contente et al., *Plasmid* 2:555-571, 1979; Haima et al., *Mol. Gen. Genet.,* 223:185-191, 1990; Weinrauch et al., *J. Bacteriol.,* 154:1077-1087, 1983; and Weinrauch et al., *J. Bacteriol.,* 169:1205-1211, 1987). In this method, the incoming donor plasmid recombines with the homologous region of the resident "helper" plasmid in a process that mimics chromosomal transformation.

In addition to commonly used methods, in some embodiments, host cells are directly transformed (i.e., an intermediate cell is not used to amplify, or otherwise process, the DNA construct prior to introduction into the host cell). Introduction of the DNA construct into the host cell includes those physical and chemical methods known in the art to introduce DNA into a host cell without insertion into a plasmid or vector. Such methods include, but are not limited to calcium chloride precipitation, electroporation, naked DNA, liposomes and the like. In additional embodiments, DNA constructs are co-transformed with a plasmid, without being inserted into the plasmid. In further embodiments, a selective marker is deleted from the altered *Bacillus* strain by methods known in the art (See, Stahl et al, *J. Bacteria.,* 158:411-418, 1984 and Palmeros et al., *Gene* 247:255-264, 2000).

In some embodiments, the transformed cells of the present invention are cultured in conventional nutrient media. The suitable specific culture conditions, such as temperature, pH and the like are known to those skilled in the art. In addition, some culture conditions may be found in the scientific literature such as Hopwood (2000) *Practical Streptomyces Genetics,* John Innes Foundation, Norwich UK; Hardwood et al., (1990) *Molecular Biological Methods for Bacillus,* John Wiley and from the American Type Culture Collection (ATCC).

In some embodiments, host cells transformed with polynucleotide sequences encoding modified proteases are cultured in a suitable nutrient medium under conditions permitting the expression of the present protease, after which the resulting protease is recovered from the culture. The medium used to culture the cells comprises any conventional medium suitable for growing the host cells, such as minimal or complex media containing appropriate supplements. Suitable media are available from commercial suppliers or may be prepared according to published recipes (e.g., in catalogues of the American Type Culture Collection). In some embodiments, the protease produced by the cells is recovered from the culture medium by conventional procedures, including, but not limited to separating the host cells from the medium by centrifugation or filtration, precipitating the proteinaceous components of the supernatant or filtrate by means of a salt (e.g., ammonium sulfate), chromatographic purification (e.g., ion exchange, gel filtration, affinity, etc.). Thus, any method suitable for recovering the protease(s) of the present invention finds use in the present invention. Indeed, it is not intended that the present invention be limited to any particular purification method.

The protein produced by a recombinant host cell comprising a modified protease of the present invention is secreted into the culture media. In some embodiments, other recombinant constructions join the heterologous or homologous polynucleotide sequences to nucleotide sequence encoding a protease polypeptide domain which facilitates purification of the soluble proteins (Kroll et al., *DNA Cell Biol* 12:441-453, 1993). Such purification facilitating domains include, but are not limited to, metal chelating peptides such as histidine-tryptophan modules that allow purification on immobilized metals (Porath J., *Protein Expr Purif* 3:263-281, 1992), protein A domains that allow purification on immobilized immunoglobulin, and the domain utilized in the FLAGS extension/affinity purification system (Immunex Corp, Seattle Wash.). The inclusion of a cleavable linker sequence such as Factor XA or enterokinase (Invitrogen, San Diego Calif.) between the purification domain and the heterologous protein also find use to facilitate purification.

As indicated above, the invention provides for modified full-length polynucleotides that encode modified full-length proteases that are processed by a *Bacillus* host cell to produce the mature form at a level that is greater than that of the same mature protease when processed from an unmodified full-length enzyme by a *Bacillus* host cell grown under the same conditions. The level of production is determined by the level of activity of the secreted enzyme.

One measure of production can be determined as relative activity, which is expressed as a percent of the ratio of the value of the enzymatic activity of the mature form when processed from the modified protease to the value of the enzymatic activity of the mature form when processed from the unmodified precursor protease. A relative activity equal or greater than 100% indicates that the mature form a protease that is processed from a modified precursor is produced at a level that is equal or greater than the level at which the same mature protease is produced but when processed from an unmodified precursor. Thus, in some embodiments, the relative activity of a mature protease processed from the modified protease is at least about 100%, at least about 110%, at least about 120%, at least about 130%, at least about 140%, at least about 150%, at least about 160%, at least about 170%, at least about 180%, at least about 190%, at least about 200%, at least about 225%, at least about 250%, at least about 275%, at least about 300%, at least about 325%, at least about 350%, at least about 375%, at least about 400%, at least about 425%, at least about 450%, at least about 475%, at least about 500%, at least about 525%, at least about 550%, at least about 575%, at least about 600%, at least about 625%, at least about 650%, at least about 675%, at least about 700%, at least about 725%, at least about 750%, at least about 800%, at least about 825%, at least about 850%, at least about 875%, at least about 850%, at least about 875%, at least about 900%, and up to at least about 1000% or more when compared to the corresponding production of the mature form of the protease that was processed from the unmodified precursor protease. Alternatively, the relative activity is expressed as the ratio of production which is determined by dividing the value of the activity of the protease processed from a modified precursor by the value of the activity of the same protease when processed from an unmodified precursor. Thus, in some embodiments, the ratio of production of a mature protease processed from a modified precursor is at least about 1, at least about 1.1, at least about 1.2, at least about 1.3 at least about, 1.4, at least about 1.5, at least about 1.6, at least about 1.7, at least about 1.8, at least about 1.9, at least about 2, at least about 2.25, at least about 2.5, at least about 2.75, at least about 3, at least about 3.25, at least about 3.5, at least about 3.75, at least about, at least about 4.25, at least about 4.5, at least about 4.75, at least about 5, at least about 5.25, at least about 5.5, at least about 5.75, at least about 6, at least about 6.25, at least about 6.5, at least about 6.75, at least about 7, at least about 7.25, at least about 7.5, at least about 8, at least about 8.25, at least about 8.5, at least about 8.75, at least about 9, and up to at least about 10.

There are various assays known to those of ordinary skill in the art for detecting and measuring activity of proteases. In particular, assays are available for measuring protease activity that are based on the release of acid-soluble peptides from casein or hemoglobin, measured as absorbance at 280 nm or colorimetrically using the Folin method (See e.g., Bergmeyer et al., "Methods of Enzymatic Analysis" vol. 5, *Peptidases, Proteinases and their Inhibitors*, Verlag Chemie, Weinheim, 1984). Some other assays involve the solubilization of chromogenic substrates (See e.g., Ward, "Proteinases," in Fogarty (ed.), *Microbial Enzymes and Biotechnology*, Applied Science, London, 1983, pp 251-317). Other exemplary assays include, but are not limited to succinyl-Ala-Ala-Pro-Phe-para nitroanilide assay (SAAPFpNA) and the 2,4,6-trinitrobenzene sulfonate sodium salt assay (TNBS assay). Numerous additional references known to those in the art provide suitable methods (See e.g., Wells et al., Nucleic Acids Res. 11:7911-7925, 1983; Christianson et al., Anal. Biochem., 223:119-129, 1994 and Hsia et al., Anal Biochem., 242:221-227, 1999). It is not intended that the present invention be limited to any particular assay method(s).

Other means for determining the levels of production of a mature protease in a host cell include, but are not limited to methods that use either polyclonal or monoclonal antibodies specific for the protein. Examples include, but are not limited to enzyme-linked immunosorbent assays (ELISA), radioimmunoassays (RIA), fluorescent immunoassays (FIA), and fluorescent activated cell sorting (FACS). These and other assays are well known in the art (See e.g., Maddox et al., J. Exp. Med., 158:1211, 1983).

Methods for Producing Mature Proteases

In another aspect, the invention provides a method for producing a mature protease in a *Bacillus* sp. host cell, said method comprising:
a) providing the expression vector of the invention;
b) transforming a *Bacillus* sp. host cell with said expression vector; and
c) culturing said host cell under suitable conditions such that said mature protease is produced by said host cell.

In one aspect, the invention provides a method for producing a mature protease in a *Bacillus* sp. host cell, said method comprising:
a) providing the host cell of the invention;
b) culturing said host cell under suitable conditions such that said mature protease is produced by said host cell.

In some embodiments of the method, said *Bacillus* sp. host cell is a *Bacillus subtilis* host cell.

In some embodiments of the method, said mature protease is a wild-type *Bacillus gibsonii*-clade serine protease, a variant, or a homolog thereof.

In some embodiments of the method, said mature protease is expressed at a higher level than by a host cell comprising an expression vector or modified chromosome which comprises the same first polynucleotide region and third polynucleotide region but a second polynucleotide region encoding a wild-type propeptide region of the *B. gibsonii*-clade protease encoded by the third polynucleotide region.

In some embodiments of the method, said second polynucleotide region encodes a variant propeptide region of a subtilisin from *Bacillus lentus* or a related species thereof, and wherein said mature protease is expressed at a higher level than by a host cell comprising an expression vector or modified chromosome which comprises the same first polynucleotide region and third polynucleotide region but a second polynucleotide region encoding a wild-type propeptide region of the same subtilisin from *Bacillus lentus* or a related species thereof.

In some embodiments of the method, the produced mature protease begins with two glutamines. In some embodiments, the produced mature protease has at least 90%, 95%, 96%, 97%, 98%, or 99% identity to SEQ ID NO: 11 or 12. In some embodiments, the produced mature protease comprises the sequence of SEQ ID NO: 11 or 12.

Polypeptides

In another aspect, the invention provides polypeptides encoded by the polynucleotides of the invention, or polypeptides comprising modified proteases as described herein.

In some embodiments, the polypeptide comprises a modified protease, said protease comprising the propeptide region of a heterologous *Bacillus* protease operably linked to the mature region of a *Bacillus gibsonii*-clade protease, wherein said propeptide region comprises an amino acid sequence with at least 40% identity to SEQ ID NO: 8.

In some embodiments, the polypeptide comprises a modified protease, said modified protease comprising the propeptide region of a heterologous *Bacillus* protease operably linked to the mature region of a *Bacillus gibsonii*-clade protease, wherein said heterologous *Bacillus* protease is from *Bacillus lentus* or a related species thereof.

In some embodiments, the propeptide region is linked to the amino terminus of the mature region.

In some embodiments, said heterologous *Bacillus* protease is from *Bacillus lentus* or a related species thereof.

In some embodiments, said heterologous *Bacillus* protease is from a *Bacillus* species selected from the group consisting of *Bacillus lentus*, *Bacillus clausii*, *Bacillus alcalophilus*, *Bacillus lehensis*, and *Bacillus novalis*.

In some embodiments, said heterologous *Bacillus* protease is from *Bacillus lentus*.

In some embodiments, said heterologous *Bacillus* protease is a serine protease or subtilisin.

In some embodiments, said propeptide region is a wild-type propeptide region of a subtilisin from *Bacillus lentus* or a related species thereof.

In some embodiments, said propeptide region is a variant propeptide region of a subtilisin from *Bacillus lentus* or a related species thereof.

In some embodiments, said heterologous *Bacillus* protease is selected from the group consisting of BspQ01211, Bps02592, *B. lentus*_P29600, BspAL03240, Bpan01744, *B. clausii*_P41362, *B. lehensis*_AFK08970, Bps02003, Bohn00569, BspAK01305, Bpan04382, and BspAL03279.

In some embodiments, said heterologous *Bacillus* protease is selected from the group consisting of BspQ01211, Bps02592, *B. lentus*_P29600, BspAL03240, *B. clausii*_P41362, *B. lehensis*_AFK08970 and Bpan01744.

In some embodiments, said heterologous *Bacillus* protease is *B. lentus*_P29600.

In some embodiments, said propeptide region comprises an amino acid sequence with at least 50% identity to SEQ ID NO: 8.

In some embodiments, said propeptide region comprises an amino acid sequence with at least 75% identity to SEQ ID NO: 8.

In some embodiments, said propeptide region comprises an amino acid sequence with at least 90% identity to SEQ ID NO: 8.

In some embodiments, said propeptide region comprises the sequence of SEQ ID NO: 8.

In some embodiments, said propeptide region is a variant propeptide region of a subtilisin from *Bacillus lentus* or a related species thereof, wherein the variant propeptide region comprises at least one amino acid substitution at a position corresponding to position 6, 30, or 32 of SEQ ID NO: 8

In some embodiments, said at least one amino acid substitution is at the position corresponding to position 6 of SEQ ID NO: 8, and is selected from the group consisting of E6A, E6C, E6R, E6N, E6Q, E6G, E6H, E6I, E6L, E6K, E6M, E6F, E6P, E6S, E6T, E6W, E6Y, and E6V.

In some embodiments, said at least one amino acid substitution is at the position corresponding to position 30 of SEQ ID NO: 8, and is selected from the group consisting of E30A, E30R, E30N, E30D, E30C, E30Q, E30G, E30H, E30L, E30K, E30M, E30S, E30T, E30W, E30Y, and E30V.

In some embodiments, said at least one amino acid substitution is at the position corresponding to position 32 of SEQ ID NO: 8, and is selected from the group consisting of A32R, A32N, A32C, A32Q, A32G, A32H, A32I, A32L, A32K, A32M, A32F, A32P, A32S, A32T, A32W, A32Y, and A32V.

In some embodiments, said propeptide region comprises the sequence set forth in SEQ ID NO: 8 with the proviso that said propeptide region comprises at least one amino acid substitution at positions chosen from positions 6, 30 and 32 of SEQ ID NO: 8.

In some embodiments, said propeptide region comprises an amino acid substitution at position 6 of SEQ ID NO: 8 selected from the group consisting of E6A, E6C, E6R, E6N, E6Q, E6G, E6H, E6I, E6L, E6K, E6M, E6F, E6P, E6S, E6T, E6W, E6Y, and E6V.

In some embodiments, said propeptide region comprises an amino acid substitution at position 30 of SEQ ID NO: 8 selected from the group consisting of E30A, E30R, E30N, E30D, E30C, E30Q, E30G, E30H, E30L, E30K, E30M, E30S, E30T, E30W, E30Y, and E30V.

In some embodiments, said propeptide region comprises an amino acid substitution at position 32 of SEQ ID NO: 8 selected from the group consisting of A32R, A32N, A32C, A32Q, A32G, A32H, A32I, A32L, A32K, A32M, A32F, A32P, A32S, A32T, A32W, A32Y, and A32V.

In some embodiments, the polypeptide comprising a modified protease, said modified protease comprising a variant propeptide region of a first *Bacillus gibsonii*-clade protease operably linked to the mature region of a second *Bacillus gibsonii*-clade protease.

In some embodiments, said first *Bacillus gibsonii*-clade protease or said second *Bacillus gibsonii*-clade protease is a serine protease or subtilisin.

In some embodiments, said first *Bacillus gibsonii*-clade protease and said second *Bacillus gibsonii*-clade protease are from the same *Bacillus* species.

In some embodiments, said first *Bacillus gibsonii*-clade protease and said second *Bacillus gibsonii*-clade protease are from different *Bacillus* species.

In some embodiments, said variant propeptide region comprises an amino acid sequence with at least 60% identity to SEQ ID NO: 7.

In some embodiments, said variant propeptide region comprises an amino acid sequence with at least 90% identity to SEQ ID NO: 7.

In some embodiments, said variant propeptide region comprises the propeptide region set forth in SEQ ID NO: 7 with the proviso that said propeptide region comprises an amino acid substitution at position 34 of SEQ ID NO: 7.

In some embodiments, said amino acid substitution enhances the production of said mature region of the second *Bacillus gibsonii*-clade protease by a *Bacillus* sp. host cell.

In some embodiments, said *Bacillus* sp. host cell is a *Bacillus subtilis* host cell.

In some embodiments, said amino acid substitution at position 34 of SEQ ID NO: 7 is selected from the group consisting of E34D, E34C, E34G, E34H, E34S, and E34V.

In some embodiments, said heterologous or variant propeptide region comprises an amino acid sequence set forth in SEQ ID NO: 44.

In some embodiments, said heterologous or variant propeptide region comprises an amino acid sequence set forth in SEQ ID NO: 69.

In some embodiments of the polypeptide, the mature region of the modified protease is described herein.

In some embodiments, the polypeptide further comprises a signal peptide as described herein. In some embodiments, the signal peptide is suitable for secreting proteins in *Bacillus* sp. In some embodiments, the signal peptide is suitable for secreting proteins in *Bacillus subtilis.*

All publications and patents mentioned herein are herein incorporated by reference. Various modifications and variations of the described method and system of the invention will be apparent to those skilled in the art without departing from the scope and spirit of the invention. Although the invention has been described in connection with specific embodiments, it should be understood that the invention as should not be unduly limited to such specific embodiments. Indeed, various modifications of the described modes for carrying out the invention that are obvious to those skilled in the art and/or related fields are intended to be within the scope of the present invention.

EXPERIMENTAL

In the experimental disclosure which follows, the following abbreviations apply: ppm (parts per million); M (molar); mM (millimolar); μM (micromolar); nM (nanomolar); mol (moles); mmol (millimoles); μmol (micromoles); nmol (nanomoles); gm (grams); mg (milligrams); μg (micrograms); pg (picograms); L (liters); ml and mL (milliliters); μl and μL (microliters); cm (centimeters); mm (millimeters); μm (micrometers); nm (nanometers); U (units); V (volts); MW (molecular weight); sec (seconds); min(s) (minute/minutes); h(s) and hr(s) (hour/hours); ° C. (degrees Centigrade); QS (quantity sufficient); QC (QuikChange), ND (not done); NA (not applicable); rpm (revolutions per minute); w/v (weight to volume); v/v (volume to volume); g (gravity); OD (optical density); aa (amino acid); bp (base pair); kb (kilobase pair); kD (kilodaltons); suc-AAPF-pNA (succinyl-L-alanyl-L-alanyl-L-prolyl-L-phenyl-alanyl-para-nitroanilide); DMSO (dimethyl sulfoxide); cDNA (copy or complementary DNA); DNA (deoxyribonucleic acid); ssDNA (single stranded DNA); dsDNA (double stranded DNA); dNTP (deoxyribonucleotide triphosphate); DTT (1,4-dithio-DL-threitol); $H_2O$ (water); dH2O (deionized water); HCl (hydrochloric acid); $MgCl_2$ (magnesium chloride); MOPS (3-[N-morpholino]propanesulfonic acid); NaCl (sodium chloride); PAGE (polyacrylamide gel electrophoresis); PBS (phosphate buffered saline [150 mM NaCl, 10 mM sodium phosphate buffer, pH 7.2]); PEG (polyethylene glycol); PCR (polymerase chain reaction); PMSF (phenylmethylsulfonyl fluoride); RNA (ribonucleic acid); SDS (sodium dodecyl sulfate); Tris (tris(hydroxymethyl)aminomethane); SOC (2% Bacto-Tryptone, 0.5% Bacto Yeast Extract, 10 mM NaCl, 2.5 mM KCl); Terrific Broth (TB; 12 g/l Bacto Tryptone, 24 g/l glycerol, 2.31 g/l $KH_2PO_4$, and 12.54 g/l $K_2HPO_4$); OD280 (optical density at 280 nm); OD600 (optical density at 600 nm); A405 (absorbance at 405 nm); Vmax (the maximum initial velocity of an enzyme catalyzed reaction); HEPES (N-[2-Hydroxyethyl] piperazine-N-[2-ethanesulfonic acid]); Tris-HCl (tris[Hydroxymethyl]aminomethane-hydrochloride); TCA (trichloroacetic acid); HPLC (high pressure liquid chromatography); RP-HPLC (reverse phase high pressure liquid chromatography); TLC (thin layer chromatography); EDTA (ethylenediaminetetracetic acid); EtOH (ethanol); SDS (sodium dodecyl sulfate); Tris (tris(hydroxymethyl) aminomethane); TAED (N,N,N'N'-tetraacetylethylenediamine).

The following examples are provided in order to demonstrate and further illustrate certain embodiments and aspects of the present invention and are not to be construed as limiting the scope thereof.

Example 1

Methods
AAPF Assay of Protease Activity

B. subtilis cultures obtained as described below were assayed for the production of active subtilisin protease as a measure of protease expression. The enzymes produced were assayed for activity against the synthetic substrate succinyl-L-Ala-L-Ala-L-Pro-L-Phe-p-nitroanalide (AAPF). The assay measures the production of active protease as the increase in absorbance at 405 nm over time, resulting from the hydrolysis and release of p-nitroanaline (Estell et al., J. Biol. Chem., 260:6518-6521, 1985). B. subtilis culture supernatants were diluted appropriately in Tris Buffer, containing 10 mM Tris+0.005% TWEEN®-80, pH 8.6. Reactions were prepared by adding the diluted culture supernatant to 25 uL AAPF substrate (1 mg/ml AAPF in the above described Tris Buffer). The kinetic assay was run on a 96 well plate reader (Spectramax, Molecular Devices, Sunnyvale, Calif., USA) for 2 minutes resulting in a linear response.

Cultivation of B. subtilis for Isolation of Protease Samples

Bacterial colonies harboring the control plasmid or a plasmid encoding a modified protease were used to inoculate 150 uL of Luria Broth containing with 5 ppm chloramphenicol (CMP) in wells of a microtiter plate (MTP). The MTPs were then incubated for 4 hours at 37° C. while rotating at 250 rpm. 10 ul of each of the cultures were transferred to a new MTP containing 160 ul of Bacillus culture media described below, at pH 7.6, and the cultures were grown in a shaking incubator at 31° C., at 270 rpm for 68 hours. The Bacillus culture media was an enriched semi-defined media based on MOPs buffer, with urea as major nitrogen source, glucose as the main carbon source, and supplemented with 1% soytone for robust cell growth. Following the incubation period, the MTPs were centrifuged and the supernatant of each of the cultures was assayed for protease activity using the AAPF assay described above.

Example 2

Figure 2:
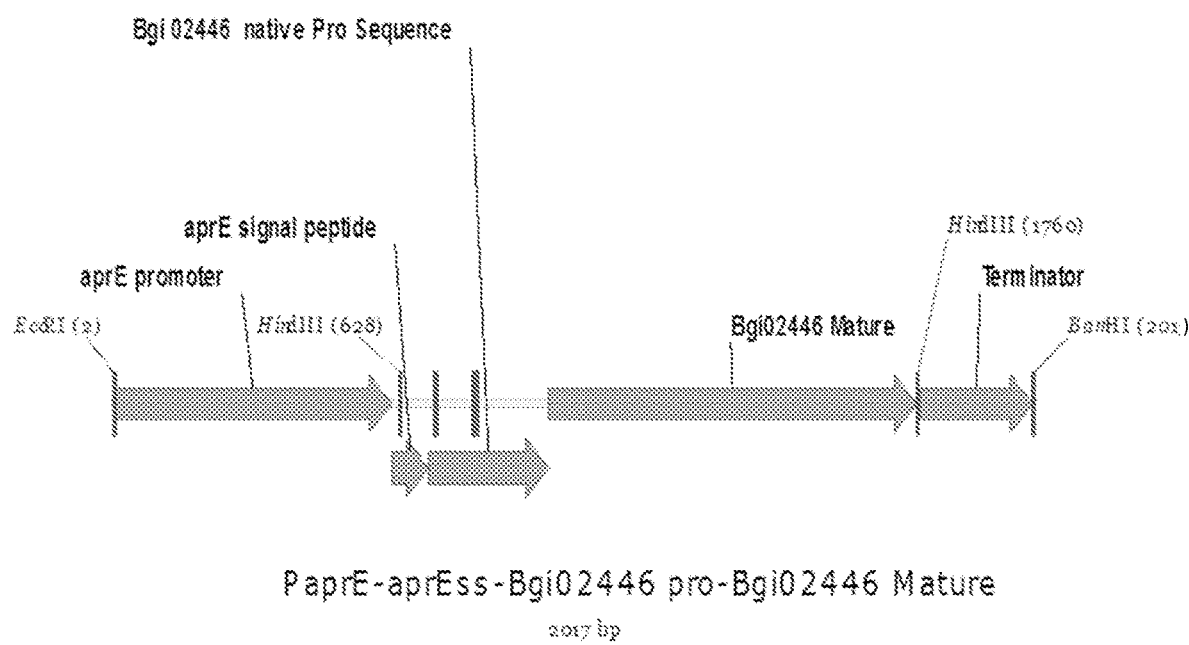
FIG. 2 shows a diagram of the gene cassette used for the expression of the mature region of Bgi02446, a *B. gibsonii* serine protease (subtilisin), using the native Bgi02446 propeptide sequence.

Expression of Bacillus gibsonii Bgi02446 Mature Subtilisin Using Either the Native Bgi02446 Propeptide Sequence or a Heterologous Propeptide Sequence from B. lentus Subtilisin A DNA cassette comprising B. subtilis aprE promoter (SEQ ID NO:1), the B. subtilis aprE signal peptide (SEQ ID NO:2), the Bgi02446 pro sequence (SEQ ID NO:3), the Bacillus gibsonii Bgi02446 mature gene (SEQ ID NO: 4) and the B. lentus terminator (SEQ ID NO: 39) was synthesized by GeneArt, Life Technologies (Carlsbad, Calif.). FIG. 2 depicts the gene cassette used for the Bgi02446 subtilisin expression with the Bgi02446 native pro peptide sequence.

The pro-sequence prediction was based on knowledge of the pro-mature junction in homologous serine proteases such as BPN' (Wells et al., Nucleic Acids Res, 11: 7911-7925, 1983), and the PB92 protease (van der Laan et al., Appl Environ Microbiol, 57:901-909, 1991). Expression of Bacillus gibsonii Bgi02446, also known as AprBG, has been reported previously (Deng et al., "Secretory expression, functional characterization, and molecular genetic analysis of novel halo-solvent-tolerant protease from Bacillus gibsonii." J Microbiol Biotechnol. 24:197-208, 2014), and also by Danisco US Inc. in International PCT Publication No. WO2015/089447). The Bgi02446 subtilisin is encoded by the DSM8722 strain, and is also known as AprBG (Deng et al., 2014). This subtilisin, together with homologous enzymes encoded by strains DSM 9728, DSM 9729, DSM 9730 and DSM 9731, all share significant sequence identify and cluster in the same region of a subtilisin phylogenetic tree. They form the basis of the B. gibsonii-clade of subtilisins (PCT Publication No. WO2015/089447).

Figure 3:
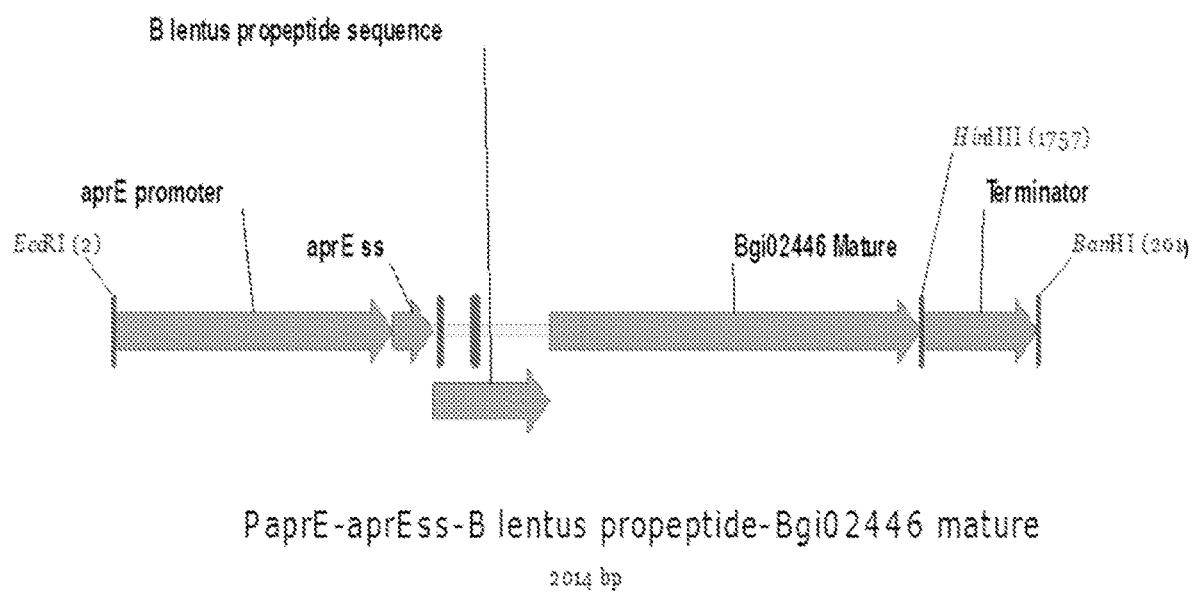
FIG. 3 shows a diagram of the gene cassette used for the expression of the mature region of Bgi02446 using a *B. lentus* subtilisin propeptide sequence.

A DNA cassette comprising the B. subtilis aprE promoter (SEQ ID NO:1), the B. subtilis aprE signal peptide (SEQ ID NO:2), the B. lentus subtilisin pro peptide sequence (SEQ ID NO:5), the Bgi02446 subtilisin mature gene (SEQ ID NO:4) and the B. lentus terminator (SEQ ID NO: 39) was synthesized (GeneArt). FIG. 3 shows the gene cassette used for the Bgi02446 subtilisin expression with, in this case, the B. lentus subtilisin pro peptide sequence.

Both expression cassettes were digested by restriction enzymes EcoRI and HindIII using standard molecular biology protocols.

The chloramphenicol acetyl transferase (CAT) gene expression cassette from S. aureus (SEQ ID NO:6) was also synthesized (DNA 2.0 Menlo Park, Calif.). A diagram of this cassette is shown in FIG. 4. The cassette was digested by restriction enzymes EcoRI and HindIII using standard molecular biology protocols.

The two gene cassettes expressing the Bacillus gibsonii Bgi02446 subtilisin were each ligated to the CAT gene cassette using T4 DNA ligase (New England Biolabs), then a rolling circle amplification (RCA) reaction was performed following the manufacturer's instructions for the kit (Catalog Number 25640010, GE Healthcare). The rolling circle amplification reactions were used to transform 200 ul of competent cells of a suitable B. subtilis strain. The transformed cells were incubated at 37° C. for one hour while shaking at 250 rpm. Cells from the transformation mixture were plated onto agar plates containing 1.6% skim milk under chloramphenicol selection. Single colonies were selected to be grown in Luria broth to optical density of 1.3 at 600 nm. Each strain sample was then frozen at 80° C. with 20% glycerol. The amino acid sequence of the AprE signal peptide from *B. subtilis* encoded by SEQ ID NO:2 is set forth in SEQ ID NO: 40:

Example 3

Expression Levels of *B. gibsonii* Bgi02446 Wildtype Mature Subtilisin when Using the Native *B. gibsonii* Bgi02446 Propeptide Sequence or a Heterologous Propeptide Sequence from the *B. lentus* Subtilisin

*B. subtilis* cultures obtained from the constructs described in Example 2 were used to measure the relative subtilisin activity on samples from each of the strains. Protease activity on the AAPF-pNA substrate was used to detect the relative amounts of subtilisin enzyme expressed by the various constructs evaluated in this and subsequent examples. The results of the comparison of the effect on expression of native *B. gibsonii* Bgi02446 pro peptide versus the heterologous *B. lentus* pro peptide are shown on Table 3. Expression of *Bacillus gibsonii* Bgi02446 subtilisin is significantly enhanced when the pro peptide from a different *Bacillus* subtilisin, in this case the *B. lentus* subtilisin, is used to replace the naturally occurring sequences. The amino acid sequences of these two pro peptides are significantly different, as can be seen on sequence alignment on Example 13 below.

TABLE 3

Effect of *B. lentus* Subtilisin Pro Region on the Production of the Mature Protease Bgi02446

| Construct | % relative subtilisin expression |
|---|---|
| Bgi02446 Pro-Bgi02446 Mature | 100 |
| *B. lentus* Pro-Bgi02446 Mature | 153 |

Subtilisin

The amino acid sequence of the polypeptide encoded by the Bgi02446 pro sequence is set forth in SEQ ID NO:7 and the amino acid sequence of the polypeptide encoded by the *B. lentus* subtilisin pro sequence is set forth in SEQ ID NO:8

Example 4

Expression of *Bacillus gibsonii* Variant BSP-00801 of Mature Subtilisin Using Either the Native Bgi02446 Propeptide Sequence or the Propeptide Sequence from *B. lentus* Subtilisin DNA cassettes comprising *B. subtilis* aprE promoter (SEQ ID NO:1), the *B. subtilis* aprE signal peptide (SEQ ID NO:2), the pro sequence from either *Bacillus gibsonii* Bgi02446 (SEQ ID NO:3) or from *B. lentus* (SEQ ID NO:5), and the sequence corresponding to the gene for a variant of *Bacillus gibsonii* Bgi02446 referred to as BSP-00801 (SEQ ID NO: 9) were synthesized by amplification using primers listed on Table 4. Using techniques known in the art, PCR fragments were assembled using Gibson Assembly (SGI DNA Catalogue Number GA1100-10) to make the final expression cassettes. A rolling circle amplification reaction was performed per manufacturer's instruction (GE Healthcare Catalogue Number 25640010). The rolling circle amplification reaction was used to transform 200 ul of competent cells, of a suitable *B. subtilis* strain. The transformed cells were incubated at 37° C. for one hour while shaking at 250 rpm. Cells from the transformation mixture were plated onto agar plates containing 1.6% skim milk under chloramphenicol selection. Single colonies were selected to be grown in Luria broth to an optical density of 1.3 at 600 nm. Each strain sample was then frozen at −80° C. with 20% glycerol.

TABLE 4

Primers Used for the Construction of Expression Cassettes Encoding *Bacillus gibsonii* Bgi02446 Propeptide or *B. lentus* Propeptide Fusions to *Bacillus gibsonii* Variant BSP-00801 Mature Gene

| Primer | Sequence | SEQ ID |
|---|---|---|
| EL1664 | GAGGATGCAGAAGTAACGACAATGCAACAAACAGTGCCATGG | 15 |
| EL1665 | CCAAGGCCGGTTTTTTATGTATCTAGATTAGCGTGTTGCCGCTTCTGCATTG | 16 |
| EL1666 | GAAGAAGACATTGAACTGTCTATTCAACAAACAGTGCCATGG | 17 |
| EL1667 | CAATGCAGAAGCGGCAACACGCTAATCTAGATACATAAAAAACCGGCCTTGG | 18 |
| EL1668 | CCATGGCACTGTTTGTTGCATTGTCGTTACTTCTGCATCCTC | 19 |
| EL1669 | CCATGGCACTGTTTGTTGAATAGACAGTTCAATGTCTTCTTC | 20 |

Example 5

Expression Levels of *B. gibsonii* Variant BSP-00801 Mature Subtilisin when Using the Native Bgi02446 Propeptide Sequence or a Heterologous Propeptide Sequence from the *B. lentus* Subtilisin

*B. subtilis* cultures obtained from constructs described in Example 4 were used to measure the relative subtilisin activity on samples from each of the strains. Protease activity on the AAPF-pNA substrate is used to detect the relative amounts of *B. gibsonii* variant BSP-00801 subtilisin enzyme expressed by the various constructs evaluated in this and subsequent examples. The results of the comparison of the native *B. gibsonii* Bgi02446 pro peptide versus the heterologous *B. lentus* pro peptide are shown on Table 3. We observe that using the *B. lentus* subtilisin pro peptide sequence (SEQ ID NO:3) in an expression cassette with the BSP-00801 mature gene (SEQ ID NO:9) gives an enhanced productivity of the BSP-00801 protein. The enhanced expression observed when the *B. gibsonii* variant BSP-00801 is expressed using the *B. lentus* pro peptide is similar in magnitude to that observed for the wildtype Bgi02446 *B. gibsonii* pro peptide sequence (see Table 5).

TABLE 5

Effect of *B. lentus* Subtilisin Pro Region on the Production of the Mature Protease BSP-00801 Protein Subtilisin

| Construct | % relative subtilisin expression |
|---|---|
| Bgi02446 Pro - BSP-00801 Mature | 100 |
| *B. lentus* Pro - BSP-00801 Mature | 133 |

Example 6

Confirmation of Mature Protease Sequences

Samples were treated with trichloroacetic acid to precipitate proteins. The protein pellets were dissolved in 8M urea and reduced with dithiothreitol, alkylated with iodoacetamide, and digested using a mixture of trypsin, α-chymotrypsin and endoproteinase GluC. The samples were analyzed using high resolution LC/MS/MS. Samples were subjected to RP-HPLC (Phenomenex Aeris Peptide XB-C18 column on an Acquity HPLC, Waters) and 2-85% acetonitrile gradient with 0.1% formic acid. The system was serially connected to a high resolution tandem mass spectrometer (OrbiTrap XL, Thermo). The polypeptides were identified on proteomics database searching software, Proteome Discoverer 1.4.

The amino acid sequence of the Bgi02446 mature protein isolated from expression system using the native Bgi02446 pro peptide is set forth in SEQ ID NO: 10. The 268 amino acid polypeptide with one glutamine (Q) at the N-terminus coincides with previously observed Bgi02446 mature protein (reported by Deng et al., 2014 and by Danisco US Inc. as SEQ ID NO: 7 in PCT Publication No. WO2015/089447). Pro-sequence predictions based on knowledge of the pro-mature junction in homologous serine proteases such as BPN' (Wells et al., *Nucleic Acids Res,* 11: 7911-7925, 1983) and PB92 protease (van der Laan et al., *Appl Environ Microbiol,* 57:901-909, 1991) had predicted a 269 amino acid mature Bgi02446 protein having two glutamines (QQ) at the N-terminus, but instead only one glutamine (Q) was observed.

The 269 amino acid sequence of the Bgi02446 mature protein isolated from expression system using the heterologous *B. lentus* propeptide is set forth in SEQ ID NO: 11. It is interesting to find that this sequence of the mature Bgi02446 subtilisin obtained when using the heterologous *B. lentus* propeptide is different from the one obtained when using the native/homologous Bgi02446 propeptide. In the case of the heterologous expression cassette, the 269 amino acid Bgi02446 subtilisin has the predicted N-terminus, and is not further processed.

Samples of the *B. gibsonii* variant BSP-00801 subtilisin were also analyzed by LC/MS as described above. Similar to the Bgi02446 mature protein, the BSP-00801 subtilisin variant also had a different N-terminus depending on which propeptide was used in the expression cassette. Like Bgi02446, the BSP-00801 subtilisin variant showed two glutamines (QQ) at the N-terminus when expressed using the heterologous *B. lentus* propeptide (SEQ ID NO: 12) and one glutamine (Q) at the N-terminus when expressed using the parental Bgi02446 propeptide (SEQ ID NO: 13).

Example 7

Construction of a *B. lentus* Propeptide Site Evaluation Library for Expression of Bgi02446 Subtilisin A site evaluation library (SEL) at several amino acid positions of the *B. lentus* subtilisin propeptide was generated in order to evaluate the impact on expression of Bgi02446 subtilisin. These SELs were generated using standard molecular biology protocols. A template plasmid containing a DNA cassette comprising *B. subtilis* aprE promoter (SEQ ID NO:1), the *B. subtilis* aprE signal peptide (SEQ ID NO:5), and the Bgi02446 mature gene (SEQ ID NO:4) was constructed and called pKB723-Bgi02446 (FIG. 5). The forward and reverse NNS oligomers (listed in Table 6) for each amino acid site in the site saturation library and the outside primers (listed in Table 7) were used to hybridize the start or end of the expression cassette, which were obtained from Eurofins Genomics (Huntsville, Ala., USA).

A polymerase chain reaction with appropriate primer pairs and the template plasmid was performed using PFU Ultra II polymerase (Agilent Technologies Inc.). The PCR was carried out using 40 uL of $H_2O$, 5 uL of PFU Ultra II 10× buffer, 1 uL dNTP mix (Roche), 1 ul of each primer (5 uM concentration) and 1 ul of the DNA template. It was incubated in a thermocycler using the following conditions: 95° C. for 2 minutes, once, followed by 30 cycles of 95° C. for 20 seconds, 55° C. for 20 seconds, and 72° C. for 30 seconds, then 1 cycle of 72° C. for 3 minutes. The PCR fragments were assembled using Gibson Assembly (SGI DNA Catalog Number GA1100-10) in a reaction consisting of 1.5 uL of each PCR reaction+8 ul 2× Master Mix+5 uL $H_2O$, incubated in a thermocycler at 50° C. for 80 minutes, then incubated at 65° C. for 10 minutes and cooled to 4° C.

Suitable *B. subtilis* competent cells were transformed with the assembled DNA. The transformed cells were incubated at 37° C. for 1 hour while shaking at 250 rpm. Cells from the transformation mixture were plated onto agar plates containing 1.6% skim milk under chloramphenicol selection. Single colonies were selected to be grown in Luria broth to optical density of 1.3 at 600 nm. Each strain sample was then frozen at 80° C. with 20% glycerol.

Each variant was confirmed by DNA sequence analysis. To generate Bgi02446 subtilisin protease samples for analysis, selective growth of the variants was performed in 96 well MTPs at 31° C. for 68 hours in cultivation medium (enriched semi-defined media based on MOPs buffer, with urea as major nitrogen source, glucose as the main carbon source, and supplemented with 1% soytone for robust cell growth) in each well. At the end of incubation, each of the cultures was assayed for protease activity using the AAPF assay described below.

TABLE 6

NNS Primer Sequences Used to Mutate Sites 6, 30, and 32 of the *B. lentus* Subtilisin Propeptide Sequence

| Primer | Sequence | SEQ ID NO: |
|---|---|---|
| Site 6 Forward | GCTGCTGAAGAAGCAAAANNSAAATATTTAATTGGCTTTAATG | 21 |
| Site 6 Reverse | CATTAAAGCCAATTAAATATTTSNNTTTTGCTTCTTCAGCAGC | 22 |
| Site 30 Forward | CAAGTAGAGGCAAATGACNNSGTCGCCATTCTCTCTGAG | 23 |
| Site 30 Reverse | CTCAGAGAGAATGGCGACSNNGTCATTTGCCTCTACTTG | 24 |
| Site 32 Forward | GAGGCAAATGACGAGGTCNNSATTCTCTCTGAGGAAGAG | 25 |
| Site 32 Reverse | CTCTTCCTCAGAGAGAATSNNGACCTCGTCATTTGCCTC | 26 |

TABLE 7

Outside Primer Sequences Used in Conjunction with the NNS Primers

| Primer | Sequence | SEQ ID NO: |
|---|---|---|
| Forward | GATAGAGCTGGGTAAAGCCTATGAATTCTCCATTTTCTTCTGCTATC | 27 |
| Reverse | ATAGGCTTTACCCAGCTCTATCACAAACGAAAATTGGATAAAGTG | 28 |

Example 8

Effect of Mutations at Positions 6, 30 and 32 of the *B. lentus* Propeptide on the Expression of Bgi02446 Wildtype Subtilisin Aliquots of culture supernatants from expression of the *B. lentus* propeptide SEL and Bgi02446 mature subtilisin were assayed as described above in Example 1 for AAPF activity. The relative expression of the active (mature) Bgi02446 subtilisin was calculated for each expression plasmid, using the wildtype *B. lentus* propeptide as the reference. The positions mutated correspond to 6, 30 and 32 of the *B. lentus* propeptide linear sequence (SEQ ID NO: 8). Table 8 lists the results for variants at position 6 of the *B. lentus* propeptide that show an increase in expression over the wildtype sequence, Table 9 lists the results for variants at position 30 of the *B. lentus* propeptide that show an increase in expression over the wildtype sequence and Table 10 lists the results for variants at position 32 of the *B. lentus* pro peptide that show an increase in expression over the wildtype sequence.

TABLE 8

Effect of Amino Acid Substitutions at position 6 of the *B. lentus* Subtilisin Propeptide Region on the Production of Bgi02446 Mature Protease

| Substitutions at Position 6 in Propeptide Region | Percent Relative Protease Expression |
|---|---|
| E6 (Control) | 100 |
| E6A | 310 |
| E6R | 310 |

TABLE 8-continued

Effect of Amino Acid Substitutions at position 6 of the *B. lentus* Subtilisin Propeptide Region on the Production of Bgi02446 Mature Protease

| Substitutions at Position 6 in Propeptide Region | Percent Relative Protease Expression |
|---|---|
| E6N | 180 |
| E6Q | 442 |
| E6G | 361 |
| E6H | 193 |
| E6I | 236 |
| E6L | 361 |
| E6K | 242 |
| E6M | 332 |
| E6F | 259 |
| E6P | 134 |
| E6S | 253 |
| E6T | 220 |
| E6W | 157 |
| E6Y | 178 |
| E6V | 320 |

TABLE 9

Effect of Amino Acid Substitutions at Position 30 of the *B. lentus* Subtilisin Pro Region on the Production of Bgi02446 Mature Protease

| Substitutions at Position 30 in Propeptide Region | Percent Relative Protease Expression |
|---|---|
| E30 (Control) | 100 |
| E30A | 233 |
| E30R | 301 |
| E30N | 293 |

TABLE 9-continued

Effect of Amino Acid Substitutions at Position 30 of the *B. lentus* Subtilisin Pro Region on the Production of Bgi02446 Mature Protease

| Substitutions at Position 30 in Propeptide Region | Percent Relative Protease Expression |
|---|---|
| E30D | 456 |
| E30C | 322 |
| E30Q | 172 |
| E30G | 178 |
| E30H | 346 |
| E30L | 251 |
| E30K | 295 |
| E30M | 312 |
| E30S | 359 |
| E30T | 433 |
| E30W | 325 |
| E30Y | 101 |
| E30V | 153 |

TABLE 10

Effect of Amino Acid Substitutions at Position 32 of the *B. lentus* Subtilisin Pro Region on the Production of Bgi02446 Mature Protease

| Substitutions at Position 32 in Propeptide Region | Percent Relative Protease Expression |
|---|---|
| A32 (Control) | 100 |
| A32R | 258 |
| A32N | 166 |
| A32C | 478 |
| A32Q | 154 |
| A32G | 309 |
| A32H | 259 |
| A32I | 464 |
| A32L | 178 |
| A32K | 285 |
| A32M | 290 |
| A32F | 302 |
| A32P | 165 |
| A32S | 273 |

TABLE 10-continued

Effect of Amino Acid Substitutions at Position 32 of the *B. lentus* Subtilisin Pro Region on the Production of Bgi02446 Mature Protease

| Substitutions at Position 32 in Propeptide Region | Percent Relative Protease Expression |
|---|---|
| A32T | 282 |
| A32W | 497 |
| A32Y | 359 |
| A32V | 378 |

Example 9

Construction of a *B. lentus* Propeptide Site Evaluation Library for Expression of *B. gibsonii* BSP-00801 Variant Subtilisin Mutations were introduced at amino acid positions 6, 30 or 32 of the *B. lentus* propeptide linear sequence (SEQ ID NO:8) of the *B. gibsonii* BSP-00801 variant expression construct (see, FIG. 5) using the primers listed in Table 11 and standard PCR and assembly PCR techniques (e.g., Sambrook et al., Molecular Cloning: Cold Spring Harbor Laboratory Press). The resulting PCR fragments were circularized by ligation and transformed into a suitable *Bacillus subtilis* strain. Individual mutations were subsequently identified by DNA sequencing. The strains harboring the various *B. lentus* propeptide mutations (substitutions) were grown in liquid media with increasing concentrations of chloramphenicol in order to force amplification of the expression construct on the chromosome.

Following the amplification procedure, the strains were grown for 68 hours at 31° C. in *Bacillus* culture media (described in Example 1) containing 5 mM $CaCl_2$ and 5 ug/ml chloramphenicol. The culture supernatant was harvested and the amount of BSP-00801 protease was determined using the AAPF activity assay described in Example 1.

TABLE 11

Primers Used in Construction of *B. lentus* Propeptide-BSP-00801 Mature Expression Cassettes

| Primer | Sequence | SEQ ID |
|---|---|---|
| AprE promoter primer US | 5'(P)-GAATTCTCCATTTTCTTCTGCTATCAAAATAACAGACTCGTG | 29 |
| CAT Promoter primer LS | 5'(P)-ACAAACGAAAATTGGATAAAGTGGGATATTTTTAAAATATATATTTATGTTACAGTAATATTGAC | 30 |
| Site-6 B; lentus pro US | 5'-GGCTGCTGAAGAAGCAAAANNSAAATATTTAATTGGCTTTAATGAGC | 31 |
| Site-6 B; lentus pro LS | 5'-GCTCATTAAAGCCAATTAAATATTTSNNTTTTGCTTCTTCAGCAGCC | 32 |
| Site-30 B; lentus pro US | 5'-GAACAAGTAGAGGCAAATGACNNSGTCGCCATTCTCTCTGAG | 33 |
| Site-30 B; lentus pro LS | 5'-CTCAGAGAGAATGGCGACSNNGTCATTTGCCTCTACTTGTTC | 34 |
| Site-32 B; lentus pro US | 5'-GAGGCAAATGACGAGGTCNNSATTCTCTCTGAGGAAGAGG | 35 |
| Site-32 B; lentus pro LS | 5'-CCTCTTCCTCAGAGAGAATSNNGACCTCGTCATTTGCCTC | 36 |

SEQ ID NO:14 (set forth below) comprises the nucleotide sequence of the expression cassette including the *B. lentus* propeptide and BSP-00801 subtilisin variant open reading frame (ORF). The aprE signal sequence is underlined, the *B. lentus* propeptide sequence is italicized and the nucleotide sequence of the mature BSP-00801 subtilisin is capitalized.

(SEQ ID NO: 14)
<u>gtgagaagcaaaaaattgtggatcagcttgttgtttgcgttaacgttaat</u>

<u>ctttacgatggcgttcagcaacatgtctgcgcaggct</u>*gctgaagaagcaa*

*aagaaaaatatttaattggctttaatgagcaggaagctgtcagtgagttt*

*gtagaacaagtagaggcaaatgacgaggtcgccattctctctgaggaaga*

*ggaagtcgaaattgaattgcttcatgaatttgaaacgattcctgttttat*

*ccgttgagttaagcccagaagatgtggacgcgcttgaactcgatccagcg*

*atttcttatattgaagaggatgcagaagtaacgacaatg*CAACAAACAGT

GCCATGGGGAATTACTCGTGTGCAAGCCCCAGCTGTTCATAACCGTGGAA

TTACAGGTTCTGGTGTAAGAGTTGCTATCCTCGATTCAGGTATTTCCACA

CATGAAGACTTAAATGTTCGTGGTGGCGTTAGCTTTGTACCAGGGGAACC

AACGACTGCTGATTTAAATGGGCATGGCACGCATGTGGCTGGGACGGTAG

CTGCTTTAAACAATTCGATTGGCGTTGTTGGCGTAGCACCGTCAGCGGAT

CTATACGCTGTTAAAGTATTAGGGGCGAATGGTAGAGGTTCGGTCAGCGG

GATTGCCCAAGGATTGGAATGGGCAGCAGCAAATAACATGCACATTGCTA

ATATGAGTTTAGGAAGCGATGCACCAAGTTCTACACTTGAGCGTGCTGTT

AATTATGCGACTTCTAGAGATGTTCTTGTTATTGCGGCAACTGGGAATAA

CGGTTCTGGCTCAGTAGGCTATCCGGCCCGTTATGCGAACGCAATGGCAG

TCGGAGCTACTGACCAAAACAACAGACGCGCCAACTTTTCACAGTATGGC

ACGGGGATTGACATTGTCGCACCAGGTGTAAACGTGCAGAGCACATACCC

AGGTAACCGTTATGTGAGCATGAACGGTACATCGATGGCTACTCCTCATG

TTGCAGGTGCAGCAGCCCTTGTTAAACAACGCTATCCATCTTGGAATGCG

ACTCAAATCCGCAATCATCTAAAGAATACGGCAACGAATTTAGGAAACTC

TTCACAATTTGGAAGCGGACTTGTCAATGCAGAAGCGGCAACACGC

Example 10

Effect of Mutations at Amino Acid Positions 6, 30 and 32 of the *B. lentus* Propeptide on the Expression of BSP-00801 Variant Subtilisin Aliquots of culture supernatants from expression of the *B. lentus* pro peptide SEL and *B. gibsonii* variant BSP-00801 mature subtilisin were assayed as described on Example 1 for AAPF activity. The relative expression of the active (mature) BSP-00801 subtilisin was calculated for each expression plasmid, using the wildtype *B. lentus* propeptide as the reference. The positions mutated (substituted) correspond to positions 6, 30 and 32 of the *B. lentus* propeptide linear sequence (SEQ ID NO:8). Table 12 lists the results for variants at position 6 of the *B. lentus* propeptide that show an increase in expression over the wildtype sequence, Table 13 lists the results for variants at position 30 of the *B. lentus* pro peptide that show an increase in expression over the wildtype sequence and Table 14 lists the results for variants at position 32 of the *B. lentus* pro peptide that show an increase in expression over the wildtype sequence.

TABLE 12

Expression Levels Comparison of BSP-00801 Mature Subtilisin for Variants at Position 6 of the *B. lentus* Propeptide

| Substitutions at Position 6 in Propeptide Region | Percent Relative Protease Expression |
|---|---|
| E006 (control) | 100 |
| E006A | 100 |
| E006C | 120 |
| E006G | 114 |
| E006K | 122 |
| E006M | 100 |
| E006Q | 110 |
| E006R | 133 |
| E006S | 102 |
| E006V | 123 |

TABLE 13

Expression Levels Comparison of BSP-00801 Mature Subtilisin for Variants at Position 30 of the *B. lentus* Propeptide

| Substitutions at Position 30 in Propeptide Region | Percent Relative Protease Expression |
|---|---|
| E030 (control) | 100 |
| E030A | 125 |
| E030C | 112 |
| E030D | 140 |
| E030G | 150 |
| E030H | 104 |
| E030K | 125 |
| E030M | 110 |
| E030N | 125 |
| E030R | 100 |
| E030S | 115 |
| E030T | 110 |
| E030W | 115 |
| E030Y | 105 |

TABLE 14

Expression levels comparison of BSP-00801 mature subtilisin for variants at position 32 of the *B. lentus* pro peptide

| Substitutions at Position 32 in Propeptide Region | Percent relative protease expression |
|---|---|
| A032 (control) | 100 |
| A032I | 103 |
| A032L | 120 |
| A032V | 102 |
| A032W | 110 |
| A032Y | 110 |

Example 11

Figure 7:
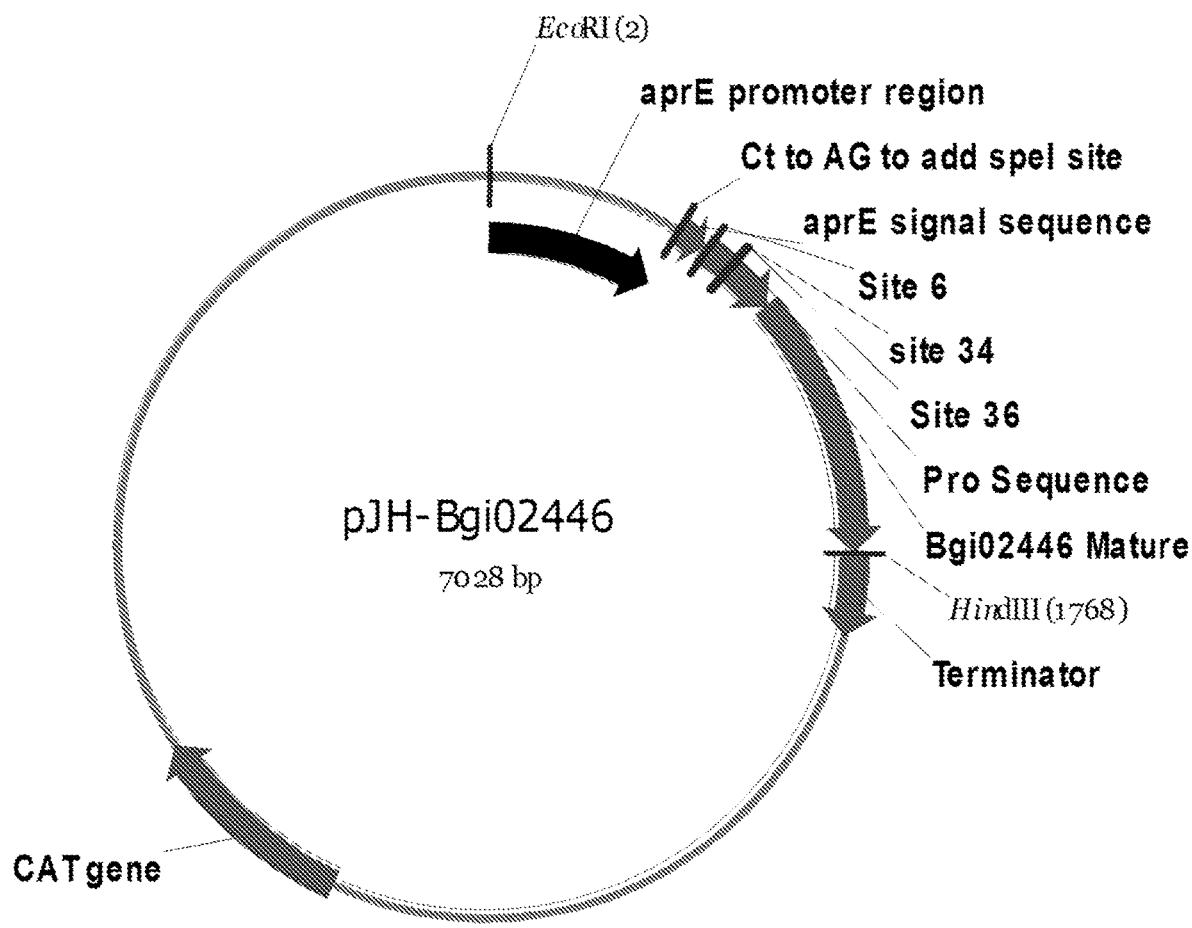
FIG. 7 shows a schematic of a plasmid constructed for expression of mature Bgi02446 using various Bgi02446 propeptide sequences with mutations at amino acid residue positions 6, 34, or 36.

Site-Saturation Mutagenesis at Position 34 of Bgi02446 Pro Sequence for Expression of the Bgi02446 Mature Subtilisin Site-saturation mutagenesis of the Bgi02446 propeptide (SEQ ID NO:7) at amino acid position site 34 was performed using the QuikChange® site-directed mutagenesis kit (QC; Stratagene) according to the directions of the manufacturer. A DNA cassette comprising *B. subtilis* aprE promoter (SEQ ID NO: 1), the *B. subtilis* aprE signal peptide (SEQ ID NO: 2), the *B. gibsonii* Bgi02446 pro sequence (SEQ ID NO: 3) and the *B. gibsonii* Bgi02446 mature gene (SEQ ID NO: 4) was cloned into the EcoRI and HindIII restriction sites of the pJH101 vector (Ferrari et al., J. Bacteriol. 154:1513-1515, 1983) to generate the pJH-Bgi02446 plasmid (FIG. 7).

Complementary overlapping primers were designed for mutating the site 34 with about 18 bases flanking the NNS codon and were ordered from Eurofins Genomics, Huntsville, Ala., USA. The polynucleotide sequences of the forward and reverse primers used to mutate the amino acid at position 34 are given in Table 15.

TABLE 15

NNS Primer Sequences Used to Mutate Site 34 of the Bgi02446 Pro Sequence

| Primer | Sequence | SEQ ID NO: |
|---|---|---|
| Site 34 Forward | GGTGTATTTTCTGTTGAANNSCAAAGTGTAGCTGAGG | 37 |
| Site 34 Reverse | CCTCAGCTACACTTTGSNNTTCAACAGAAAATACACC | 38 |

The pJH-Bgi02446 DNA was used as template in the QuikChange (QC) mutagenesis reaction as follows. Two microliters of pJH-P9 miniprep DNA (50 ng) were added to 39 μL of sterile distilled H$_2$O, 1 μL of PFU Ultra II, 5 ul 10×PFU buffer, 1 μL dNTPs (Roche), 5 μL of forward primer (5 uM), and 5 μl reverse primer (5 uM), for a total of 50 μL. The DNA amplification reaction (PCR) was performed under the following cycling conditions: 95° C. for 1 minute, once, followed by 19-20 cycles of 95° C. for 1 minute, 55° C. for 1 minute and 68° C. for 12 minutes. Five microliters of the PCR reaction were analyzed by electrophoresis using a 1.2% E-gel (Invitrogen).

Subsequently, the mutated amplified DNA was digested twice, using 1 μL DpnI at 37° C. for 2 hours. A negative control was generated under similar conditions, but in the absence of primers. One microliter of each of the DpnI-digested reaction products was used to transform fifty microliters of one-shot *E. coli* TOP10 chemically competent cells (Invitrogen) using the manufacturer's protocol. The transformed cells were grown in Luria's Broth (LB) with shaking at 37° C. for 1 hour, then streaked on Luria Agar (LA) plates containing 50 ppm carbenicillin, and allowed to grow at 37° C. overnight. Following the overnight incubation, individual colonies were picked, used to inoculate 150 μL of LB containing 50 ppm carbenicillin, and grown overnight at 37° C. in 96-well MTPs. DNA sequence analysis was performed to confirm DNA mutations.

Aliquots of the *E. coli* cell cultures harboring the mutated pro sequences were used to inoculate 5 ml of LB+50 ppm carbenicillin. Plasmid DNA was prepared using a Qiagen kit (Qiagen), and a portion of each plasmid DNA was used to transform *B. subtilis* host cells. Ten microliters of the plasmid DNA (pJH-Bgi02446) were used to transform 100 ul of suitable *B. subtilis* competent cells. The pJH-Bgi02446 control plasmid containing the construct comprising the wildtype Bgi02446 pro sequence (SEQ ID NO:3) was also transformed to the same suitable strain of *B. subtilis* cells. The transformed cells were incubated at 37° C. for 1 hour while shaking at 250 rpm. Cells from the transformation mixture were plated onto agar plates containing 1.6% skim milk under chloramphenicol selection. Single colonies were selected to be grown in Luria broth with chloramphenicol. For protease sample generation, cultures were grown on *Bacillus* cell culture media (enriched semi-defined media based on MOPs buffer, with urea as major nitrogen source, glucose as the main carbon source, and supplemented with 1% soytone for robust cell growth). Clarified culture supernatants were assayed for protease activity using the AAPF assay described above in Example 1.

Example 12

Effect of Mutations at Position 34 of the *B. gibsonii* Propeptide on the Expression of the *B. gibsonii* BSP-00801 Variant Subtilisin Aliquots of culture supernatants from expression of the *B. gibsonii* Bgi02246 propeptide SEL and *B. gibsonii* variant BSP-00801 mature subtilisin were assayed as described in Example 1 for AAPF activity. The relative expression of the active (mature) BSP-00801 subtilisin was calculated for each expression plasmid, using the wildtype *B. gibsonii* propeptide as the reference. Table 16 lists the results for variants at position 34 of the *B. gibsonii* Bgi02246 pro peptide (SEQ ID NO:7) that show an increase in expression over the wildtype sequence.

TABLE 16

Effect of Amino Acid Substitution at Position 34 of the *B. gibsonii* Bgi02446 Subtilisin Pro Region on the Production of the *B. gibsonii* BSP-00801 Variant Subtilisin

| Substitutions at Position 34 in Propeptide Region | Percent Relative Protease Expression |
|---|---|
| E34 (control) | 100 |
| 34D | 205 |
| 34C | 118 |
| 34G | 137 |
| 34H | 102 |
| 34S | 113 |
| 34V | 102 |

Example 13

Sequence Comparisons Among *Bacillus* Subtilisin Propeptide Regions

The subtilisin pro peptide sequences of the *Bacillus lentus* and *Bacillus gibsonii* evaluated in this study were compared. FIG. 8 shows a Clustal W alignment of the amino acid sequences of the *B. gibsonii* Bgi02446 propeptide plus the N-terminal four amino acids of the mature region of Bgi02446 (SEQ ID NO: 59, which comprises the 84 residues of SEQ ID NO: 7) and the *B. lentus* P29600 pro peptide plus the N-terminal four amino acids of the mature region of P29600 (SEQ ID NO: 60, which comprises the 87 residues of SEQ ID NO: 8). These 2 propeptide regions share less than 40% sequence identity at the amino acid level of the proregion, with significant differences in the central region as well as the junction where processing occurs (FIG. 8). As presented in FIG. 9, a sequence alignment of the nucleic acid sequences encoding the propeptide regions of *B. gibsonii* (SEQ ID NO:3) and *B. lentus* (SEQ ID NO:5) subtilisins indicates that the percent identity is 53.7%.

A larger collection of subtilisin propeptide sequences from members of the *Bacillus* genus that includes both *B. lentus* and *B. gibsonii* was analyzed, as shown on FIG. 10. Significant diversity is observed across this group of propeptide polypeptides that correspond to subtilisins where the percent identity of the mature regions is greater than 75%. But as can be seen in Table 17 set forth below, the subtilisin propeptide regions share between 35% and 100% sequence identity.

The propeptide sequences from a few representative species that are more or less related to B. lentus were aligned in FIG. 10 (including SEQ ID NOs: 7, 8, 42, 43, 48, 49, 50, 51, 54, and 56). Some of these sequences were first reported in Danisco US, Inc. published PCT application (PCT Publication No. PCT Publication No. WO2015/089447) and U.S. Provisional Application Ser. Nos. 62/069,188 and 62/069,184, both filed Oct. 27, 2014.

Using the sequence alignment of FIG. 10 and other methods, a motif sequence was generated for heterologous or variant propeptide sequences that can be used for expression of mature sequences of B. gibsonii-clade serine proteases is shown in FIG. 11, wherein the motif sequence is set forth in SEQ ID NO: 44. The definition of "X's" in FIG. 11 is as follows: each "X" can be any amino acid, the "X's" at positions 1, 22-51, and 91 can be absent individually or collectively, and there needs to be at least about 23 amino acids present from positions 22 to 51. At certain positions, a slash (/) indicates presence of either of the amino acids listed.

TABLE 17

Percent Sequence Identity Between Each Propeptide Region Aligned in FIG. 10

| | *B. lentus_* P29600 | *B. clausii_* P41362 | *B. lehensis_* AFK08970 | BspA L03240 | BspA K01305 | BspA L03279 | Bgi0 2446 | Bps 02592 | BspQ 01211 | Bps 02003 |
|---|---|---|---|---|---|---|---|---|---|---|
| *B. lentus_* P29600 | | 100 | 75.9 | 77.4 | 39.8 | 50.6 | 37.9 | 52.3 | 52.3 | 46 |
| *B. clausii_* P41362 | 100 | | 75.9 | 77.4 | 39.8 | 50.6 | 37.9 | 52.3 | 52.3 | 46 |
| *B. lehensis_* AFK08970 | 75.9 | 75.9 | | 73.2 | 38.3 | 46.9 | 43.7 | 44.8 | 47.1 | 40.7 |
| BspAL03240 | 77.4 | 77.4 | 73.2 | | 45.1 | 53.7 | 40.2 | 50 | 50 | 37.9 |
| BspAK01305 | 39.8 | 39.8 | 38.3 | 45.1 | | 56.4 | 39.1 | 33.3 | 35.6 | 35.6 |
| BspAL03279 | 50.6 | 50.6 | 46.9 | 53.7 | 56.4 | | 36.8 | 42.5 | 44.8 | 34.5 |
| Bgi02446 | 37.9 | 37.9 | 43.7 | 40.2 | 39.1 | 36.8 | | 32.2 | 36.8 | 35.6 |
| Bps02592 | 52.3 | 52.3 | 44.8 | 50 | 33.3 | 42.5 | 32.2 | | 70.1 | 49.4 |
| BspQ01211 | 52.3 | 52.3 | 47.1 | 50 | 35.6 | 44.8 | 36.8 | 70.1 | | 43.7 |
| Bps02003 | 46 | 46 | 40.7 | 37.9 | 35.6 | 34.5 | 35.6 | 49.4 | 43.7 | |

The invention claimed is:

1. A polynucleotide encoding a modified protease, the polynucleotide comprising:

(a) optionally a first polynucleotide region encoding a signal peptide, (b) a second polynucleotide region encoding a variant propeptide region with at least 60% identity to SEQ ID NO: 7, wherein the variant propeptide region comprises an amino acid substitution at a position corresponding to position 34 of SEQ ID NO: 7, wherein the amino acid substitution at position 34 of SEQ ID NO: 7 is selected from the group consisting of E34D, E34C, E34G, E34H, E34S, and E34V, and (c) a third polynucleotide region encoding the mature region of a second *Bacillus gibsonii*-clade protease;

wherein the first polynucleotide region is operably linked to the second polynucleotide region, and the second polynucleotide region is operably linked to the third polynucleotide region.

2. The polynucleotide of claim 1, wherein the third polynucleotide region encodes the mature region of a protease from *Bacillus gibsonii.*

* * * * *

SEQUENCE LISTING

<160> NUMBER OF SEQ ID NOS: 69

<210> SEQ ID NO 1
<211> LENGTH: 608
<212> TYPE: DNA
<213> ORGANISM: Bacillus subtilis

<400> SEQUENCE: 1
gaattctcca ttttcttctg ctatcaaaat aacagactcg tgattttcca aacgagcttt 60
caaaaaagcc tctgcccctt gcaaatcgga tgcctgtcta taaaattccc gatattggtt 120
aaacagcggc gcaatggcgg ccgcatctga tgtctttgct tggcgaatgt tcatcttatt 180
tcttcctccc tctcaataat tttttcattc tatccctttt ctgtaaagtt tatttttcag 240
aatactttta tcatcatgct ttgaaaaaat atcacgataa tatccattgt tctcacggaa 300
gcacacgcag gtcatttgaa cgaatttttt cgacaggaat ttgccgggac tcaggagcat 360
ttaacctaaa aaagcatgac atttcagcat aatgaacatt tactcatgtc tattttcgtt 420
cttttctgta tgaaaatagt tatttcgagt ctctacggaa atagcgagag atgatatacc 480
taaatagaga taaaatcatc tcaaaaaaat gggtctacta aaatattatt ccatctatta 540
caataaattc acagaatagt cttttaagta agtctactct gaattttttt aaaaggagag 600
ggtaaaga 608

<210> SEQ ID NO 2
<211> LENGTH: 87
<212> TYPE: DNA
<213> ORGANISM: Bacillus subtilis

<400> SEQUENCE: 2

```
gtgagaagca aaaaattgtg gatcagcttg ttgtttgcgt taacgttaat ctttacgatg      60
gcgttcagca acatgtctgc tagcgca                                          87

<210> SEQ ID NO 3
<211> LENGTH: 261
<212> TYPE: DNA
<213> ORGANISM: Bacillus gibsonii

<400> SEQUENCE: 3
gcagaagaaa aagtaaaata cttaataggt ttcgaagaag aagcagaact tgaagccttc      60
actgaggaaa ttgaccaagt tggtgtattt tctgttgaag aacaaagtgt agctgaggat     120
acgttagata ttgatgtaga cattattgat gaatatgatt atattgatgt gttagctgta     180
gaattagatc ctgaggatgt agatgcgtta agtgaagaag caggtatctc atttattgaa     240
gaagacattg aactgtctat t                                              261

<210> SEQ ID NO 4
<211> LENGTH: 807
<212> TYPE: DNA
<213> ORGANISM: Bacillus gibsonii

<400> SEQUENCE: 4
caacaaacag ttccttgggg cattactcgt gttcaagctc cggctgttca taaccgtggg      60
attacaggtt ctggagtaag agtagctatc cttgattcag ggatttcagc ccatagtgat     120
ttgaatatcc gcggtggagc atcatttgta ccgggtgaac caacgacagc tgatttaaat     180
ggacatggta ctcacgtggc cggaacagta gcagctctaa ataattcaat tggtgtcatt     240
ggtgttgcac cgaatgctga attatatgct gttaaagtac ttggagcaaa tggaagcgga     300
agtgtaagtg ggattgctca aggtttagag tgggcggcaa ccaataacat gcatattgcg     360
aacatgagtc tcggtagtga ttttcctagc tctacacttg agcgtgcagt caactatgca     420
acaagccgtg atgtactggt tattgcagcg actggtaata acggttctgg ttcagtaggc     480
tatcctgctc gttatgcaaa cgcaatggct gtaggagcga ctgaccaaaa caacagacgc     540
gcaaactttt ctcagtatgg tacgggaatt gacatcgtag cacctggtgt taacgtacaa     600
agtacgtatc caggtaaccg ttacgtgagt atgaatggta catctatggc tactccacac     660
gtagctggtg ccgcagcgct tgtaaagcaa cgctatccgt cttggaatgc gactcaaatt     720
cgcaatcatc tgaaaaatac agcaacaaat ctaggaaact cttcacaatt tggtagtggc     780
ctagttaacg cagaagcagc aacacgt                                        807

<210> SEQ ID NO 5
<211> LENGTH: 252
<212> TYPE: DNA
<213> ORGANISM: Bacillus lentus

<400> SEQUENCE: 5
gctgaagaag caaaagaaaa atatttaatt ggctttaatg agcaggaagc tgtcagtgag      60
tttgtagaac aagtagaggc aaatgacgag gtcgccattc tctctgagga agaggaagtc     120
gaaattgaat tgcttcatga atttgaaacg attcctgttt tatccgttga gttaagccca     180
gaagatgtgg acgcgcttga gctcgatcca gcgatttctt atattgaaga ggatgcagaa     240
gtaacgacaa tg                                                        252

<210> SEQ ID NO 6
```

<211> LENGTH: 866
<212> TYPE: DNA
<213> ORGANISM: Staphylococcus aureus

<400> SEQUENCE: 6

```
cttagtgaca agggtgataa actcaaatac agcttttaga actggttaca atagcgacgg        60
agagttaggt tattgggata agttagagcc actttataca attttttgatg gtgtatctaa      120
aacattctct ggtatttgga ctcctgtaaa gaatgacttc aaagagtttt atgatttata      180
cctttctgat gtagagaaat ataatggttc ggggaaattg tttcccaaaa cacctatacc      240
tgaaaatgct ttttctcttt ctattattcc atggacttca tttactgggt ttaacttaaa      300
tatcaataat aatagtaatt accttctacc cattattaca gcaggaaaat tcattaataa      360
aggtaattca atatatttac cgctatcttt acaggtacat cattctgttt gtgatggtta      420
tcatgcagga ttgtttatga actctattca ggaattgtca gataggccta atgactggct      480
tttataatat gagataatgc cgactgtact ttttacagtc ggttttctaa tgtcactaag      540
gatccgaatt cacaaacgaa aattggataa agtgggatat ttttaaaata tatatttatg      600
ttacagtaat attgactttt aaaaaaggat tgattctaat gaagaaagca gacaagtaag      660
cctcctaaat tcactttaga taaaaattta ggaggcatat caaatgaact ttaataaaat      720
tgatttagac aattggaaga gaaagagat atttaatcat tatttgaacc aacaaacgac      780
ttttagtata accacagaaa ttgatattag tgttttatac cgaaacataa aacaagaagg      840
atataaattt taccctgcat ttattt                                            866
```

<210> SEQ ID NO 7
<211> LENGTH: 87
<212> TYPE: PRT
<213> ORGANISM: Bacillus gibsonii

<400> SEQUENCE: 7

```
Ala Glu Glu Lys Val Lys Tyr Leu Ile Gly Phe Glu Glu Ala Glu
1               5                   10                  15
Leu Glu Ala Phe Thr Glu Glu Ile Asp Gln Val Gly Val Phe Ser Val
                20                  25                  30
Glu Glu Gln Ser Val Ala Glu Asp Thr Leu Asp Ile Asp Val Asp Ile
            35                  40                  45
Ile Asp Glu Tyr Asp Tyr Ile Asp Val Leu Ala Val Glu Leu Asp Pro
        50                  55                  60
Glu Asp Val Asp Ala Leu Ser Glu Glu Ala Gly Ile Ser Phe Ile Glu
    65                  70                  75                  80
Glu Asp Ile Glu Leu Ser Ile
                85
```

<210> SEQ ID NO 8
<211> LENGTH: 84
<212> TYPE: PRT
<213> ORGANISM: Bacillus lentus

<400> SEQUENCE: 8

```
Ala Glu Glu Ala Lys Glu Lys Tyr Leu Ile Gly Phe Asn Glu Gln Glu
1               5                   10                  15
Ala Val Ser Glu Phe Val Glu Gln Val Glu Ala Asn Asp Glu Val Ala
                20                  25                  30
Ile Leu Ser Glu Glu Glu Glu Val Glu Ile Glu Leu Leu His Glu Phe
            35                  40                  45
```

Glu Thr Ile Pro Val Leu Ser Val Glu Leu Ser Pro Glu Asp Val Asp
    50                  55                  60

Ala Leu Glu Leu Asp Pro Ala Ile Ser Tyr Ile Glu Gly Asp Ala Glu
65                  70                  75                  80

Val Thr Thr Met

<210> SEQ ID NO 9
<211> LENGTH: 807
<212> TYPE: DNA
<213> ORGANISM: Bacillus gibsonii

<400> SEQUENCE: 9

```
caacaaacag tgccatgggg aattactcgt gtgcaagccc cagctgttca taaccgtgga        60
attacaggtt ctggtgtaag agttgctatc ctcgattcag gtatttccac acatgaagac      120
ttaaatgttc gtggtggcgt tagctttgta ccaggggaac caacgactgc tgatttaaat      180
gggcatggca cgcatgtggc tgggacggta gctgctttaa acaattcgat tggcgttgtt      240
ggcgtagcac cgtcagcgga tctatacgct gttaaagtat taggggcgaa tggtagaggt      300
tcggtcagcg ggattgccca aggattggaa tgggcagcag caaataacat gcacattgct      360
aatatgagtt taggaagcga tgcaccaagt tctacacttg agcgtgctgt taattatgcg      420
acttctagag atgttcttgt tattgcggca actgggaata acggttctgg ctcagtaggc      480
tatccggccc gttatgcgaa cgcaatggca gtcgagctga ctgaccaaaa aacagacgc       540
gccaactttt cacagtatgg cacggggatt gacattgtcg caccaggtgt aaacgtgcag      600
agcacatacc caggtaaccg ttatgtgagc atgaacggta catcgatggc tactcctcat      660
gttgcaggtg cagcagccct tgttaaacaa cgctatccat cttggaatgc gactcaaatc      720
cgcaatcatc taaagaatac ggcaacgaat ttaggaaact cttcacaatt tggaagcgga      780
cttgtcaatg cagaagcggc aacacgc                                          807
```

<210> SEQ ID NO 10
<211> LENGTH: 268
<212> TYPE: PRT
<213> ORGANISM: Bacillus gibsonii

<400> SEQUENCE: 10

Gln Thr Val Pro Trp Gly Ile Thr Arg Val Gln Ala Pro Ala Val His
1               5                   10                  15

Asn Arg Gly Ile Thr Gly Ser Gly Val Arg Val Ala Ile Leu Asp Ser
                20                  25                  30

Gly Ile Ser Ala His Ser Asp Leu Asn Ile Arg Gly Gly Ala Ser Phe
            35                  40                  45

Val Pro Gly Glu Pro Thr Thr Ala Asp Leu Asn Gly His Gly Thr His
    50                  55                  60

Val Ala Gly Thr Val Ala Ala Leu Asn Asn Ser Ile Gly Val Ile Gly
65                  70                  75                  80

Val Ala Pro Asn Ala Glu Leu Tyr Ala Val Lys Val Leu Gly Ala Asn
                85                  90                  95

Gly Ser Gly Ser Val Ser Gly Ile Ala Gln Gly Leu Glu Trp Ala Ala
            100                 105                 110

Thr Asn Asn Met His Ile Ala Asn Met Ser Leu Gly Ser Asp Phe Pro
        115                 120                 125

Ser Ser Thr Leu Glu Arg Ala Val Asn Tyr Ala Thr Ser Arg Asp Val
    130                 135                 140

```
Leu Val Ile Ala Ala Thr Gly Asn Asn Gly Ser Gly Ser Val Gly Tyr
145                 150                 155                 160

Pro Ala Arg Tyr Ala Asn Ala Met Ala Val Gly Ala Thr Asp Gln Asn
            165                 170                 175

Asn Arg Arg Ala Asn Phe Ser Gln Tyr Gly Thr Gly Ile Asp Ile Val
        180                 185                 190

Ala Pro Gly Val Asn Val Gln Ser Thr Tyr Pro Gly Asn Arg Tyr Val
    195                 200                 205

Ser Met Asn Gly Thr Ser Met Ala Thr Pro His Val Ala Gly Ala Ala
210                 215                 220

Ala Leu Val Lys Gln Arg Tyr Pro Ser Trp Asn Ala Thr Gln Ile Arg
225                 230                 235                 240

Asn His Leu Lys Asn Thr Ala Thr Asn Leu Gly Asn Ser Ser Gln Phe
            245                 250                 255

Gly Ser Gly Leu Val Asn Ala Glu Ala Ala Thr Arg
        260                 265

<210> SEQ ID NO 11
<211> LENGTH: 269
<212> TYPE: PRT
<213> ORGANISM: Bacillus gibsonii

<400> SEQUENCE: 11

Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Ala His Ser Asp Leu Asn Ile Arg Gly Gly Ala Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asn Asn Ser Ile Gly Val Ile
65                  70                  75                  80

Gly Val Ala Pro Asn Ala Glu Leu Tyr Ala Val Lys Val Leu Gly Ala
                85                  90                  95

Asn Gly Ser Gly Ser Val Ser Gly Ile Ala Gln Gly Leu Glu Trp Ala
            100                 105                 110

Ala Thr Asn Asn Met His Ile Ala Asn Met Ser Leu Gly Ser Asp Phe
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255
```

```
Phe Gly Ser Gly Leu Val Asn Ala Glu Ala Ala Thr Arg
            260                 265
```

<210> SEQ ID NO 12
<211> LENGTH: 269
<212> TYPE: PRT
<213> ORGANISM: Bacillus gibsonii

<400> SEQUENCE: 12

```
Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Thr His Glu Asp Leu Asn Val Arg Gly Gly Val Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asn Asn Ser Ile Gly Val Val
65                  70                  75                  80

Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Ala Asn Asn Met His Ile Ala Asn Met Ser Leu Gly Ser Asp Ala
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265
```

<210> SEQ ID NO 13
<211> LENGTH: 268
<212> TYPE: PRT
<213> ORGANISM: Bacillus gibsonii

<400> SEQUENCE: 13

```
Gln Thr Val Pro Trp Gly Ile Thr Arg Val Gln Ala Pro Ala Val His
1               5                   10                  15

Asn Arg Gly Ile Thr Gly Ser Gly Val Arg Val Ala Ile Leu Asp Ser
            20                  25                  30

Gly Ile Ser Thr His Glu Asp Leu Asn Val Arg Gly Gly Val Ser Phe
        35                  40                  45
```

Val Pro Gly Glu Pro Thr Thr Ala Asp Leu Asn Gly His Gly Thr His
 50                  55                  60

Val Ala Gly Thr Val Ala Ala Leu Asn Asn Ser Ile Gly Val Val Gly
 65                  70                  75                  80

Val Ala Pro Ser Ala Asp Leu Tyr Ala Val Lys Val Leu Gly Ala Asn
                 85                  90                  95

Gly Arg Gly Ser Val Ser Gly Ile Ala Gln Gly Leu Glu Trp Ala Ala
                100                 105                 110

Ala Asn Asn Met His Ile Ala Asn Met Ser Leu Gly Ser Asp Ala Pro
            115                 120                 125

Ser Ser Thr Leu Glu Arg Ala Val Asn Tyr Ala Thr Ser Arg Asp Val
130                 135                 140

Leu Val Ile Ala Ala Thr Gly Asn Asn Gly Ser Gly Ser Val Gly Tyr
145                 150                 155                 160

Pro Ala Arg Tyr Ala Asn Ala Met Ala Val Gly Ala Thr Asp Gln Asn
                165                 170                 175

Asn Arg Arg Ala Asn Phe Ser Gln Tyr Gly Thr Gly Ile Asp Ile Val
            180                 185                 190

Ala Pro Gly Val Asn Val Gln Ser Thr Tyr Pro Gly Asn Arg Tyr Val
        195                 200                 205

Ser Met Asn Gly Thr Ser Met Ala Thr Pro His Val Ala Gly Ala Ala
210                 215                 220

Ala Leu Val Lys Gln Arg Tyr Pro Ser Trp Asn Ala Thr Gln Ile Arg
225                 230                 235                 240

Asn His Leu Lys Asn Thr Ala Thr Asn Leu Gly Asn Ser Ser Gln Phe
                245                 250                 255

Gly Ser Gly Leu Val Asn Ala Glu Ala Ala Thr Arg
            260                 265

<210> SEQ ID NO 14
<211> LENGTH: 1146
<212> TYPE: DNA
<213> ORGANISM: Artificial Sequence
<220> FEATURE:
<223> OTHER INFORMATION: expression cassette

<400> SEQUENCE: 14
gtgagaagca aaaaattgtg gatcagcttg ttgtttgcgt taacgttaat ctttacgatg      60
gcgttcagca acatgtctgc gcaggctgct gaagaagcaa agaaaaaata tttaattggc     120
tttaatgagc aggaagctgt cagtgagttt gtagaacaag tagaggcaaa tgacgaggtc     180
gccattctct ctgaggaaga ggaagtcgaa attgaattgc ttcatgaatt tgaaacgatt     240
cctgttttat ccgttgagtt aagcccagaa gatgtggacg cgcttgaact cgatccagcg     300
atttcttata ttgaagagga tgcagaagta acgacaatgc aacaaacagt gccatgggga     360
attactcgtg tgcaagcccc agctgttcat aaccgtggaa ttacaggttc tggtgtaaga     420
gttgctatcc tcgattcagg tatttccaca catgaagact aaatgttcg tggtggcgtt     480 agctttgtac caggggaacc aacgactgct gatttaaatg gcatggcac gcatgtggct     540 gggacggtag ctgcttttaaa caattcgatt ggcgttgttg gctagcacc gtcagcggat     600 ctatacgctg ttaaagtatt aggggcgaat ggtagaggtt cggtcagcgg gattgcccaa     660
ggattggaat gggcagcagc aaataacatg cacattgcta atatgagttt aggaagcgat     720
gcaccaagtt ctacacttga gcgtgctgtt aattatgcga cttctagaga tgttcttgtt     780

```
attgcggcaa ctgggaataa cggttctggc tcagtaggct atccggcccg ttatgcgaac    840
gcaatggcag tcggagctac tgaccaaaac aacagacgcg ccaactttc acagtatggc    900 acggggattg acattgtcgc accaggtgta acgtgcaga gcacataccc aggtaaccgt    960
tatgtgagca tgaacggtac atcgatggct actcctcatg ttgcaggtgc agcagccctt   1020
gttaaacaac gctatccatc ttggaatgcg actcaaatcc gcaatcatct aaagaatacg   1080
gcaacgaatt taggaaactc ttcacaattt ggaagcggac ttgtcaatgc agaagcggca   1140
acacgc                                                             1146
```

```
<210> SEQ ID NO 15
<211> LENGTH: 42
<212> TYPE: DNA
<213> ORGANISM: Artificial Sequence
<220> FEATURE:
<223> OTHER INFORMATION: primer

<400> SEQUENCE: 15
gaggatgcag aagtaacgac aatgcaacaa acagtgccat gg                       42

<210> SEQ ID NO 16
<211> LENGTH: 52
<212> TYPE: DNA
<213> ORGANISM: Artificial Sequence
<220> FEATURE:
<223> OTHER INFORMATION: primer

<400> SEQUENCE: 16
ccaaggccgg ttttttatgt atctagatta gcgtgttgcc gcttctgcat tg             52

<210> SEQ ID NO 17
<211> LENGTH: 42
<212> TYPE: DNA
<213> ORGANISM: Artificial Sequence
<220> FEATURE:
<223> OTHER INFORMATION: primer

<400> SEQUENCE: 17
gaagaagaca ttgaactgtc tattcaacaa acagtgccat gg                       42

<210> SEQ ID NO 18
<211> LENGTH: 52
<212> TYPE: DNA
<213> ORGANISM: Artificial Sequence
<220> FEATURE:
<223> OTHER INFORMATION: primer

<400> SEQUENCE: 18
caatgcagaa gcggcaacac gctaatctag atacataaaa aaccggcctt gg             52

<210> SEQ ID NO 19
<211> LENGTH: 42
<212> TYPE: DNA
<213> ORGANISM: Artificial Sequence
<220> FEATURE:
<223> OTHER INFORMATION: primer

<400> SEQUENCE: 19
ccatggcact gtttgttgca ttgtcgttac ttctgcatcc tc                       42

<210> SEQ ID NO 20
<211> LENGTH: 42
<212> TYPE: DNA
<213> ORGANISM: Artificial Sequence
```

<220> FEATURE:
<223> OTHER INFORMATION: primer

<400> SEQUENCE: 20
ccatggcact gtttgttgaa tagacagttc aatgtcttct tc        42

<210> SEQ ID NO 21
<211> LENGTH: 43
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: N = A, T, G or C
<220> FEATURE:
<221> NAME/KEY: misc_feature
<222> LOCATION: (21)..(21)
<223> OTHER INFORMATION: S = G or C

<400> SEQUENCE: 21
gctgctgaag aagcaaaann saaatattta attggcttta atg       43

<210> SEQ ID NO 22
<211> LENGTH: 43
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(23)
<223> OTHER INFORMATION: S = G or C
<220> FEATURE:
<221> NAME/KEY: misc_feature
<222> LOCATION: (24)..(25)
<223> OTHER INFORMATION: N = A, T, G or C

<400> SEQUENCE: 22
cattaaagcc aattaaatat ttsnnttttg cttcttcagc agc       43

<210> SEQ ID NO 23
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: N = A, T, G or C

<400> SEQUENCE: 23
caagtagagg caaatgacnn sgtcgccatt ctctctgag            39

<210> SEQ ID NO 24
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(19)
<223> OTHER INFORMATION: S = G or C
<220> FEATURE:
<221> NAME/KEY: misc_feature
<222> LOCATION: (20)..(21)
<223> OTHER INFORMATION: N = A, T, G or C

<400> SEQUENCE: 24
ctcagagaga atggcgacsn ngtcatttgc ctctacttg         39

<210> SEQ ID NO 25
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: N = A, T, G, C
<220> FEATURE:
<221> NAME/KEY: misc_feature
<222> LOCATION: (21)..(21)
<223> OTHER INFORMATION: S = G or C

<400> SEQUENCE: 25
gaggcaaatg acgaggtcnn sattctctct gaggaagag         39

<210> SEQ ID NO 26
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(19)
<223> OTHER INFORMATION: S = G or C
<220> FEATURE:
<221> NAME/KEY: misc_feature
<222> LOCATION: (20)..(21)
<223> OTHER INFORMATION: N = A, T, G or C

<400> SEQUENCE: 26
ctcttcctca gagagaatsn ngacctcgtc atttgcctc         39

<210> SEQ ID NO 27
<211> LENGTH: 47
<212> TYPE: DNA
<213> ORGANISM: Artificial Sequence
<220> FEATURE:
<223> OTHER INFORMATION: primer

<400> SEQUENCE: 27
gatagagctg ggtaaagcct atgaattctc cattttcttc tgctatc         47

<210> SEQ ID NO 28
<211> LENGTH: 45
<212> TYPE: DNA
<213> ORGANISM: Artificial Sequence
<220> FEATURE:
<223> OTHER INFORMATION: primer

<400> SEQUENCE: 28
ataggcttta cccagctcta tcacaaacga aaattggata aagtg         45

<210> SEQ ID NO 29
<211> LENGTH: 42
<212> TYPE: DNA
<213> ORGANISM: Artificial Sequence
<220> FEATURE:
<223> OTHER INFORMATION: primer

<400> SEQUENCE: 29
gaattctcca ttttcttctg ctatcaaaat aacagactcg tg         42

<210> SEQ ID NO 30
<211> LENGTH: 65
<212> TYPE: DNA
<213> ORGANISM: Artificial Sequence
<220> FEATURE:
<223> OTHER INFORMATION: primer

<400> SEQUENCE: 30
acaaacgaaa attggataaa gtgggatatt tttaaaatat atatttatgt tacagtaata    60
ttgac                                                                65

<210> SEQ ID NO 31
<211> LENGTH: 47
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: N = A, T, G or C
<220> FEATURE:
<221> NAME/KEY: misc_feature
<222> LOCATION: (22)..(22)
<223> OTHER INFORMATION: S = G or C

<400> SEQUENCE: 31
ggctgctgaa gaagcaaaan nsaaatattt aattggcttt aatgagc                  47

<210> SEQ ID NO 32
<211> LENGTH: 47
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (26)..(26)
<223> OTHER INFORMATION: S = G or C
<220> FEATURE:
<221> NAME/KEY: misc_feature
<222> LOCATION: (27)..(28)
<223> OTHER INFORMATION: N = A, T, G or C

<400> SEQUENCE: 32
gctcattaaa gccaattaaa tatttsnntt ttgcttcttc agcagcc                  47

<210> SEQ ID NO 33
<211> LENGTH: 42
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (22)..(23)
<223> OTHER INFORMATION: N = A, T, G or C

<400> SEQUENCE: 33
gaacaagtag aggcaaatga cnnsgtcgcc attctctctg ag                       42

<210> SEQ ID NO 34
<211> LENGTH: 42
<212> TYPE: DNA
<213> ORGANISM: Artificial Sequence
<220> FEATURE:
<223> OTHER INFORMATION: primer
<220> FEATURE:

<221> NAME/KEY: misc_feature
<222> LOCATION: (19)..(19)
<223> OTHER INFORMATION: S = G or C
<220> FEATURE:
<221> NAME/KEY: misc_feature
<222> LOCATION: (20)..(21)
<223> OTHER INFORMATION: N = A, T, G or C

<400> SEQUENCE: 34
ctcagagaga atggcgacsn ngtcatttgc ctctacttgt tc                42

<210> SEQ ID NO 35
<211> LENGTH: 40
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: N = A, T, G or C
<220> FEATURE:
<221> NAME/KEY: misc_feature
<222> LOCATION: (21)..(21)
<223> OTHER INFORMATION: S = G or C

<400> SEQUENCE: 35
gaggcaaatg acgaggtcnn sattctctct gaggaagagg                40

<210> SEQ ID NO 36
<211> LENGTH: 40
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(20)
<223> OTHER INFORMATION: S = G or C
<220> FEATURE:
<221> NAME/KEY: misc_feature
<222> LOCATION: (21)..(22)
<223> OTHER INFORMATION: N = A, T, G or C

<400> SEQUENCE: 36
cctcttcctc agagagaats nngacctcgt catttgcctc                40

<210> SEQ ID NO 37
<211> LENGTH: 37
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: N = A, T, G or C
<220> FEATURE:
<221> NAME/KEY: misc_feature
<222> LOCATION: (21)..(21)
<223> OTHER INFORMATION: S = G or C

<400> SEQUENCE: 37
ggtgtatttt ctgttgaann scaaagtgta gctgagg                37

<210> SEQ ID NO 38
<211> LENGTH: 37
<212> TYPE: DNA
<213> ORGANISM: Artificial Sequence
<220> FEATURE:
<223> OTHER INFORMATION: primer

```
<220> FEATURE:
<221> NAME/KEY: misc_feature
<222> LOCATION: (17)..(17)
<223> OTHER INFORMATION: S = G or C
<220> FEATURE:
<221> NAME/KEY: misc_feature
<222> LOCATION: (18)..(19)
<223> OTHER INFORMATION: N = A, T, G or C

<400> SEQUENCE: 38
cctcagctac actttgsnnt tcaacagaaa atacacc                              37

<210> SEQ ID NO 39
<211> LENGTH: 248
<212> TYPE: DNA
<213> ORGANISM: Bacillus lentus

<400> SEQUENCE: 39
tacataaaaa accggccttg gccccgccgg ttttttatta ttttttcttcc tccgcatgtt    60 caatccgctc cataatcgac ggatggctcc ctctgaaaat tttaacgaga aacggcgggt    120
tgacccggct cagtcccgta acggccaagt cctgaaacgt ctcaatcgcc gcttcccggt    180
ttccggtcag ctcaatgccg taacggtcgg cggcgttttc ctgataccgg gagacggcat    240
tcgtaatc                                                             248

<210> SEQ ID NO 40
<211> LENGTH: 29
<212> TYPE: PRT
<213> ORGANISM: Bacillus subtilis

<400> SEQUENCE: 40

Met Arg Ser Lys Lys Leu Trp Ile Ser Leu Leu Phe Ala Leu Thr Leu
1               5                   10                  15

Ile Phe Thr Met Ala Phe Ser Asn Met Ser Ala Ser Ala
            20                  25

<210> SEQ ID NO 41
<211> LENGTH: 4
<212> TYPE: PRT
<213> ORGANISM: Artificial Sequence
<220> FEATURE:
<223> OTHER INFORMATION: x

<400> SEQUENCE: 41

Ala Ala Ala Ala
1

<210> SEQ ID NO 42
<211> LENGTH: 84
<212> TYPE: PRT
<213> ORGANISM: Bacillus clausii

<400> SEQUENCE: 42

Ala Glu Glu Ala Lys Glu Lys Tyr Leu Ile Gly Phe Asn Glu Gln Glu
1               5                   10                  15

Ala Val Ser Glu Phe Val Glu Gln Val Glu Ala Asn Asp Glu Val Ala
            20                  25                  30

Ile Leu Ser Glu Glu Glu Glu Val Glu Ile Glu Leu Leu His Glu Phe
        35                  40                  45

Glu Thr Ile Pro Val Leu Ser Val Glu Leu Ser Pro Glu Asp Val Asp
    50                  55                  60

Ala Leu Glu Leu Asp Pro Ala Ile Ser Tyr Ile Glu Glu Asp Ala Glu
```

-continued

```
                65                  70                  75                  80
Val Thr Thr Met

<210> SEQ ID NO 43
<211> LENGTH: 82
<212> TYPE: PRT
<213> ORGANISM: Bacillus lehensis

<400> SEQUENCE: 43

Ala Glu Glu Ala Lys Glu Lys Tyr Leu Ile Gly Phe Lys Glu Gln Glu
1               5                   10                  15

Val Met Ser Gln Phe Val Asp Gln Ile Asp Gly Asp Glu Tyr Ser Ile
            20                  25                  30

Ser Ser Gln Ala Glu Asp Val Glu Ile Asp Leu Leu His Glu Phe Asp
        35                  40                  45

Phe Ile Pro Val Leu Ser Val Glu Leu Asp Pro Glu Asp Val Asp Ala
    50                  55                  60

Leu Glu Leu Asp Pro Ala Ile Ala Tyr Ile Glu Glu Asp Ala Glu Val
65                  70                  75                  80

Thr Thr

<210> SEQ ID NO 44
<211> LENGTH: 89
<212> TYPE: PRT
<213> ORGANISM: Artificial Sequence
<220> FEATURE:
<223> OTHER INFORMATION: consensus motif
<220> FEATURE:
<221> NAME/KEY: VARIANT
<222> LOCATION: (1)..(1)
<223> OTHER INFORMATION: X is any amino acid
<220> FEATURE:
<221> NAME/KEY: VARIANT
<222> LOCATION: (2)..(2)
<223> OTHER INFORMATION: X is any amino acid
<220> FEATURE:
<221> NAME/KEY: VARIANT
<222> LOCATION: (4)..(4)
<223> OTHER INFORMATION: X is any amino acid
<220> FEATURE:
<221> NAME/KEY: VARIANT
<222> LOCATION: (5)..(5)
<223> OTHER INFORMATION: X is any amino acid
<220> FEATURE:
<221> NAME/KEY: VARIANT
<222> LOCATION: (6)..(6)
<223> OTHER INFORMATION: X is any amino acid
<220> FEATURE:
<221> NAME/KEY: VARIANT
<222> LOCATION: (7)..(7)
<223> OTHER INFORMATION: X is any amino acid
<220> FEATURE:
<221> NAME/KEY: VARIANT
<222> LOCATION: (13)..(20)
<223> OTHER INFORMATION: X is any amino acid
<220> FEATURE:
<221> NAME/KEY: VARIANT
<222> LOCATION: (22)..(51)
<223> OTHER INFORMATION: X is any amino acid
<220> FEATURE:
<221> NAME/KEY: VARIANT
<222> LOCATION: (53)..(53)
<223> OTHER INFORMATION: X is F or Y
<220> FEATURE:
<221> NAME/KEY: VARIANT
<222> LOCATION: (54)..(55)
<223> OTHER INFORMATION: X is any amino acid
<220> FEATURE:
<221> NAME/KEY: VARIANT
<222> LOCATION: (57)..(57)
```

```
<223> OTHER INFORMATION: X is D or P
<220> FEATURE:
<221> NAME/KEY: VARIANT
<222> LOCATION: (59)..(59)
<223> OTHER INFORMATION: X is L or V
<220> FEATURE:
<221> NAME/KEY: VARIANT
<222> LOCATION: (60)..(60)
<223> OTHER INFORMATION: X is A or S
<220> FEATURE:
<221> NAME/KEY: VARIANT
<222> LOCATION: (61)..(61)
<223> OTHER INFORMATION: X is V or A
<220> FEATURE:
<221> NAME/KEY: VARIANT
<222> LOCATION: (62)..(62)
<223> OTHER INFORMATION: X is E or D
<220> FEATURE:
<221> NAME/KEY: VARIANT
<222> LOCATION: (63)..(64)
<223> OTHER INFORMATION: X is any amino acid
<220> FEATURE:
<221> NAME/KEY: VARIANT
<222> LOCATION: (65)..(65)
<223> OTHER INFORMATION: X is P or E
<220> FEATURE:
<221> NAME/KEY: VARIANT
<222> LOCATION: (66)..(66)
<223> OTHER INFORMATION: X is E or A
<220> FEATURE:
<221> NAME/KEY: VARIANT
<222> LOCATION: (67)..(67)
<223> OTHER INFORMATION: X is D or E
<220> FEATURE:
<221> NAME/KEY: VARIANT
<222> LOCATION: (68)..(70)
<223> OTHER INFORMATION: X isany amino acid
<220> FEATURE:
<221> NAME/KEY: VARIANT
<222> LOCATION: (72)..(73)
<223> OTHER INFORMATION: X isany amino acid
<220> FEATURE:
<221> NAME/KEY: VARIANT
<222> LOCATION: (74)..(74)
<223> OTHER INFORMATION: X is D or E
<220> FEATURE:
<221> NAME/KEY: VARIANT
<222> LOCATION: (75)..(76)
<223> OTHER INFORMATION: X is any amino acid
<220> FEATURE:
<221> NAME/KEY: VARIANT
<222> LOCATION: (78)..(78)
<223> OTHER INFORMATION: X is A or S
<220> FEATURE:
<221> NAME/KEY: VARIANT
<222> LOCATION: (79)..(79)
<223> OTHER INFORMATION: X is F or Y
<220> FEATURE:
<221> NAME/KEY: VARIANT
<222> LOCATION: (84)..(84)
<223> OTHER INFORMATION: X is any amino acid
<220> FEATURE:
<221> NAME/KEY: VARIANT
<222> LOCATION: (85)..(85)
<223> OTHER INFORMATION: X is E or D
<220> FEATURE:
<221> NAME/KEY: VARIANT
<222> LOCATION: (86)..(86)
<223> OTHER INFORMATION: X is V or L
<220> FEATURE:
<221> NAME/KEY: VARIANT
<222> LOCATION: (87)..(89)
<223> OTHER INFORMATION: X is any amino acid

<400> SEQUENCE: 44

Xaa Xaa Glu Xaa Lys Xaa Xaa Tyr Leu Ile Gly Phe Xaa Xaa Xaa Xaa
1               5                   10                  15
```

```
Xaa Xaa Xaa Xaa Phe Xaa Xaa Xaa Xaa Xaa Xaa Xaa Xaa Xaa
             20                  25                  30

Xaa Xaa Xaa Xaa Xaa Xaa Xaa Xaa Xaa Xaa Xaa Xaa Xaa Xaa
         35                  40                  45

Xaa Xaa Xaa Glu Xaa Xaa Xaa Ile Xaa Val Xaa Xaa Xaa Xaa Xaa
 50                  55                  60

Xaa Xaa Xaa Xaa Xaa Xaa Leu Xaa Xaa Xaa Xaa Xaa Ile Xaa Xaa Ile
65                  70                  75                  80

Glu Glu Asp Xaa Xaa Xaa Xaa Xaa Xaa
                85

<210> SEQ ID NO 45
<211> LENGTH: 87
<212> TYPE: PRT
<213> ORGANISM: Bacillus gibsonii

<400> SEQUENCE: 45

Ala Glu Glu Lys Val Lys Tyr Leu Ile Gly Phe Glu Glu Ala Glu
 1               5                  10                  15

Leu Glu Ala Phe Thr Glu Glu Val Asp Gln Ile Gly Val Phe Ser Val
                20                  25                  30

Glu Glu Gln Ser Val Val Glu Asp Thr Leu Asp Ile Asp Val Asp Ile
             35                  40                  45

Ile Asp Glu Tyr Glu Tyr Ile Asp Val Leu Ser Val Glu Leu Asp Pro
 50                  55                  60

Glu Asp Val Asp Ala Leu Ser Asp Glu Glu Gly Ile Ser Phe Ile Glu
65                  70                  75                  80

Glu Asp Phe Glu Met Ser Ile
                85

<210> SEQ ID NO 46
<211> LENGTH: 87
<212> TYPE: PRT
<213> ORGANISM: Bacillus gibsonii

<400> SEQUENCE: 46

Ala Glu Glu Lys Val Lys Tyr Leu Ile Gly Phe Glu Glu Ala Glu
 1               5                  10                  15

Leu Glu Ala Phe Ser Glu Glu Ile Asp Gln Val Gly Leu Phe Ser Val
                20                  25                  30

Glu Glu Gln Ser Val Ala Glu Asp Thr Leu Asp Ile Asp Val Asp Ile
             35                  40                  45

Ile Asp Glu Tyr Asp Tyr Ile Asp Val Leu Ser Val Glu Leu Asp Pro
 50                  55                  60

Glu Asp Val Asp Val Leu Ser Glu Glu Glu Gly Ile Ser Phe Ile Glu
65                  70                  75                  80

Glu Asp Phe Glu Met Ser Ile
                85

<210> SEQ ID NO 47
<211> LENGTH: 87
<212> TYPE: PRT
<213> ORGANISM: Bacillus gibsonii

<400> SEQUENCE: 47

Ala Glu Glu Lys Val Lys Tyr Leu Ile Gly Phe Glu Glu Ala Glu
 1               5                  10                  15

Leu Glu Ala Phe Thr Glu Glu Ile Asp Gln Val Gly Val Phe Ser Val
```

```
                20                  25                  30

Glu Glu Gln Ser Val Ala Glu Asp Thr Leu Asp Ile Asp Val Asp Ile
            35                  40                  45

Ile Asp Glu Tyr Asp Tyr Ile Asp Val Leu Ala Val Glu Leu Asp Pro
        50                  55                  60

Glu Asp Val Asp Ala Leu Ser Glu Gly Ala Gly Ile Ser Phe Ile Glu
65                  70                  75                  80

Glu Asp Ile Glu Leu Ser Ile
                85

<210> SEQ ID NO 48
<211> LENGTH: 87
<212> TYPE: PRT
<213> ORGANISM: Bacillus subtilis

<400> SEQUENCE: 48

Asp Glu Glu Lys Lys Thr Tyr Leu Ile Gly Phe His Asn Gln Leu Asp
1               5                   10                  15

Val Asn Glu Phe Ile Glu Glu Asp Val Thr Asn Thr Asn Gly Val Gln
            20                  25                  30

Leu Tyr Thr Ser Glu Asp Lys Ser Ala Gln Val Gln Leu Glu Val Leu
        35                  40                  45

His Glu Phe Glu Gln Ile Pro Val Val Ala Val Glu Leu Ser Pro Ala
    50                  55                  60

Asp Ile Lys Ala Leu Glu Ala Glu Ser Gly Ile Ala Tyr Ile Glu Glu
65                  70                  75                  80

Asp Phe Asp Val Thr Ile Ala
                85

<210> SEQ ID NO 49
<211> LENGTH: 87
<212> TYPE: PRT
<213> ORGANISM: Bacillus subtilis

<400> SEQUENCE: 49

Ala Glu Glu Gln Lys Lys Gln Tyr Leu Ile Gly Phe Glu Asn Gln Val
1               5                   10                  15

Ser Val Thr Glu Phe Val Glu Ser Ser Glu Lys Gly Lys Asp Glu Phe
            20                  25                  30

Ser Ile Phe Ala Glu Ile Asn Asp Glu Thr Ile Glu Met Asp Leu Leu
        35                  40                  45

Tyr Glu Phe Glu Asp Ile Pro Val Val Ser Val Glu Val Ser Pro Glu
    50                  55                  60

Asp Val Lys Asp Leu Glu Gly Asp Pro Ser Ile Ala Phe Ile Glu Glu
65                  70                  75                  80

Asp Ile Glu Val Ser Ile Phe
                85

<210> SEQ ID NO 50
<211> LENGTH: 87
<212> TYPE: PRT
<213> ORGANISM: Bacillus subtilis

<400> SEQUENCE: 50

Ala Glu Glu Ile Lys Lys Gln Tyr Leu Ile Gly Phe Glu Asn Gln Leu
1               5                   10                  15

Gln Val Thr Glu Phe Leu Glu Ala Thr Glu Lys Gly Asn Asp Gln Val
            20                  25                  30
```

Ser Leu Phe Ala Glu Val Asn Asn Asp Thr Val Glu Met Glu Leu Leu
        35                  40                  45

Tyr Glu Phe Glu Glu Ile Pro Val Val Ser Val Glu Leu Ser Pro Glu
 50                  55                  60

Asp Val Gln Ser Leu Lys Lys Asp Pro Ser Ile Ala Tyr Val Glu Glu
65                  70                  75                  80

Asp Val Glu Val Lys Ile Ala
             85

<210> SEQ ID NO 51
<211> LENGTH: 82
<212> TYPE: PRT
<213> ORGANISM: Bacillus subtilis

<400> SEQUENCE: 51

Ala Glu Glu Ala Lys Glu Lys Tyr Leu Ile Gly Phe Thr Glu Gln Glu
1               5                   10                  15

Ala Val Ser Thr Phe Val Glu Gln Ile Glu Glu Glu Val Ser Ile
            20                  25                  30

Ser Glu Val Asp Asp Val Glu Ile Asp Leu Leu Tyr Glu Phe Glu Thr
        35                  40                  45

Ile Pro Val Leu Ser Val Glu Ile Asn Pro Glu Asp Val Ala Ser Leu
 50                  55                  60

Glu Ser Asp Pro Ala Ile Ser Tyr Ile Glu Glu Asp Ala Glu Val Thr
65                  70                  75                  80

Thr Met

<210> SEQ ID NO 52
<211> LENGTH: 82
<212> TYPE: PRT
<213> ORGANISM: Bacillus patagoniensis

<400> SEQUENCE: 52

Ala Glu Glu Ala Lys Glu Lys Tyr Leu Ile Gly Phe Thr Glu Gln Glu
1               5                   10                  15

Ala Val Ser Thr Phe Val Glu Gln Ile Glu Glu Glu Val Ser Ile
            20                  25                  30

Ser Glu Val Asp Asp Val Glu Ile Asp Leu Leu Tyr Glu Phe Glu Thr
        35                  40                  45

Ile Pro Val Leu Ser Val Glu Leu Asn Pro Glu Asp Val Ala Ser Leu
 50                  55                  60

Glu Ser Asp Pro Ala Ile Ser Tyr Ile Glu Glu Asp Ala Glu Val Thr
65                  70                  75                  80

Thr Met

<210> SEQ ID NO 53
<211> LENGTH: 78
<212> TYPE: PRT
<213> ORGANISM: Bacillus subtilis

<400> SEQUENCE: 53

Ala Glu Glu Lys Lys Ser Tyr Leu Ile Gly Phe Asp Glu Pro Gln Glu
1               5                   10                  15

Val Glu Gln Phe Thr Thr Asn Leu Ala Glu Glu Ile Arg Thr Gln Ala
            20                  25                  30

Asp Asp Ala Ile Asp Val Thr Tyr Glu Phe Lys Glu Ile Pro Val Leu
        35                  40                  45

```
Ala Val Glu Met Thr Glu Glu Met Ala Glu Leu Lys Asn Glu Glu
        50                  55                  60

Ser Ile Ser Tyr Ile Glu Asp Gln Glu Val Thr Thr Met
 65                  70                  75
```

<210> SEQ ID NO 54
<211> LENGTH: 78
<212> TYPE: PRT
<213> ORGANISM: Bacillus subtilis

<400> SEQUENCE: 54

```
Ala Glu Glu Lys Lys Ser Tyr Leu Ile Gly Phe Asp Glu Pro Gln Glu
 1               5                  10                  15

Val Glu Gln Phe Thr Thr Asn Leu Glu Glu Ile Arg Thr Gln Ala
                20                  25                  30

Asp Asp Ala Ile Asp Val Thr Tyr Glu Phe Lys Asp Ile Pro Val Leu
            35                  40                  45

Ala Val Asp Met Thr Glu Glu Met Thr Glu Leu Lys Asn Glu Glu
        50                  55                  60

Ser Ile Ser Tyr Ile Glu Asp Gln Glu Val Thr Thr Met
 65                  70                  75
```

<210> SEQ ID NO 55
<211> LENGTH: 78
<212> TYPE: PRT
<213> ORGANISM: Bacillus patagoniensis

<400> SEQUENCE: 55

```
Glu Glu Thr Lys Lys Thr Tyr Leu Ile Gly Phe Asp Ala Gln Glu Glu
 1               5                  10                  15

Val Glu Thr Phe Thr Asn Ile Val Asp Ser Glu Ile Gly Ala Leu Ser
                20                  25                  30

Glu Glu Asp Ile Asp Ile Thr Tyr Glu Phe Lys Asp Ile Pro Val Val
            35                  40                  45

Ser Ala Glu Met Ser Asp Glu Glu Tyr Ala Ala Leu Leu Glu Asp Pro
        50                  55                  60

Ser Ile Ser Tyr Ile Glu Glu Asp Ile Glu Val Thr Thr Met
 65                  70                  75
```

<210> SEQ ID NO 56
<211> LENGTH: 78
<212> TYPE: PRT
<213> ORGANISM: Bacillus subtilis

<400> SEQUENCE: 56

```
Glu Glu Thr Lys Lys Thr Tyr Leu Ile Gly Phe Asp Ala Gln Glu Glu
 1               5                  10                  15

Val Glu Thr Phe Thr Asn Met Val Asp Ser Glu Ile Gly Ala Leu Ser
                20                  25                  30

Glu Glu Glu Ile Asp Ile Thr Tyr Glu Phe Lys Glu Ile Pro Val Val
            35                  40                  45

Ser Ala Glu Met Ser Glu Glu Glu Tyr Ala Ala Leu Leu Glu Asp Pro
        50                  55                  60

Ser Ile Ser Tyr Ile Glu Glu Asp Ile Glu Val Thr Thr Met
 65                  70                  75
```

<210> SEQ ID NO 57
<211> LENGTH: 383

<212> TYPE: PRT
<213> ORGANISM: Unknown
<220> FEATURE:
<223> OTHER INFORMATION: B gibsonii clade DSM 9731

<400> SEQUENCE: 57

```
Met Lys Arg Arg Val Gly Lys Leu Val Val Gly Leu Val Cys Val Thr
1               5                   10                  15

Ala Leu Val Thr Val Thr Asp Ser Ala Ser Ala Glu Glu Lys Val
            20                  25                  30

Lys Tyr Leu Ile Gly Phe Glu Glu Ala Glu Leu Glu Ala Phe Thr
        35                  40                  45

Glu Glu Ile Asp Gln Val Gly Val Phe Ser Val Glu Glu Gln Ser Val
50                  55                  60

Ala Glu Asp Thr Leu Asp Ile Asp Val Asp Ile Ile Asp Glu Tyr Asp
65                  70                  75                  80

Tyr Ile Asp Val Leu Ala Val Glu Leu Asp Pro Glu Asp Val Asp Ala
                85                  90                  95

Leu Ser Glu Glu Ala Gly Ile Ser Phe Ile Glu Glu Asp Ile Glu Leu
            100                 105                 110

Ser Ile Gln Gln Thr Val Pro Trp Gly Ile Thr Arg Val Gln Ala Pro
        115                 120                 125

Ala Val His Asn Arg Gly Val Thr Gly Ser Gly Val Arg Val Ala Ile
130                 135                 140

Leu Asp Ser Gly Ile Ser Thr His Ser Asp Leu Thr Ile Arg Gly Gly
145                 150                 155                 160

Ala Ser Phe Val Pro Gly Glu Pro Thr Thr Ala Asp Leu Asn Gly His
                165                 170                 175

Gly Thr His Val Ala Gly Thr Val Ala Ala Leu Asn Asn Ser Ile Gly
            180                 185                 190

Val Ile Gly Val Ala Pro Ser Ala Asp Leu Tyr Ala Val Lys Val Leu
        195                 200                 205

Gly Ala Asn Gly Arg Gly Ser Val Ser Gly Ile Ala Gln Gly Leu Glu
210                 215                 220

Trp Ala Ala Ala Asn Asn Met His Ile Ala Asn Met Ser Leu Gly Ser
225                 230                 235                 240

Asp Ala Pro Ser Thr Thr Leu Glu Arg Ala Val Asn Tyr Ala Thr Ser
                245                 250                 255

Gln Gly Val Leu Val Ile Ala Ala Thr Gly Asn Asn Gly Ser Gly Ser
            260                 265                 270

Val Gly Tyr Pro Ala Arg Tyr Ala Asn Ala Met Ala Val Gly Ala Thr
        275                 280                 285

Asp Gln Asn Asn Arg Arg Ala Asn Phe Ser Gln Tyr Gly Ser Gly Ile
290                 295                 300

Asp Ile Val Ala Pro Gly Val Asn Val Gln Ser Thr Tyr Pro Gly Asn
305                 310                 315                 320

Arg Tyr Val Ser Met Asn Gly Thr Ser Met Ala Thr Pro His Val Ala
                325                 330                 335

Gly Ala Ala Ala Leu Val Lys Gln Arg Tyr Pro Ser Trp Asn Ala Thr
            340                 345                 350

Gln Ile Arg Asn His Leu Lys Asn Thr Ala Thr Asn Leu Gly Asn Ser
        355                 360                 365

Ser Gln Phe Gly Ser Gly Leu Val Asn Ala Glu Ala Ala Thr Arg
370                 375                 380
```

```
<210> SEQ ID NO 58
<211> LENGTH: 382
<212> TYPE: PRT
<213> ORGANISM: Artificial Sequence
<220> FEATURE:
<223> OTHER INFORMATION: variant

<400> SEQUENCE: 58

Val Arg Ser Lys Lys Leu Trp Ile Ser Leu Leu Phe Ala Leu Thr Leu
1               5                   10                  15

Ile Phe Thr Met Ala Phe Ser Asn Met Ser Ala Gln Ala Ala Glu Glu
            20                  25                  30

Ala Lys Glu Lys Tyr Leu Ile Gly Phe Asn Glu Gln Glu Ala Val Ser
        35                  40                  45

Glu Phe Val Glu Gln Val Glu Ala Asn Asp Glu Val Ala Ile Leu Ser
    50                  55                  60

Glu Glu Glu Glu Val Glu Ile Glu Leu Leu His Glu Phe Glu Thr Ile
65                  70                  75                  80

Pro Val Leu Ser Val Glu Leu Ser Pro Glu Asp Val Asp Ala Leu Glu
                85                  90                  95

Leu Asp Pro Ala Ile Ser Tyr Ile Glu Glu Asp Ala Glu Val Thr Thr
            100                 105                 110

Met Gln Gln Thr Val Pro Trp Gly Ile Thr Arg Val Gln Ala Pro Ala
        115                 120                 125

Val His Asn Arg Gly Ile Thr Gly Ser Gly Val Arg Val Ala Ile Leu
    130                 135                 140

Asp Ser Gly Ile Ser Thr His Glu Asp Leu Asn Val Arg Gly Gly Val
145                 150                 155                 160

Ser Phe Val Pro Gly Glu Pro Thr Thr Ala Asp Leu Asn Gly His Gly
                165                 170                 175

Thr His Val Ala Gly Thr Val Ala Ala Leu Asn Asn Ser Ile Gly Val
            180                 185                 190

Val Gly Val Ala Pro Ser Ala Asp Leu Tyr Ala Val Lys Val Leu Gly
        195                 200                 205

Ala Asn Gly Arg Gly Ser Val Ser Gly Ile Ala Gln Gly Leu Glu Trp
    210                 215                 220

Ala Ala Ala Asn Asn Met His Ile Ala Asn Met Ser Leu Gly Ser Asp
225                 230                 235                 240

Ala Pro Ser Ser Thr Leu Glu Arg Ala Val Asn Tyr Ala Thr Ser Arg
                245                 250                 255

Asp Val Leu Val Ile Ala Ala Thr Gly Asn Asn Gly Ser Gly Ser Val
            260                 265                 270

Gly Tyr Pro Ala Arg Tyr Ala Asn Ala Met Ala Val Gly Ala Thr Asp
        275                 280                 285

Gln Asn Asn Arg Arg Ala Asn Phe Ser Gln Tyr Gly Thr Gly Ile Asp
    290                 295                 300

Ile Val Ala Pro Gly Val Asn Val Gln Ser Thr Tyr Pro Gly Asn Arg
305                 310                 315                 320

Tyr Val Ser Met Asn Gly Thr Ser Met Ala Thr Pro His Val Ala Gly
                325                 330                 335

Ala Ala Ala Leu Val Lys Gln Arg Tyr Pro Ser Trp Asn Ala Thr Gln
            340                 345                 350

Ile Arg Asn His Leu Lys Asn Thr Ala Thr Asn Leu Gly Asn Ser Ser
        355                 360                 365
```

```
Gln Phe Gly Ser Gly Leu Val Asn Ala Glu Ala Ala Thr Arg
    370                 375                 380

<210> SEQ ID NO 59
<211> LENGTH: 91
<212> TYPE: PRT
<213> ORGANISM: Bacillus gibsonii

<400> SEQUENCE: 59

Ala Glu Glu Lys Val Lys Tyr Leu Ile Gly Phe Glu Glu Ala Glu
1               5                   10                  15

Leu Glu Ala Phe Thr Glu Glu Ile Asp Gln Val Gly Val Phe Ser Val
                20                  25                  30

Glu Glu Gln Ser Val Ala Glu Asp Thr Leu Asp Ile Asp Val Asp Ile
            35                  40                  45

Ile Asp Glu Tyr Asp Tyr Ile Asp Val Leu Ala Val Glu Leu Asp Pro
        50                  55                  60

Glu Asp Val Asp Ala Leu Ser Glu Gly Ala Gly Ile Ser Phe Ile Glu
65                  70                  75                  80

Glu Asp Ile Glu Leu Ser Ile Gln Gln Thr Val
                85                  90

<210> SEQ ID NO 60
<211> LENGTH: 88
<212> TYPE: PRT
<213> ORGANISM: Bacillus lentus

<400> SEQUENCE: 60

Ala Glu Glu Ala Lys Glu Lys Tyr Leu Ile Gly Phe Asn Glu Gln Glu
1               5                   10                  15

Ala Val Ser Glu Phe Val Glu Gln Val Glu Ala Asn Asp Glu Val Ala
                20                  25                  30

Ile Leu Ser Glu Glu Glu Val Glu Ile Glu Leu Leu His Glu Phe
            35                  40                  45

Glu Thr Ile Pro Val Leu Ser Val Glu Leu Ser Pro Glu Asp Val Asp
        50                  55                  60

Ala Leu Glu Leu Asp Pro Ala Ile Ser Tyr Ile Glu Gly Asp Ala Glu
65                  70                  75                  80

Val Thr Thr Met Ala Gln Ser Val
                85

<210> SEQ ID NO 61
<211> LENGTH: 383
<212> TYPE: PRT
<213> ORGANISM: Bacillus gibsonii

<400> SEQUENCE: 61

Met Lys Arg Lys Val Gly Lys Leu Met Val Gly Leu Val Cys Val Thr
1               5                   10                  15

Ala Leu Val Thr Val Thr Asp Ser Ala Ser Ala Glu Glu Lys Val
                20                  25                  30

Lys Tyr Leu Ile Gly Phe Glu Glu Ala Glu Leu Glu Ala Phe Thr
            35                  40                  45

Glu Glu Ile Asp Gln Val Gly Val Phe Ser Val Glu Glu Gln Ser Val
        50                  55                  60

Ala Glu Asp Thr Leu Asp Ile Asp Val Asp Ile Ile Asp Glu Tyr Asp
65                  70                  75                  80

Tyr Ile Asp Val Leu Ala Val Glu Leu Asp Pro Glu Asp Val Asp Ala
```

```
              85                  90                  95
Leu Ser Glu Glu Ala Gly Ile Ser Phe Ile Glu Glu Asp Ile Glu Leu
            100                 105                 110

Ser Ile Gln Gln Thr Val Pro Trp Gly Ile Thr Arg Val Gln Ala Pro
            115                 120                 125

Ala Val His Asn Arg Gly Ile Thr Gly Ser Gly Val Arg Val Ala Ile
            130                 135                 140

Leu Asp Ser Gly Ile Ser Ala His Ser Asp Leu Asn Ile Arg Gly Gly
145                 150                 155                 160

Ala Ser Phe Val Pro Gly Glu Pro Thr Thr Ala Asp Leu Asn Gly His
                165                 170                 175

Gly Thr His Val Ala Gly Thr Val Ala Ala Leu Asn Asn Ser Ile Gly
                180                 185                 190

Val Ile Gly Val Ala Pro Asn Ala Glu Leu Tyr Ala Val Lys Val Leu
                195                 200                 205

Gly Ala Asn Gly Ser Gly Ser Val Ser Gly Ile Ala Gln Gly Leu Glu
            210                 215                 220

Trp Ala Ala Thr Asn Asn Met His Ile Ala Asn Met Ser Leu Gly Ser
225                 230                 235                 240

Asp Phe Pro Ser Ser Thr Leu Glu Arg Ala Val Asn Tyr Ala Thr Ser
                245                 250                 255

Arg Asp Val Leu Val Ile Ala Ala Thr Gly Asn Asn Gly Ser Gly Ser
                260                 265                 270

Val Gly Tyr Pro Ala Arg Tyr Ala Asn Ala Met Ala Val Gly Ala Thr
                275                 280                 285

Asp Gln Asn Asn Arg Arg Ala Asn Phe Ser Gln Tyr Gly Thr Gly Ile
            290                 295                 300

Asp Ile Val Ala Pro Gly Val Asn Val Gln Ser Thr Tyr Pro Gly Asn
305                 310                 315                 320

Arg Tyr Val Ser Met Asn Gly Thr Ser Met Ala Thr Pro His Val Ala
                325                 330                 335

Gly Ala Ala Ala Leu Val Lys Gln Arg Tyr Pro Ser Trp Asn Ala Thr
                340                 345                 350

Gln Ile Arg Asn His Leu Lys Asn Thr Ala Thr Asn Leu Gly Asn Ser
            355                 360                 365

Ser Gln Phe Gly Ser Gly Leu Val Asn Ala Glu Ala Ala Thr Arg
            370                 375                 380

<210> SEQ ID NO 62
<211> LENGTH: 382
<212> TYPE: PRT
<213> ORGANISM: Unknown
<220> FEATURE:
<223> OTHER INFORMATION: DSM 9728

<400> SEQUENCE: 62

Met Lys Arg Arg Val Gly Lys Leu Val Val Gly Leu Val Cys Val Thr
1               5                   10                  15

Ala Leu Val Thr Val Thr Asp Ser Ala Ser Ala Glu Glu Lys Val
            20                  25                  30

Lys Tyr Leu Ile Gly Phe Glu Glu Ala Glu Leu Glu Ala Phe Thr
        35                  40                  45

Glu Glu Ile Asp Gln Val Gly Val Phe Ser Val Glu Glu Gln Ser Val
    50                  55                  60

Ala Glu Asp Thr Leu Asp Ile Asp Val Asp Ile Ile Asp Glu Tyr Asp
```

```
                65                  70                  75                  80
Tyr Ile Asp Val Leu Ala Val Glu Leu Asp Pro Glu Asp Val Asp Ala
                    85                  90                  95

Leu Ser Glu Glu Ala Gly Ile Ser Phe Ile Glu Asp Ile Glu Leu
            100                 105                 110

Ser Ile Gln Gln Thr Val Pro Trp Gly Ile Thr Arg Val Gln Ala Pro
            115                 120                 125

Ala Val His Asn Arg Gly Val Thr Gly Ser Gly Val Arg Val Ala Ile
            130                 135                 140

Leu Asp Ser Gly Ile Ser Thr His Ser Asp Leu Thr Ile Arg Gly Gly
145                 150                 155                 160

Ala Ser Phe Val Pro Gly Glu Pro Thr Thr Ala Asp Leu Asn Gly His
                    165                 170                 175

Gly Thr His Val Ala Gly Thr Val Ala Ala Leu Asn Asn Ser Ile Gly
                    180                 185                 190

Val Ile Gly Val Ala Pro Ser Ala Asp Leu Tyr Ala Val Lys Val Leu
                    195                 200                 205

Gly Ala Asn Gly Arg Gly Ser Val Ser Gly Ile Ala Gln Gly Leu Glu
            210                 215                 220

Trp Ala Ala Ala Asn Asn Met His Ile Ala Asn Met Ser Leu Gly Ser
225                 230                 235                 240

Asp Ala Pro Ser Thr Thr Leu Glu Arg Ala Val Asn Tyr Ala Thr Ser
                    245                 250                 255

Gln Gly Val Leu Val Ile Ala Ala Thr Gly Asn Asn Gly Ser Gly Ser
                    260                 265                 270

Val Gly Tyr Pro Ala Arg Tyr Ala Asn Ala Met Ala Val Gly Ala Thr
                    275                 280                 285

Asp Gln Asn Asn Arg Arg Ala Asn Phe Ser Gln Tyr Gly Thr Gly Ile
            290                 295                 300

Asp Ile Val Ala Pro Gly Val Asn Val Gln Ser Thr Tyr Pro Gly Asn
305                 310                 315                 320

Arg Tyr Ala Ser Leu Asn Gly Thr Ser Met Ala Thr Pro His Val Ala
                    325                 330                 335

Gly Ala Ala Ala Leu Val Lys Gln Arg Tyr Pro Ser Trp Asn Ala Thr
                    340                 345                 350

Gln Ile Arg Asn His Leu Lys Asn Thr Ala Thr Asn Leu Gly Asn Ser
            355                 360                 365

Ser Gln Phe Gly Ser Gly Leu Val Asn Ala Glu Ala Ala Thr
370                 375                 380

<210> SEQ ID NO 63
<211> LENGTH: 383
<212> TYPE: PRT
<213> ORGANISM: Unknown
<220> FEATURE:
<223> OTHER INFORMATION: DSM 9729

<400> SEQUENCE: 63

Met Lys Arg Arg Val Gly Lys Leu Val Val Gly Leu Val Cys Val Thr
1               5                   10                  15

Ala Leu Val Thr Val Thr Asp Ser Ala Ser Ala Ala Glu Glu Lys Val
                    20                  25                  30

Lys Tyr Leu Ile Gly Phe Glu Glu Ala Glu Leu Glu Ala Phe Thr
                35                  40                  45

Glu Glu Ile Asp Gln Val Gly Val Phe Ser Val Glu Glu Gln Ser Val
```

```
                50                  55                  60
Ala Glu Asp Thr Leu Asp Ile Asp Val Asp Ile Ile Asp Glu Tyr Asp
 65                  70                  75                  80

Tyr Ile Asp Val Leu Ala Val Glu Leu Asp Pro Glu Asp Val Asp Ala
                 85                  90                  95

Leu Ser Glu Glu Ala Gly Ile Ser Phe Ile Glu Asp Ile Glu Leu
                100                 105                 110

Ser Ile Gln Gln Thr Val Pro Trp Gly Ile Thr Arg Val Gln Ala Pro
                115                 120                 125

Ala Val His Asn Arg Gly Ile Thr Gly Ser Gly Val Arg Val Ala Ile
                130                 135                 140

Leu Asp Ser Gly Ile Ser Ala His Ser Asp Leu Asn Ile Arg Gly Gly
145                 150                 155                 160

Ala Ser Phe Val Pro Gly Glu Pro Thr Thr Ala Asp Leu Asn Gly His
                165                 170                 175

Gly Thr His Val Ala Gly Thr Val Ala Ala Leu Asn Asn Ser Ile Gly
                180                 185                 190

Val Ile Gly Val Ala Pro Asn Ala Asp Leu Tyr Ala Val Lys Val Leu
                195                 200                 205

Gly Ala Asn Gly Ser Gly Ser Val Ser Gly Ile Ala Gln Gly Leu Glu
                210                 215                 220

Trp Ala Ala Thr Asn Asn Met His Ile Ala Asn Met Ser Leu Gly Ser
225                 230                 235                 240

Asp Phe Pro Ser Ser Thr Leu Glu Arg Ala Val Asn Tyr Ala Thr Ser
                245                 250                 255

Arg Asp Val Leu Val Ile Ala Ala Thr Gly Asn Asn Gly Ser Gly Ser
                260                 265                 270

Val Gly Tyr Pro Ala Arg Tyr Ala Asn Ala Met Ala Val Gly Ala Thr
                275                 280                 285

Asp Gln Asn Asn Arg Arg Ala Asn Phe Ser Gln Tyr Gly Thr Gly Ile
                290                 295                 300

Asp Ile Val Ala Pro Gly Val Asn Val Gln Ser Thr Tyr Pro Gly Asn
305                 310                 315                 320

Arg Tyr Val Ser Met Asn Gly Thr Ser Met Ala Thr Pro His Val Ala
                325                 330                 335

Gly Ala Ala Ala Leu Val Lys Gln Arg Tyr Pro Ser Trp Asn Ala Thr
                340                 345                 350

Gln Ile Arg Asn His Leu Lys Asn Thr Ala Thr Asn Leu Gly Asn Ser
                355                 360                 365

Ser Gln Phe Gly Ser Gly Leu Val Asn Ala Glu Ala Thr Arg
                370                 375                 380

<210> SEQ ID NO 64
<211> LENGTH: 383
<212> TYPE: PRT
<213> ORGANISM: Unknown
<220> FEATURE:
<223> OTHER INFORMATION: DSM 9730

<400> SEQUENCE: 64

Met Lys Arg Arg Val Gly Lys Leu Val Val Gly Leu Val Cys Val Thr
  1               5                  10                  15

Ala Leu Val Thr Val Thr Asp Ser Ala Ser Ala Glu Glu Lys Val
                 20                  25                  30

Lys Tyr Leu Ile Gly Phe Glu Glu Glu Ala Glu Leu Glu Ala Phe Thr
```

```
            35                  40                  45
Glu Glu Ile Asp Gln Val Gly Val Phe Ser Val Glu Glu Gln Ser Val
 50                  55                  60

Ala Glu Asp Thr Leu Asp Ile Asp Val Asp Ile Ile Asp Glu Tyr Asp
 65                  70                  75                  80

Tyr Ile Asp Val Leu Ala Val Glu Leu Asp Pro Glu Asp Val Asp Ala
                 85                  90                  95

Leu Ser Glu Glu Ala Gly Ile Ser Phe Ile Glu Glu Asp Ile Glu Leu
                100                 105                 110

Ser Ile Gln Gln Thr Val Pro Trp Gly Ile Thr Arg Val Gln Ala Pro
                115                 120                 125

Ala Val His Asn Arg Gly Val Thr Gly Ser Gly Val Arg Val Ala Ile
                130                 135                 140

Leu Asp Ser Gly Ile Ser Thr His Ser Asp Leu Thr Ile Arg Gly Gly
145                 150                 155                 160

Ala Ser Phe Val Pro Gly Glu Pro Thr Thr Ala Asp Leu Asn Gly His
                165                 170                 175

Gly Thr His Val Ala Gly Thr Val Ala Ala Leu Asn Asn Ser Ile Gly
                180                 185                 190

Val Ile Gly Val Ala Pro Ser Ala Asp Leu Tyr Ala Val Lys Val Leu
                195                 200                 205

Gly Ala Asn Gly Arg Gly Ser Val Ser Gly Ile Ala Gln Gly Leu Glu
                210                 215                 220

Trp Ala Ala Ala Asn Asn Met His Ile Ala Asn Met Ser Leu Gly Ser
225                 230                 235                 240

Asp Ala Pro Ser Thr Thr Leu Glu Arg Ala Val Asn Tyr Ala Thr Ser
                245                 250                 255

Gln Gly Val Leu Val Ile Ala Ala Thr Gly Asn Asn Gly Ser Gly Ser
                260                 265                 270

Val Gly Tyr Pro Ala Arg Tyr Ala Asn Ala Met Ala Val Gly Ala Thr
                275                 280                 285

Asp Gln Asn Asn Arg Arg Ala Asn Phe Ser Gln Tyr Gly Thr Gly Ile
                290                 295                 300

Asp Ile Val Ala Pro Gly Val Asn Val Gln Ser Thr Tyr Pro Gly Asn
305                 310                 315                 320

Arg Tyr Val Ser Met Asn Gly Thr Ser Met Ala Thr Pro His Val Ala
                325                 330                 335

Gly Ala Ala Ala Leu Val Lys Gln Arg Tyr Pro Ser Trp Asn Ala Thr
                340                 345                 350

Gln Ile Arg Asn His Leu Lys Asn Thr Ala Thr Asn Leu Gly Asn Ser
                355                 360                 365

Ser Gln Phe Gly Ser Gly Leu Val Asn Ala Glu Ala Ala Thr Arg
                370                 375                 380

<210> SEQ ID NO 65
<211> LENGTH: 269
<212> TYPE: PRT
<213> ORGANISM: Unknown
<220> FEATURE:
<223> OTHER INFORMATION: B gibsonii clade

<400> SEQUENCE: 65

Gln Gln Thr Val Pro Trp Gly Ile Thr Arg Val Gln Ala Pro Ala Val
 1                   5                  10                  15

His Asn Arg Gly Val Thr Gly Ser Gly Val Arg Val Ala Ile Leu Asp
```

```
                    20                  25                  30

Ser Gly Ile Ser Thr His Ser Asp Leu Thr Ile Arg Gly Gly Ala Ser
                     35                  40                  45

Phe Val Pro Gly Glu Pro Thr Thr Ala Asp Leu Asn Gly His Gly Thr
                     50                  55                  60

His Val Ala Gly Thr Val Ala Ala Leu Asn Asn Ser Ile Gly Val Ile
         65                  70                  75                  80

Gly Val Ala Pro Ser Ala Asp Leu Tyr Ala Val Lys Val Leu Gly Ala
                             85                  90                  95

Asn Gly Arg Gly Ser Val Ser Gly Ile Ala Gln Gly Leu Glu Trp Ala
                        100                 105                 110

Ala Ala Asn Asn Met His Ile Ala Asn Met Ser Leu Gly Ser Asp Ala
                    115                 120                 125

Pro Ser Ile Thr Leu Glu Arg Ala Val Asn Tyr Ala Thr Ser Gln Gly
                130                 135                 140

Val Leu Val Ile Ala Ala Thr Gly Asn Asn Gly Ser Gly Ser Val Gly
        145                 150                 155                 160

Tyr Pro Ala Arg Tyr Ala Asn Ala Met Ala Val Gly Ala Thr Asp Gln
                        165                 170                 175

Asn Asn Arg Arg Ala Asn Phe Ser Gln Tyr Gly Thr Gly Ile Asp Ile
                    180                 185                 190

Val Ala Pro Gly Val Asn Val Gln Ser Thr Tyr Pro Gly Asn Arg Tyr
                195                 200                 205

Ala Ser Leu Asn Gly Thr Ser Met Ala Thr Pro His Val Ala Gly Ala
                210                 215                 220

Ala Ala Leu Val Lys Gln Arg Tyr Pro Ser Trp Asn Ala Thr Gln Ile
        225                 230                 235                 240

Arg Asn His Leu Lys Asn Thr Ala Thr Asn Leu Gly Asn Ser Ser Gln
                        245                 250                 255

Phe Gly Ser Gly Leu Val Asn Ala Glu Ala Ala Thr Arg
                        260                 265

<210> SEQ ID NO 66
<211> LENGTH: 269
<212> TYPE: PRT
<213> ORGANISM: Unknown
<220> FEATURE:
<223> OTHER INFORMATION: B gibsonii clade

<400> SEQUENCE: 66

Gln Gln Thr Val Pro Trp Gly Ile Thr Arg Val Gln Ala Pro Thr Val
        1               5                   10                  15

His Asn Arg Gly Ile Thr Gly Ser Gly Val Lys Val Ala Ile Leu Asp
                        20                  25                  30

Thr Gly Ile Ala Gln His Ser Asp Leu Thr Ile Arg Gly Gly Ala Ser
                    35                  40                  45

Phe Val Pro Gly Glu Ser Thr Thr Ala Asp Leu Asn Gly His Gly Thr
                50                  55                  60

His Val Ala Gly Thr Val Ala Ala Leu Asn Asn Ser Ile Gly Val Ile
        65                  70                  75                  80

Gly Val Ala Pro Ser Ala Asp Leu Tyr Ala Val Lys Val Leu Gly Ala
                        85                  90                  95

Asn Gly Arg Gly Ser Val Ser Gly Ile Ala Gln Gly Leu Glu Trp Ala
                    100                 105                 110

Ala Thr Asn Asn Met His Ile Ala Asn Met Ser Leu Gly Ser Asp Ala
```

```
                115                 120                 125
Pro Ser Thr Thr Leu Glu Arg Ala Val Asn Tyr Ala Thr Ser Arg Gly
            130                 135                 140

Val Leu Val Ile Ala Ala Thr Gly Asn Asn Gly Thr Gly Ser Ile Gly
145                 150                 155                 160

Tyr Pro Ala Arg Tyr Ala Asn Ala Met Ala Val Gly Ala Thr Asp Gln
                165                 170                 175

Asn Asn Arg Arg Ala Ser Phe Ser Gln Tyr Gly Thr Gly Ile Asp Ile
            180                 185                 190

Val Ala Pro Gly Val Gly Ile Gln Ser Thr Tyr Leu Asn Asn Ser Tyr
            195                 200                 205

Ala Ser Met Pro Gly Thr Ser Met Ala Thr Pro His Val Ala Gly Val
            210                 215                 220

Ala Ala Leu Val Lys Gln Lys Asn Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Asp Ala Ala Thr Arg
            260                 265

<210> SEQ ID NO 67
<211> LENGTH: 269
<212> TYPE: PRT
<213> ORGANISM: Unknown
<220> FEATURE:
<223> OTHER INFORMATION: B gibsonii clade

<400> SEQUENCE: 67

Gln Gln Thr Val Pro Trp Gly Ile Thr Arg Val Gln Ala Pro Ala Val
1               5                   10                  15

His Asn Arg Gly Val Thr Gly Ser Gly Val Arg Val Ala Ile Leu Asp
            20                  25                  30

Ser Gly Ile Ser Gln His Ser Asp Leu Thr Ile Arg Gly Gly Ala Ser
        35                  40                  45

Phe Ile Pro Gly Glu Pro Thr Thr Ala Asp Leu Asn Gly His Gly Thr
50                  55                  60

His Val Ala Gly Thr Val Ala Ala Leu Asn Asn Ser Ile Gly Val Ile
65                  70                  75                  80

Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Ala Asn Asn Met His Ile Ala Asn Met Ser Leu Gly Ala Asp Ala
            115                 120                 125

Pro Ser Ser Thr Leu Glu Arg Ala Val Asn Tyr Ala Thr Ser Gln Gly
            130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
            195                 200                 205

Ala Ser Leu Asn Gly Thr Ser Met Ala Thr Pro His Val Ala Gly Ala
```

Ala Ala Leu Val Lys Gln Arg Asn Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265

<210> SEQ ID NO 68
<211> LENGTH: 269
<212> TYPE: PRT
<213> ORGANISM: Unknown
<220> FEATURE:
<223> OTHER INFORMATION: B gibsonii clade

<400> SEQUENCE: 68

Gln Gln Thr Val Pro Trp Gly Ile Thr Arg Val Gln Ala Pro Ala Val
1               5                   10                  15

His Asn Arg Gly Val Thr Gly Ser Gly Val Arg Val Ala Ile Leu Asp
                20                  25                  30

Ser Gly Ile Ser Gln His Ser Asp Leu Thr Ile Arg Gly Gly Ala Ser
            35                  40                  45

Phe Val Pro Gly Glu Pro Thr Thr Glu Asp Leu Asn Gly His Gly Thr
    50                  55                  60

His Val Ala Gly Thr Val Ala Ala Leu Asn Asn Ser Phe Gly Val Ile
65                  70                  75                  80

Gly Val Ala Pro Ser Ala Asp Leu Tyr Ala Val Lys Val Leu Gly Ala
                85                  90                  95

Gly Gly Arg Gly Ser Val Ser Gly Ile Ala Gln Gly Leu Glu Trp Ala
            100                 105                 110

Ala Ala Asn Asn Met His Ile Ala Asn Met Ser Leu Gly Ala Asp Ala
        115                 120                 125

Pro Ser Ser Thr Leu Glu Arg Ala Val Asn Tyr Ala Thr Ser Arg Gly
130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Ala Ser Leu Asn Gly Thr Ser Met Ala Thr Pro His Val Ala Gly Val
210                 215                 220

Ala Ala Leu Val Lys Gln Arg Asn Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Glu Ala Ala Ile Arg
            260                 265

<210> SEQ ID NO 69
<211> LENGTH: 84
<212> TYPE: PRT
<213> ORGANISM: Artificial Sequence
<220> FEATURE:
<223> OTHER INFORMATION: consensus motif

```
<220> FEATURE:
<221> NAME/KEY: VARIANT
<222> LOCATION: (13)..(13)
<223> OTHER INFORMATION: X is any amino acid
<220> FEATURE:
<221> NAME/KEY: VARIANT
<222> LOCATION: (17)..(17)
<223> OTHER INFORMATION: X = A or V
<220> FEATURE:
<221> NAME/KEY: VARIANT
<222> LOCATION: (18)..(18)
<223> OTHER INFORMATION: X = M or V
<220> FEATURE:
<221> NAME/KEY: VARIANT
<222> LOCATION: (20)..(20)
<223> OTHER INFORMATION: X is any amino acid
<220> FEATURE:
<221> NAME/KEY: VARIANT
<222> LOCATION: (23)..(23)
<223> OTHER INFORMATION: X = E or D
<220> FEATURE:
<221> NAME/KEY: VARIANT
<222> LOCATION: (25)..(25)
<223> OTHER INFORMATION: X = V or I
<220> FEATURE:
<221> NAME/KEY: VARIANT
<222> LOCATION: (26)..(26)
<223> OTHER INFORMATION: X = E or D
<220> FEATURE:
<221> NAME/KEY: VARIANT
<222> LOCATION: (27)..(29)
<223> OTHER INFORMATION: X is any amino acid
<220> FEATURE:
<221> NAME/KEY: VARIANT
<222> LOCATION: (31)..(32)
<223> OTHER INFORMATION: X is any amino acid
<220> FEATURE:
<221> NAME/KEY: VARIANT
<222> LOCATION: (33)..(33)
<223> OTHER INFORMATION: X = I or S
<220> FEATURE:
<221> NAME/KEY: VARIANT
<222> LOCATION: (34)..(34)
<223> OTHER INFORMATION: X is any amino acid
<220> FEATURE:
<221> NAME/KEY: VARIANT
<222> LOCATION: (36)..(36)
<223> OTHER INFORMATION: X = E or Q
<220> FEATURE:
<221> NAME/KEY: VARIANT
<222> LOCATION: (37)..(37)
<223> OTHER INFORMATION: X is any amino acid
<220> FEATURE:
<221> NAME/KEY: VARIANT
<222> LOCATION: (38)..(38)
<223> OTHER INFORMATION: X = E or D
<220> FEATURE:
<221> NAME/KEY: VARIANT
<222> LOCATION: (39)..(39)
<223> OTHER INFORMATION: X = E or D
<220> FEATURE:
<221> NAME/KEY: VARIANT
<222> LOCATION: (43)..(43)
<223> OTHER INFORMATION: X = E or D
<220> FEATURE:
<221> NAME/KEY: VARIANT
<222> LOCATION: (46)..(46)
<223> OTHER INFORMATION: X = H or Y
<220> FEATURE:
<221> NAME/KEY: VARIANT
<222> LOCATION: (49)..(49)
<223> OTHER INFORMATION: X = E or D
<220> FEATURE:
<221> NAME/KEY: VARIANT
<222> LOCATION: (50)..(50)
<223> OTHER INFORMATION: X = T or F
<220> FEATURE:
<221> NAME/KEY: VARIANT
<222> LOCATION: (58)..(58)
```

-continued

```
<223> OTHER INFORMATION: X =  L or I
<220> FEATURE:
<221> NAME/KEY: VARIANT
<222> LOCATION: (59)..(59)
<223> OTHER INFORMATION: X is any amino acid
<220> FEATURE:
<221> NAME/KEY: VARIANT
<222> LOCATION: (64)..(64)
<223> OTHER INFORMATION: X = V or A
<220> FEATURE:
<221> NAME/KEY: VARIANT
<222> LOCATION: (65)..(65)
<223> OTHER INFORMATION: X = S or A
<220> FEATURE:
<221> NAME/KEY: VARIANT
<222> LOCATION: (68)..(68)
<223> OTHER INFORMATION: X = S or L
<220> FEATURE:
<221> NAME/KEY: VARIANT
<222> LOCATION: (73)..(73)
<223> OTHER INFORMATION: X = S or A
<220> FEATURE:
<221> NAME/KEY: VARIANT
<222> LOCATION: (84)..(84)
<223> OTHER INFORMATION: X is any amino acid

<400> SEQUENCE: 69

Ala Glu Glu Ala Lys Glu Lys Tyr Leu Ile Gly Phe Xaa Glu Gln Glu
1               5                   10                  15

Xaa Xaa Ser Xaa Phe Val Xaa Gln Xaa Xaa Xaa Xaa Xaa Glu Xaa Xaa
            20                  25                  30

Xaa Xaa Ser Xaa Xaa Xaa Xaa Val Glu Ile Xaa Leu Leu Xaa Glu Phe
        35                  40                  45

Xaa Xaa Ile Pro Val Leu Ser Val Glu Xaa Xaa Pro Glu Asp Val Xaa
    50                  55                  60

Xaa Leu Glu Xaa Asp Pro Ala Ile Xaa Tyr Ile Glu Glu Asp Ala Glu
65                  70                  75                  80

Val Thr Thr Xaa
```